(12) United States Patent
Scanlan et al.

(10) Patent No.: US 6,979,750 B1
(45) Date of Patent: Dec. 27, 2005

(54) THYRONAMINE DERIVATIVES AND ANALOGS AND METHODS OF USE THEREOF

(75) Inventors: Thomas S. Scanlan, San Francisco, CA (US); Matthew E. Hart, San Francisco, CA (US); David K. Grandy, Portland, OR (US); James R. Bunzow, Portland, OR (US)

(73) Assignees: The Regents of the University of California, Oakland, CA (US); Oregon Health & Science University, Portland, OR (US)

( * ) Notice: Subject to any disclaimer, the term of this patent is extended or adjusted under 35 U.S.C. 154(b) by 82 days.

(21) Appl. No.: 10/418,399

(22) Filed: Apr. 18, 2003

(51) Int. Cl.[7] ....................... C07C 211/27; A61K 31/35
(52) U.S. Cl. ..................................... 564/374; 514/654
(58) Field of Search ............................... 564/355, 374; 514/654

(56) References Cited

OTHER PUBLICATIONS

Database CAPLUS on STN, Acc. No. 1971:135556, Fuller et al., J. of Medicinal Chemistry (1971), 14(4), p. 322-325 (abstract).*
Yen, P.M., "Physiological and Molecular Basis of Thyroid Hormone Action", *Physiol. Rev.* 81: 1097-1142, 2001.
Falkenstein, E., et al., "Multiple Actions of Steroid Hormones-A Focus on Rapid, Nongenomic Effects", *Pharmacol. Rev.* 52: 513-555, 2000.
Walker, J.D., et al., "The novel effects of 3,5,3'-triiodo-L-thyronine on myocyte contractile function and β-adrenergic responsivness in dilated cardiomyopathy", *J. Thorac. Cardiovasc. Surg.* 108: 672-679, 1994.
Sun, Z.-Q., et al., "Effects of thyroid hormone on action potential and repolarizing currents in rat ventricular myocytes", *Am. J. Physiol. Endocrinol. Metab.* 278: E302-E307, 2000.
Hamilton, M.A., et al., "Safety and Hemodynamic Effects of Intravenous Triiodothyronine in Advanced Congestive Heart Failure", *Am. J. Cardiol.* 81: 443-447, 1998.
Buu-Hoi, N.P., et al., "Thyronamine, a New Substance with Long-acting positive Inotropic Effect", *Pharmacology* 2: 281-287, 1969.
Boissier, J.R., et al., "Differential Inotropic-Chronotropic Action of Thyronamine", *Eur. J. Pharmacol.* 22: 141-149, 1973.
Cote, P., et al., "Thyronamine, a new inotropic agent: its cardiovascular effects and mechanism of action", *Cardiovascular Res.* 8: 721-730, 1974.
Dratman, M., "On the Mechanism if Action of Thyroxin, an Amino Acid Analog of Tyrosine", *J. theor. Biol.*, 46: 255-270, 1974.
Han, et al., "Synthesis of side chain-modified idothyronines", *Int. J. Peptide Protien Res.*, 30: 652-661, 1987.
Rozanov, C.B., et al., "Immunohistochemical Mapping of Brain Triiodothyronine Reveals Prominent Localization in Central Noradrenergic Systems", *Neuroscience*, 74: 897-915, 1996.
Tomita, K., et al., "Synthesis and Biological Activity of Some Triiodinated Analogues of Thyroxine", *J. Biol. Chem.* 219: 595-604, 1956.
Biondi, B., et al., "Effects of Subclinical Thyroid Dysfunction on the Heart", *Ann Intern Med.*, 137: 904-914, 2002.
Thibault, O., "Recherhes sur la nature de la <<thyroxine active>>. Renforcement immediate par la thyroxamine des effets de l'adrénaline sur divers muscles lisses", 1951 *C.R. Soc. Chim. biol.*, 797-800.
Meyer, T., et al., "Triiodothyronamine- A Beta-adrenergic Metabolite of Triiodothyronine?", *Horm. metabol. Res.* 15: 602-606, 1983.
Buu Hoi; N.P. et al., "Some Biological Effects of Thyronamine", *Med. Pharmacol. exp.* 15:17-23, 1966.
Bunzow, J.R., et al., "Amphetamine, 3,4-Methylenedioxymethamphetamine, Lysergic Acid Diethylamide, and Metabolites of the Catecholamine Neurotransmitters are Agonists of a Rat Trace Amine Receptor", *Mol. Pharmacol.* 60: 1181-1188, 2001.
Borowsky, B., et al., "Trace amines: Identification of a family of mammalian G protein-coupled receptors", *Proc. Natl. Acad. Sci.* 98: 8966-8971, 2001.
Stöhr, R., "Synthese des Thyronamins", *Hoppe-Seyler Z. physiol. Chem.* 201: 142-149, 1931.
Petit, L. et al., "A Synthesis of Thyronamine and its Lower Homolog", *J. org. Chem.* 26: 3832-4, 1961.
Cody et al., "Molecular Structure and Biochemical Activity of 3,5,3'-Triiodothyronamine", *Endocrine Research*, 10: 91-99, 1984.

* cited by examiner

*Primary Examiner*—Brian Davis
(74) *Attorney, Agent, or Firm*—Woodcock Washburn LLP

(57) ABSTRACT

Thyronamine derivatives and analogs, methods of using such compounds, and pharmaceutical compositions containing them are disclosed. Methods of preparing such compounds are also disclosed.

17 Claims, 15 Drawing Sheets

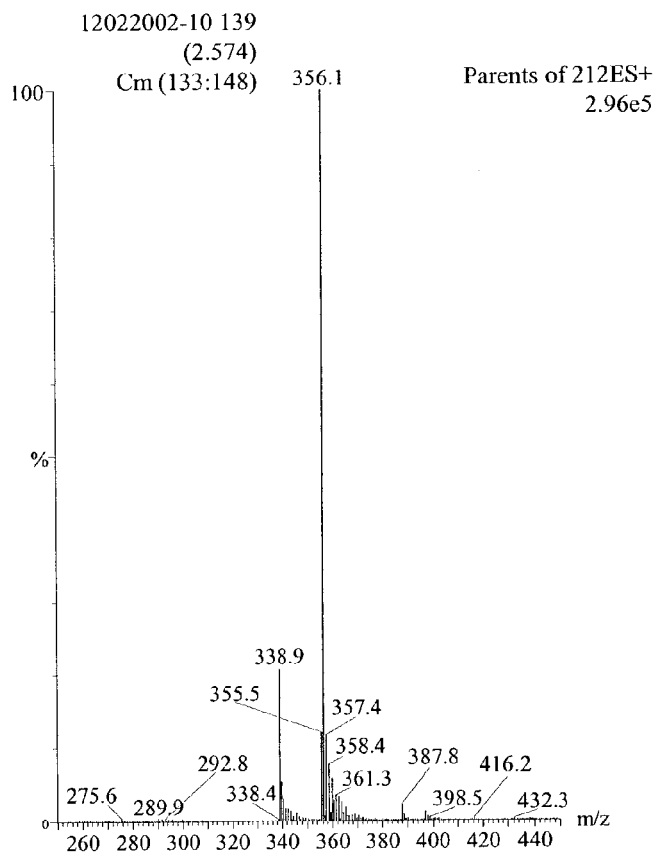
Figure 5C
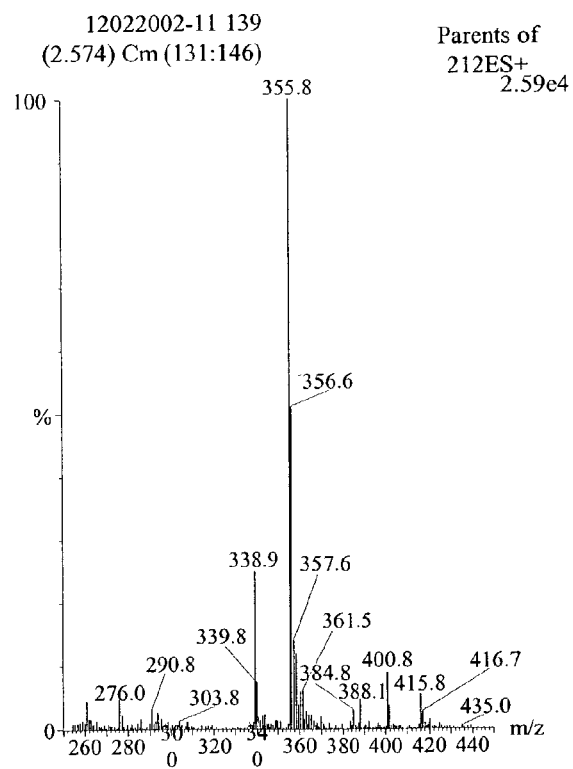

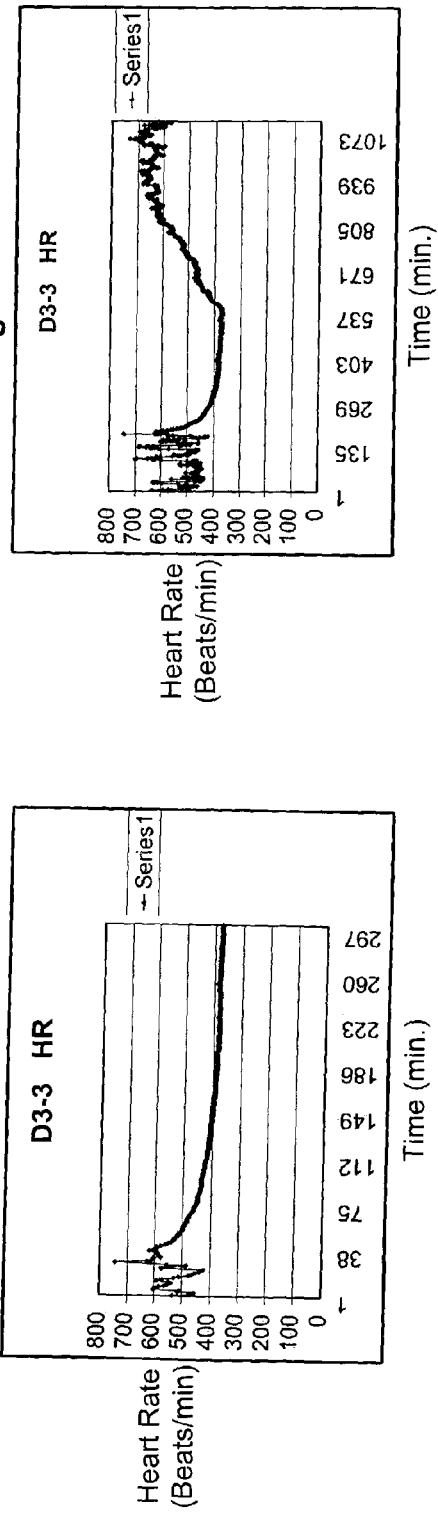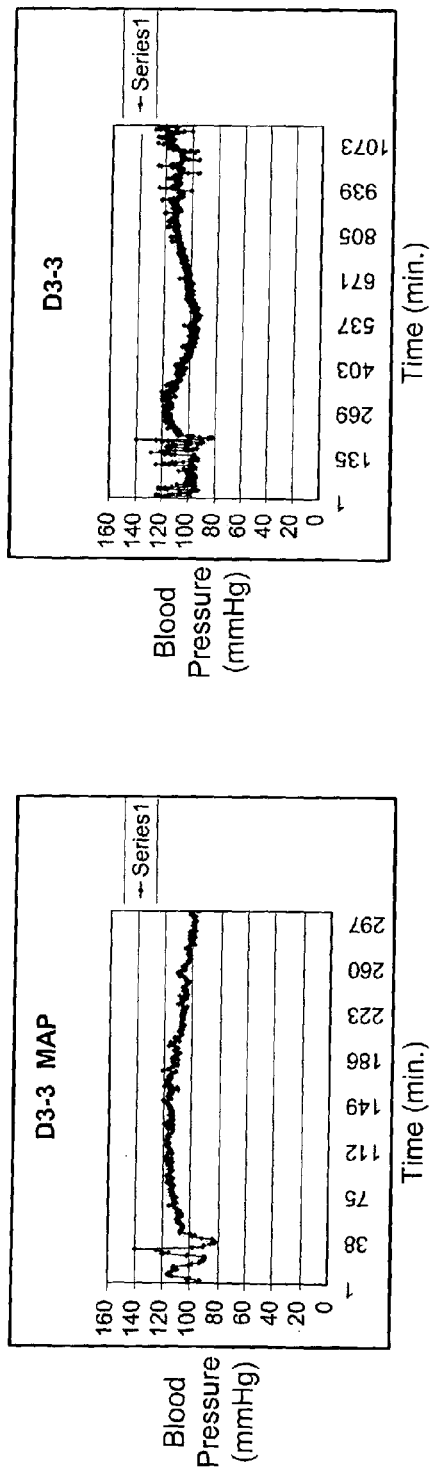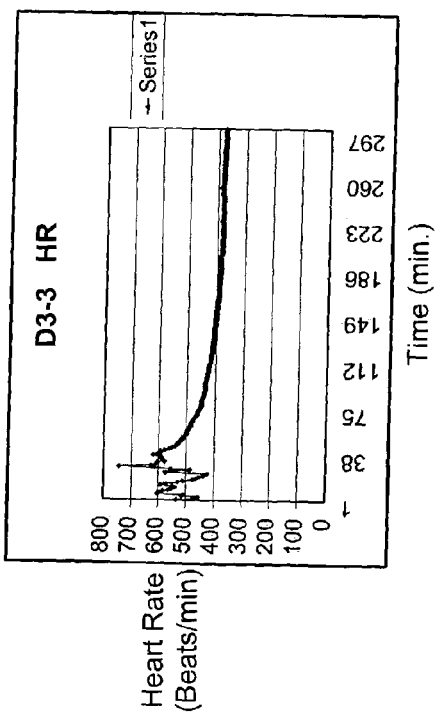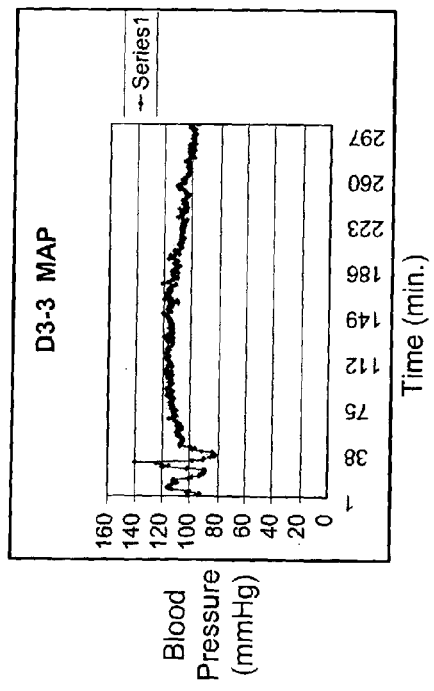

THYRONAMINE DERIVATIVES AND ANALOGS AND METHODS OF USE THEREOF

This invention was made with Government support by Grant Nos. DK52798, DA10703, DA12408, and DA07262-09, awarded by the National Institutes of Health. The Government has certain rights in this invention.

FIELD OF THE INVENTION

This invention generally relates to derivatives and analogs of thyroid hormone. More specifically, the invention relates to thyronamine derivatives and analogs of thyroid hormone, pharmaceutical compositions containing the thyronamine derivatives and analogs, methods of making the thyronamine derivatives and analogs and methods of use thereof.

BACKGROUND OF THE INVENTION

Thyroid hormone is an important regulator of vertebrate development and homeostasis. Yen, P. M., 2001, *Physiol. Rev.* 81, 1097–1142. Thyroid hormone is critical for normal fetal brain development, and brain disorders such as cretinism can result from a lack of thyroid hormone in the developing fetus. In adults, thyroid hormone exerts effects in almost all tissues, and important processes such as metabolic rate, thermal regulation, lipid inventory, cardiac function, and bone maintenance are affected by thyroid hormone. Individuals with excess blood levels of thyroid hormone (hyperthyroid) generally have elevated metabolic rate and body temperature, decreased serum cholesterol, and increased heart rate compared to those with normal thyroid hormone levels (euthyroid). Conversely, hypothyroidism is characterized by depressed metabolic rate and body temperature, elevated serum cholesterol, and decreased heart rate compared to euthyroid controls.

Thyroxine ($T_4$, FIG. 1) is the predominant form of thyroid hormone that is secreted from the thyroid gland, and $T_4$ is converted to the more physiologically active 3,5,3'-triiodothyronine ($T_3$, FIG. 1) by enzymatic deiodination in peripheral target tissues. Three different deiodinases have been identified to date (D-I, D-II, and D-III). The D-I and D-II enzymes mediate "outer ring" deiodination such as the conversion of $T_4$ to $T_3$, whereas the D-III enzyme mediates "inner ring" deiodination, exemplified by the conversion of $T_4$ to reverse-$T_3$ ($rT_3$, FIG. 1). To date, no significant biological activity has been ascribed to $rT_3$ even though significant blood levels of this metabolite are found. Moreover, a variety of further deiodinated forms of $T_4$ are known to exist in vivo and the biological significance of these metabolites in unclear.

The majority of known biological activities of thyroid hormone are mediated by binding of $T_3$ to thyroid hormone receptors (TRs). The TRs belong to the nuclear receptor superfamily of hormone-activated transcription factors, and there are two different TR genes, TRα and TRβ. The mRNAs of TRα and TRβ are further processed giving rise to four TR isoforms (TRα$_1$, TRα$_2$, TRβ$_1$, TRβ$_2$) that are co-expressed in ratios that are unique to each tissue. $T_3$ binds to the ligand binding domain (LBD) of nuclear localized TRs, and the activated TR regulates the transcription of hormone responsive genes. In this mode of action, the effects of thyroid hormone are manifested exclusively through positive and negative regulation of hormone-responsive gene transcription.

There are, however, physiological effects of thyroid hormone that are not readily explained by a transcription regulation mode of action. These so-called "non-genomic effects" are characterized by a rapid onset in response to hormone and/or insensitivity to translation inhibitors, such as cyclohexamide. Specific examples of such effects include the rapid contractile response to $T_3$ in cultured cardiac myocytes, the shortening of the action potential with concomitant attenuation of repolarizing currents in ventricular myocytes, and in studies in animals. Falkenstein, E., et al., 2000, *Pharmacol. Rev.* 52, 513–555; Walker, J. D., et al., 1994, *J. Thorac. Cardiovasc. Surg.* 108, 672–679; Sun, Z.-Q., et al., 2000, *Am. J. Physiol. Endocrinol. Metab.* 278, E302–E307; Hamilton, M. A., et al., 1998, *Am. J. Cardiol.* 81, 443–447; Buu-Hoi, N. P., et al., 1969, *Pharmacology* 2, 281–287; Boissier, J. R., et al., 1973, *Eur. J. Pharmacol.* 22, 141–149; Cote, P., et al., 1974, *Cardiovascular Res.* 8, 721–730. The rapid rate of these effects suggests that they are mediated by receptors other than the nuclear TRs in response to a thyroid hormone. The source and mechanism of these non-genomic effects are not known. Dratman, 1974, *J. theor. Biol.*, 46, 255–270; Han, et al., 1987, *Int. J. Peptide Protein Res.*, 30, 652–661; Rozanov and Dratman, 1996, *Neuroscience*, 74, 897–915; Tomita and Lardy, *J. Biol. Chem.* 219: 595–604, 1956. A need exists in the art to understand and regulate/modulate these non-genomic effects related to thyroid hormone. The present invention is directed to these, as well as other important ends.

SUMMARY OF THE INVENTION

The invention is generally related to thyronamine derivatives and analogs of thyroid hormone, pharmaceutical compositions containing the thyronamine derivatives and analogs, methods of making the thyronamine derivatives and analogs and methods of use thereof.

In one embodiment, thyronamine derivatives and analogs are provided of formula:

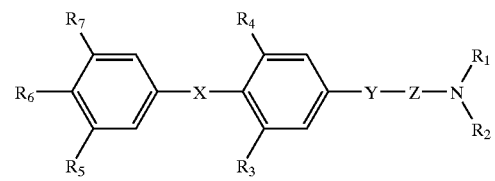

or a stereoisomer, prodrug, pharmaceutically acceptable salt, hydrate, solvate, acid salt hydrate, N-oxide or isomorphic crystalline form thereof;

wherein independently, $R_1$ and $R_2$ are: H, lower alkyl, cyclic alkyl, or benzyl;

Y and Z are: $CH_2$, CHR, $C(R)_2$, CHOH, or CHOR;

$R_3$, $R_4$, $R_5$, and $R_7$ are: H, I, Br, Cl, F, $CH_3$, $CF_3$, CN, $OCH_3$, $CH_2CH_3$, or $CH(CH_3)_2$;

$R_6$ is: OH, H, SH, F, $CF_3$, lower alkyl, $NH_2$, NHR, or $N(R)_2$;

X is: O, S, SO, $SO_2$, NH, NR, $CH_2$, CHR, $C(R)_2$, or $CH_2O$; and

R is lower alkyl; and provided that the compound is not thyronamine ($T_0$AM), 3,5-diiodothyronamine ($T_2$AM), 3,5,3'-triiodothyronamine ($T_3$AM), thyroxamine ($T_4$AM), 3,5,3',5'-tetraiodothyroethanolamine, 3,5,3'-triiodothyroethanolamine, or 3,5-diiodothyroethanolamine.

In certain embodiments, $R_4$ and $R_5$ are H, $CH_3$, $CF_3$, CN, $OCH_3$, $CH_2CH_3$, or $CH(CH_3)_2$, and in a further detailed embodiment, $R_1$ and $R_2$ are H, $R_3$ is I, $R_4$, $R_5$, and $R_7$ are H, $R_6$ is OH, X is O, Y and Z are each $CH_2$. In another detailed embodiment, $R_4$ is: H, $CH_3$, $CF_3$, CN, $OCH_3$, $CH_2CH_3$, or $CH(CH_3)_2$; and $R_3$ and $R_5$ are: I, Br, Cl, or F, and in other detailed embodiments, $R_1$ and $R_2$ are H, $R_4$ and $R_7$ are H, $R_3$ and $R_5$ are I, $R_6$ is OH, X is O, Y and Z are each $CH_2$. In another detailed embodiment, $R_1$ and $R_2$ are H, $R_4$ is H, $R_3$, $R_5$, and $R_7$ are I, $R_6$ is OH, X is O, Y and Z are each $CH_2$.

In another embodiment, pharmaceutical compositions are provided comprising at least one pharmaceutically acceptable carrier or excipient and an effective amount of the compound.

In other detailed embodiments, an antibody is provided that specifically binds to the compound.

In a further embodiment, pharmaceutical compositions are provided comprising at least one pharmaceutically acceptable carrier or excipient and an effective amount of the compound.

In a further embodiment, methods of exerting a positive inotropic effect on the heart without affecting the heart rate of a mammalian subject are provided comprising the step of administering to the subject an effective amount of the compounds described herein. In a further embodiment, methods of lowering the core body temperature of a mammalian subject are provided comprising the step of administering to the subject an effective amount of the compounds described herein, and further wherein administering the compounds induces torpor or hibernation in the subject.

In another embodiment, methods for alleviating a disease state in a mammal believed to be responsive to treatment with a thyronamine agonist are provided, comprising the step of administering to the mammal a therapeutic amount of a compound of formula:

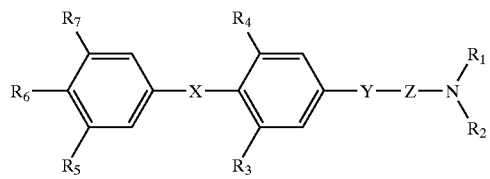

or a stereoisomer, prodrug, pharmaceutically acceptable salt, hydrate, solvate, acid salt hydrate, N-oxide or isomorphic crystalline form thereof;
wherein independently,
$R_1$ and $R_2$ are: H, lower alkyl, cyclic alkyl or benzyl;
Y and Z are: $CH_2$, CHR, $CR_2$, CHOH, or CHOR;
$R_3$, $R_4$, $R_5$, and $R_7$ are: H, I, Br, Cl, F, $CH_3$, $CF_3$, CN, $OCH_3$, $CH_2CH_3$, or $CH(CH_3)_2$;
$R_6$ is: OH, H, SH, F, $CF_3$, lower alkyl, $NH_2$, NHR, or $N(R)_2$;
X is: O, S, SO, $SO_2$, NH, NR, $CH_2$, CHR, $C(R)_2$, or $CH_2O$; and
R is lower alkyl; and
provided that the compound is not thyronamine ($T_0AM$), 3,5-diiodothyronamine ($T_2AM$), 3,5,3'-triiodothyronamine ($T_3AM$), thyroxamine ($T_4AM$), 3,5,3',5'-tetraiodothyroethanolamine, 3,5,3'-triiodothyroethanolamine, or 3,5-diiodothyroethanolamine.

In detailed embodiments, the methods provide administering a composition which is an agonist of a G protein coupled receptor, for example, a trace amine receptor.

In another embodiment, methods for alleviating a disease state in a mammal believed to be responsive to treatment with a thyronamine antagonist are provided, comprising the step of administering to the mammal a therapeutic amount of a compound of formula:

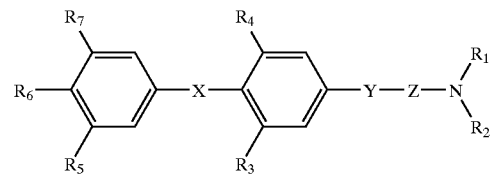

or a stereoisomer, prodrug, pharmaceutically acceptable salt, hydrate, solvate, acid salt hydrate, N-oxide or isomorphic crystalline form thereof;
wherein independently,
$R_1$ and $R_2$ are: H, lower alkyl, cyclic alkyl or benzyl;
Y and Z are: $CH_2$, CHR, $CR_2$, CHOH, or CHOR;
$R_3$, $R_4$, $R_5$, and $R_7$ are: H, I, Br, Cl, F, $CH_3$, $CF_3$, CN, $OCH_3$, $CH_2CH_3$, or $CH(CH_3)_2$;
$R_6$ is: OH, H, SH, F, $CF_3$, lower alkyl, $NH_2$, NHR, or $N(R)_2$;
X is: O, S, SO, $SO_2$, NH, NR, $CH_2$, CHR, $C(R)_2$, or $CH_2O$; and
R is lower alkyl; and
provided that the compound is not thyronamine ($T_0AM$), 3,5-diiodothyronamine ($T_2AM$), 3,5,3'-triiodothyronamine ($T_3AM$), thyroxamine ($T_4AM$), 3,5,3',5'-tetraiodothyroethanolamine, 3,5,3'-triiodothyroethanolamine, or 3,5-diiodothyroethanolamine.

In detailed embodiments, the methods provide administering a composition which is an antagonist of a G protein coupled receptor, for example, a trace amine receptor.

In a further detailed embodiment, the methods are provided for treating the disease state which is congestive heart failure, or treating the disease state is fever or heatstroke. In a further detailed embodiment, the methods are provided for treating the disease state which is bipolar disorder, depression, schizophrenia, eating disorders, anxiety, seizure, epilepsy, insomnia and sleeping disorders, gastro esophageal reflux disease, diseases involving gastrointestinal motility or asthma. In a detailed embodiment, methods are provided for treating the disease state which is diabetes, cardiac arrhythmia, stroke, osteoporosis, obesity, atherosclerosis, hypertension, hyperthyroidism or hypothyroidism.

In a further detailed embodiment, methods of treating a mammalian subject during surgery are provided, comprising the step of administering a therapeutically effective amount of the compound to the subject. Furthermore, the method of treating the subject during surgery reduces the core body temperature and induces anesthesia in the subject. Furthermore, the method reduces blood loss of the subject.

In another embodiment, methods of exerting a positive inotropic effect on the heart without affecting the heart rate of a mammalian subject are provided comprising the step of administering to the subject a 3,5-diiodothyronamine compound or a 3,5,3'-triiodothyronamine compound, or a stereoisomer, prodrug, pharmaceutically acceptable salt, hydrate, solvate, acid salt hydrate, N-oxide or isomorphic crystalline form thereof.

In another embodiment, methods of lowering the core body temperature of a mammalian subject are provided comprising the step of administering to the subject a 3,5-diiodothyronamine compound or a 3,5,3'-triiodothyronamine compound, or a stereoisomer, prodrug, pharmaceutically acceptable salt, hydrate, solvate, acid salt hydrate, N-oxide or isomorphic crystalline form thereof.

In another embodiment, methods of treating a mammalian subject having a disease state which is alleviated by treatment with a thyronamine agonist are provided comprising the step of administering to the subject a therapeutically effective amount of a 3,5-diiodothyronamine compound or a 3,5,3'-triiodothyronamine compound, or a stereoisomer, prodrug, pharmaceutically acceptable salt, hydrate, solvate, acid salt hydrate, N-oxide or isomorphic crystalline form thereof.

In another embodiment, methods of treating a mammalian subject having a disease state which is alleviated by treatment with a thyronamine antagonist are provided comprising the step of administering a therapeutically effective amount of a 3,5-diiodothyronamine compound or a 3,5,3'-triiodothyronamine compound, or a stereoisomer, prodrug, pharmaceutically acceptable salt, hydrate, solvate, acid salt hydrate, N-oxide or isomorphic crystalline form thereof.

In another embodiment, methods for preparing a protected phenylboronic acid are provided comprising the steps of providing a protected p-bromophenol; and reacting the protected p-bromophenol with alkyl lithium and $B(OR)_3$, and hydrolyzing the product of the reacting step to form a protected phenylboronic acid, where R is methyl, ethyl or propyl. In a detailed embodiment, the protected p-bromophenol is protected with a moiety selected from trimethylsilyl, tert-butyldimethylsilyl and triisopropylsilyl.

In another embodiment, methods for preparing a thyronamine derivative or a stereoisomer, prodrug, pharmaceutically acceptable salt, hydrate, solvate, acid salt hydrate, N-oxide or isomorphic crystalline form thereof are provided comprising the steps of:

contacting, in the presence of copper, an amino-protected tyramine of the formula:

1.

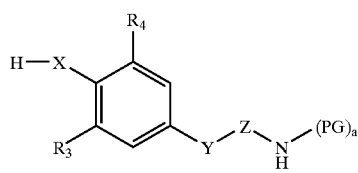

2.

3. with a hydroxyl- or thiol-protected phenylboronic acid of the formula:

4.

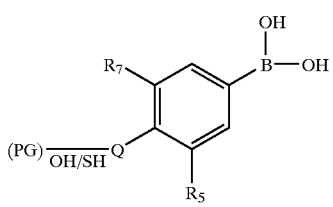

5. to form the structure of the formula:

6.

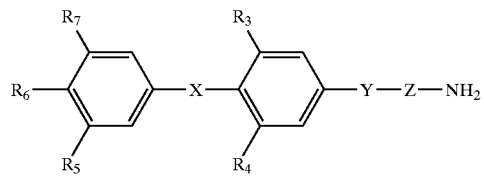

7. deprotecting the hydroxyl or thiol group; and
8. deprotecting the amino group;
wherein,
$(PG)_a$ is an amino protecting group;
$(PG)_{OH/SH}$ is a hydroxyl- or thiol-protecting group;
Q is: O or S;
X is: O, S, SO, $SO_2$, NH, NR, $CH_2$, CHR, $CR_2$, or $CH_2O$;
Y and Z are, independently: $CH_2$, CHR, $C(R)_2$, CHOH, or CHOR;
$R_3$ is: H, I, Br, Cl, or F;
$R_5$ and $R_7$ are, independently: I, Br, Cl, F, H, $CH_3$, $CF_3$, CN, $OCH_3$, $CH_2CH_3$, or $CH(CH_3)_2$;
$R_4$ is: H, $CH_3$, $CF_3$, CN, $OCH_3$, $CH_2CH_3$, or $CH(CH_3)_2$;
$R_6$ is: OH, SH; and
9. R is lower alkyl.

In another embodiment, methods are provided for preparing a thyronamine derivative or a stereoisomer, prodrug, pharmaceutically acceptable salt, hydrate, solvate, acid salt hydrate, N-oxide or isomorphic crystalline form thereof further comprising the step of independently substituting an I, Br, Cl or F at the 3' position, 5' position or both the 3' position and the 5' position. In a detailed embodiment, the method further comprises the step of O-alkylating or S-alkylating the hydroxyl or thiol functionality of the compound. In a detailed embodiment, the method further comprises the step of N-alkylating the amino functionality of the compound.

BRIEF DESCRIPTION OF THE DRAWINGS

FIG. 5A, 5B, 5C. Liquid chromatography/mass spectrometry (LC/MS) on rat brain.

FIG. 13A, 13B: Graph of heart rate vs. time (minutes), or blood pressure (mm Hg) vs. time (minutes), following intraperitoneal injection into a mouse of an iodo-thyronamine compound, Tlamine, measured over an approximately 4 hour period; FIG. 13C, 13D: Graph of heart rate vs. time (minutes), or blood pressure (mm Hg) vs. time (minutes), following intraperitoneal injection into a mouse of an iodo-thyronamine compound, T$_1$amine, measured over an approximately 17 hour period.

DETAILED DESCRIPTION OF ILLUSTRATIVE EMBODIMENTS

Figure 1:
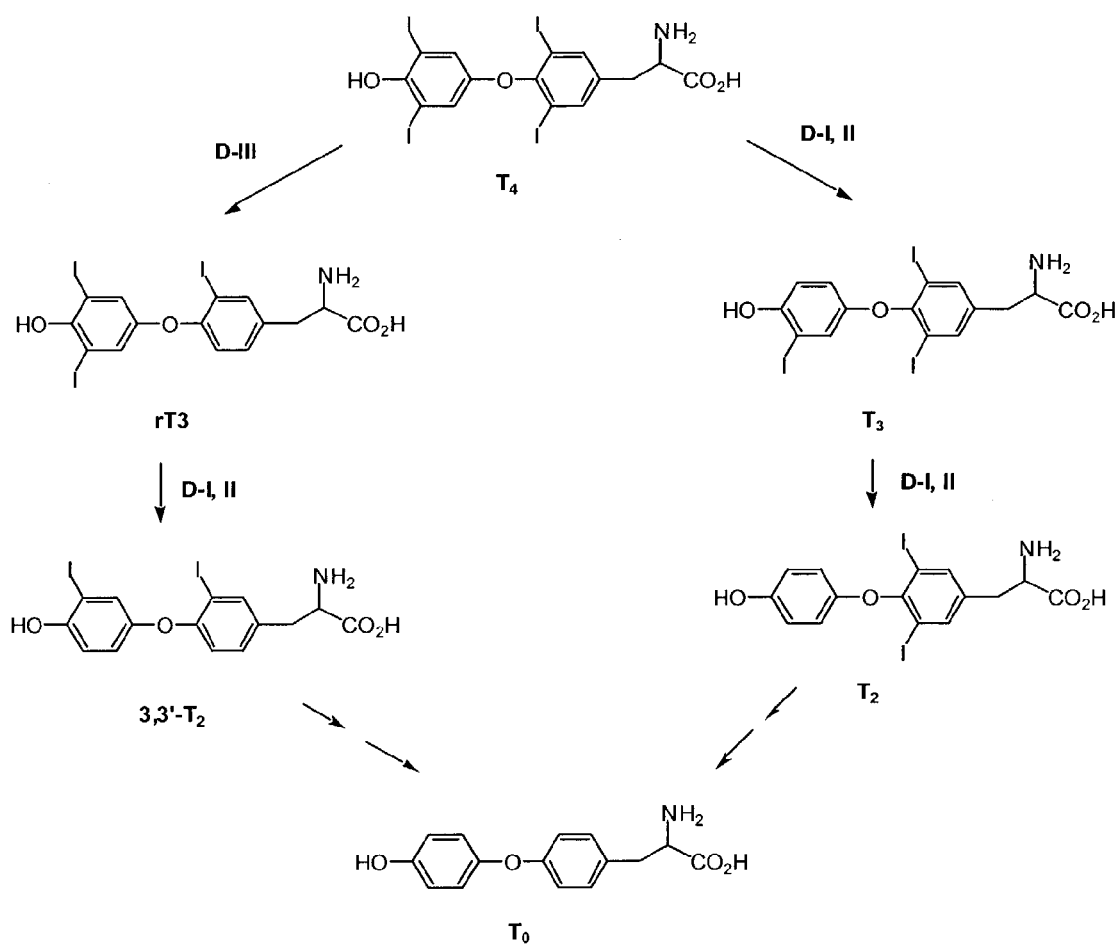
FIG. 1. Iodination state of thyroid hormone metabolites
FIG. 2. Parallel pathways of amino acid decarboxylase to produce dopamine and iodo-thyronamine.

With respect to thyronamine, "derivative" refers to a compound of the general formula:

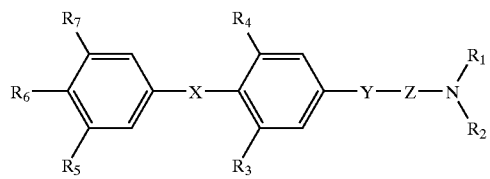

where the variables are as defined herein.

With respect to thyronamine, "analog" or "functional analog" refers to a modified form of the respective thyronamine derivative in which one or more chemically derivatized functional side ($R_1$, $R_2$, $R_3$, $R_4$, $R_5$, $R_6$ or $R_7$) or linking groups (X, Y or Z) has been modified such that the analog retains substantially the same biological activity or improved biological activity as the unmodified thyronamine derivative in vivo and/or in vitro.

"Agonist" or "thyronamine agonist" refers to an endogenous or exogenous compound, substance or entity that has affinity for and stimulates physiologic activity at cell receptors normally stimulated by naturally-occurring substances, thus triggering a biochemical response characteristic of those receptors. As used herein, the term refers to a thyronamine derivative or analog, a suitable homolog, or a portion thereof, capable of promoting at least one of the biological responses normally associated with thyronamine. For example, treatment with a thyronamine agonist can result in inotropic effects upon cardiac output, lowered body temperature of a mammalian subject, or improvement in symptoms of congestive heart failure.

"Antagonist" or "thyronamine antagonist" refers to an endogenous or exogenous compound, substance or entity that opposes the physiological effects of another compound and, at the receptor level, it is an endogenous or exogenous compound, substance or entity that has affinity for and opposes and/or blocks at least one of the normal physiological responses normal induced by another compound, substance or entity at the cell receptors. As used herein, the term refers to a thyronamine derivative or analog, a suitable homolog, or a portion thereof, which blocks at least one of the normal actions of thyronamine. For example, treatment with certain thyronamine antagonists can increase body temperature in a mammalian subject suffering from hypothermia, or reduce cardiac output in a mammalian subject.

"Receptor" refers to a molecule, a polymeric structure, or polypeptide in or on a cell that specifically recognizes and binds a compound acting as a molecular messenger, for example, neurotransmitter, hormone, lymphokine, lectin, or drug.

"Lower alkyl" refers to an optionally substituted, saturated straight or hydrocarbon having from about 1 to about 12 carbon atoms (and all combinations and subcombinations of ranges and specific numbers of carbon atoms therein), with from about 1 to about 8 carbon atoms, being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, 3-methylpentyl, 2,2-dimethylbutyl, and 2,3-dimethylbutyl. Specifically included within the definition of "lower alkyl" are those aliphatic hydrocarbon chains that are optionally substituted.

"Cyclic alkyl" refers to an optionally substituted, alkyl group having one or more rings in their structures having from about 3 to about 20 carbon atoms (and all combinations and subcombinations of ranges and specific numbers of carbon atoms therein), with from about 3 to about 10 carbon atoms being preferred. Multi-ring structures can be bridged or fused ring structures. Groups include, but are not limited to, cyclopropyl, cyclobutyl, cyclopentyl, cyclohexyl, cyclooctyl, and adamantyl. Specifically included within the definition of "cyclic alkyl" are those aliphatic hydrocarbon chains that are optionally substituted.

"Optional" or "optionally" means that the subsequently described event or circumstance may or may not occur, and that the description includes instances in which it does not. For example, optionally substituted phenyl indicates either unsubstituted phenyl, or phenyl mono-, di-, or tri-substituted, independently, with OH, COOH, lower alkyl, lower alkoxy, halo, nitro, amino, alkylamino, dialkylamino, trifluoromethyl and/or cyano.

"Effective amount" refers to an amount of a compound that can be therapeutically effective to inhibit, prevent or treat the symptoms of particular disease, disorder or side effect.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Stereoisomer, prodrug, pharmaceutically acceptable salt, hydrate, solvate, acid salt hydrate, N-oxide or isomorphic crystalline form thereof" refer to derivatives of the disclosed compounds wherein the parent compound is modified by making acid or base salts thereof. Examples of stereoisomer, prodrug, pharmaceutically acceptable salt, hydrate, solvate, acid salt hydrate, N-oxide or isomorphic crystalline form thereof include, but are not limited to, mineral or organic acid salts of basic residues such as amines; alkali or organic salts of acidic residues such as carboxylic acids; and the like. The stereoisomer, prodrug, pharmaceutically acceptable salt, hydrate, solvate, acid salt hydrate, N-oxide or isomorphic crystalline form thereof include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present compositions and methods.

Certain acidic or basic compounds can exist as zwitterions. All forms of the compounds, including free acid, free base and zwitterions, are contemplated to be within the scope of the present compositions and methods. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

"Patient" refers to animals, including mammals, preferably humans.

"Prodrug" refers to compounds specifically designed to maximize the amount of active species that reaches the desired site of reaction which are of themselves typically inactive or minimally active for the activity desired, but through biotransformation are converted into biologically active metabolites.

"Stereoisomers" refers to compounds that have identical chemical constitution, but differ as regards the arrangement of the atoms or groups in space.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

When any variable occurs more than one time in any constituent or in any formula, its definition in each occurrence is independent of its definition at every other occurrence. Combinations of substituents and/or variables are permissible only if such combinations result in stable compounds.

Methods of Treatment

Thyronamine derivatives and analogs are biogenic amines useful for medical treatments and shown to have biological activity by the following physiological and biochemical mechanisms.

(1) Thyronamine derivatives and analogs mediate rapid response ("nongenomic" effects) through activation of their cognate receptors, from the G-protein coupled receptor (GPCR) superfamily. An example of a GPCR is the trace amine receptor (TAR-1).

(2) Thyronamine derivatives and analogs are synthesized from their corresponding amino acids by an enzymatic pathway that involves decarboxylation of the amino acid as the key step that generates the arylethylamine substructure common to this group of signaling molecules.

(3) The non-selective enzyme aromatic amino acid decarboxylase (AAD), which also catalyzes the conversion of histadine to histamine and 5-hydroxytryptophan to serotonin (5-hydroxytryptamine), is known to catalyze the decarboxylation of a wide variety of natural and synthetic aromatic amino acids, requiring an aromatic group linked to an alanine as the key feature of substrate recognition. Thyroid hormones, e.g., $T_3$ and $T_4$, as well as the lower iodination state metabolites, should be substrates for AAD, giving rise to the aryl ethylamine compounds, e.g., thyronamine derivatives and analogs.

(5) The potency of thyronamine derivatives and analogs has been measured by binding to the rat trace amine receptor (rTAR-1), a G protein coupled receptor heterologously expressed in human embryonic kidney (HEK) cells. Thyronamine derivatives and analogs were found to stimulate cAMP accumulation in rTAR-1 expressing HEK cells in a dose-dependent fashion. The potency index of effective concentration for half-maximal stimulation ($EC_{50}$) of rTAR-1 was calculated from the dose-response curve for each compound. The spectrum of potencies across the thyronamine series demonstrates that the specific number and placement of iodine atoms influences potency in a critical way. 3-iodothyronamine ($T_1AM$) is the most potent rTAR-1 agonist with an $EC_{50}$ of 14 nM, followed by 3,3'-diiodothyronamine (3,3'-$T_2AM$), 3,5-diiodothyronamine ($T_2AM$), and 3, 5, 3'-triiodothyronamine ($T_3AM$). Thyronamine ($T_0AM$) is the least potent agonist with an $EC_{50}$ of 131 nM.

(6) $T_1AM$, the most potent rTAR-1 agonist, is a naturally-occurring biogenic amine which has been detected in brain extracts of rat, mouse, and guinea pig using a liquid chromatography/mass spectrometry (LC/MS) protocol. On this basis, $T_1AM$, $T_4AM$, $T_3AM$ and $T_0AM$ can be found in brain and other tissues as naturally-occurring biogenic amines.

(7) Intraperitoneal or intracerebral injection of $T_1AM$ into a mouse resulted in a decrease in core body temperature of the animal from approximately 38° C. to approximately 29° C. for a period of approximately 6.5 to 8 hours. This period was followed by a full recovery to a stable core body temperature of 38° C. in the animal. The heart rates of the animals remained constant throughout the treatment period. Blood pressure varied with the drop in body core temperature, but recovered to normal levels within the same time frame as the body core temperature recovery.

Thyronamine derivatives and analogs are effective to lower body core temperature in a mammalian subject. Experiments further demonstrate positive inotropic effects of thyronamine derivatives and analogs on cardiac output in a mammalian subject, including, but not limited to: central and peripheral effects on body temperature and metabolic rate; contraction/relaxation of various tissues and smooth muscle preparations including rodent/guinea pig ileum, vas deferens, uterus (virgin and pregnant); hanging heart assay to explore direct effects of drug(s) on heart function (inotropic and chronotropic effects); cardiac muscle; small and large blood vessels; pancreatic function (e.g. insulin release and blood glucose levels); liver function (glucagon); renal function (water balance); determine thyronamine derivative and analog content (by LC/MS) on a variety of human or other mammalian tissue extracts (e.g. brain, pancreas, liver, kidney, heart).

Because thyronamine derivatives and analogs have certain agonist and antagonist effects, compounds and pharmaceutical compositions containing the compounds as described herein would also have these effects and hence would be useful in certain methods, for example, methods of treatment, methods of exerting a positive inotropic effect, and methods of lowering the core body temperature a mammalian subject. "Core body temperature" in a human subject is approximately 37° C. "Core body temperature" in a mouse is approximately 38° C. Thyronamine derivatives and analogs are biogenic amines that can be found in a variety of tissues. Agonists and antagonists of thyronamine derivatives and analogs can have physiological effects on heart, bone, brain, central nervous system, peripheral nervous system, adipose tissue, liver, pancreas, kidney and pituitary.

The compounds and the pharmaceutical compositions containing them are useful in the treatment of conditions which affect a variety of tissues and organs of a mammalian subject. These compositions act to agonize or antagonize the effects of iodo-thyronamines or thyroid hormones in certain tissues or organs.

Agonists or antagonists of thyronamine derivatives and analogs can be synthesized. Many compounds of the general thyronamine skeleton, i.e. those compounds that contain a two atom linker between the inner phenyl ring and the basic nitrogen (at Y and Z positions) can be agonists. However, compounds of this class that contain a large group such as an aromatic substituent attached to either of the linker atoms (at Y and Z positions) can be antagonists. Alternatively, compounds that contain linkers of more than two atoms connecting the inner aromatic ring to the basic nitrogen can also be antagonists. In particular, compounds containing linkers comprised of between 3 and 7 atoms connecting the inner aromatic ring to a basic nitrogen can be antagonists.

Thyronamine derivatives and analogs lower systemic vascular resistance, increase blood volume, and exert positive inotropic effects upon cardiac function. A "positive inotropic effect" increases the force of heart muscular contraction. The combination of these positive inotropic effects on both blood circulation and the heart results in increased cardiac output. Thyronamine derivatives and analogs have a positive inotropic effect to increase cardiac output without the chronotropic effect to increase heart rate. Thyronamine derivatives and analogs as described in the present compositions and methods have cardiovascular and surgical applications. Cardiovascular applications include, for example, treatment of congestive heart failure, cardiomyopathy, cardiac arrhythmia, and management of acute stroke. These compositions and methods are useful to treat atherosclerosis or hypertension. Compositions and methods comprising thyronamine derivatives and analogs are effective to increase cardiac output, while reducing or maintaining heart rate, and reducing or maintaining blood pressure in a mammalian subject undergoing treatment.

Approximately 2 out of every 100 people between the ages of 27 and 74 have heart failure. Heart failure becomes more common with advancing age. Congestive heart failure (CHF), is a disorder in which the heart loses its ability to pump blood efficiently. CHF is a condition in which the heart cannot pump out all of the blood that enters it, which leads to an accumulation of blood in the vessels and fluid in the body tissues. CHF is almost always a chronic, long-term condition, although it can sometimes develop suddenly. This condition can affect the right side, the left side, or both sides of the heart. As the heart's pumping action is lost, blood can back up into other areas of the body: the liver, the gastrointestinal tract and extremities (right-sided heart failure), the lungs (left-sided heart failure). The most common causes of heart failure are chronic cardiovascular disease, hypertension, and coronary artery disease. Other structural or functional causes of heart failure include: valvular heart disease, congenital heart disease, dilated cardiomyopathy, lung disease, or heart tumor.

Dilated cardiomyopathy is the most common of the cardiomyopathies, comprising more than 90% of all cases that are referred to heart specialists. Symptoms often develop gradually and usually include symptoms of right heart failure, left heart failure, or both.

Dilated cardiomyopathy is a disorder in which the heart muscle is weakened and cannot pump blood efficiently. The wall muscle of the ventricles can be of normal, increased or reduced thickness, but the ventricular diameter is always enlarged. This causes decreased heart function that affects the lungs, liver, and other body systems. Dilated cardiomyopathy represents the end result of more than 50 different diseases. Causes of dilated cardiomyopathy include genetic disorders such as Friedreich's ataxia or myotonic dystrophy, myocarditis (a viral infection of the heart muscle), alcoholism, coronary artery disease, valvular heart disease, and others. In many patients, however, a cause cannot be identified, and their cardiomyopathy is considered "idiopathic." Idiopathic cardiomyopathies are likely to be genetically determined.

Thyronamine derivatives and analogs as described in the present compositions and methods can be administered during surgery and to induce anesthesia. Cardiovascular and surgical applications of these compositions and methods include, but are not limited to, reduction in body core temperature, reduction in heart rate, reduction in blood pressure, control or reduction in bleeding, and wound healing. Therapeutic applications can be particularly relevant to pediatric patients. The present compositions and methods are useful for analgesia (nociception and/or pruritis) or for induction of hibernation in mammalian subjects.

Thyronamine derivatives and analogs can induce a state of torpor in a mammalian subject. Torpor is a metabolic response exhibited by animals, e.g., mammals or avian species. It describes a temporary physiological state in which an organism's body temperature drops, and its metabolic rate is reduced. An animal is said to be in a state of torpor when it hibernates to avoid the stresses of cold and food shortages or when it estivates to avoid excessive heat or drought. Daily torpor occurs in some animals, for example, birds, rodents, rats and mice.

Compositions and methods comprising thyronamine derivatives and analogs are useful to treat disease related to defects in subcellular calcium homeostasis occurring at the mitochondria. Thyronamine derivatives and analogs play a role in thermoregulation in a mammalian subject. Thyronamine derivatives and analogs activate the TAR1 receptor and influence intracellular and extracellular calcium release. Since mitochondria are organelles that appear to participate in maintaining calcium homeostasis, and because mitochondria are central for thermogenesis to occur in muscle (a thyroid hormone-sensitive response), thyronamine derivatives and analogs can affect calcium homeostasis and thermoregulation in cells. Rapid effects of thyronamine derivatives and analogs on the heart include, but are not limited to $Na^+$ channel activation $Ca^{2+}$ ATPase activation, increased contractile function of isolated cardiac myocytes, and increased β-adrenergic responsiveness of dilated cardiomyopathic (DCM) myocytes. Thyronamine derivatives and analogs can directly couple mitochondrial function to electron transport in a way that opposes thyroid hormone.

Compositions and methods comprising thyronamine derivatives and analogs are useful to treat shock, including but not limited to, haemorrhagic (hypovolemic) shock, cardiogenic shock, neurogenic shock, and septic shock in a mammalian subject and to reduce blood loss in a mammalian subject. Shock is a medical emergency in which the organs and tissues of the body are not receiving an adequate flow of blood. This deprives the organs and tissues of oxygen (carried in the blood) and allows the buildup of waste products. Shock can result in serious damage or even death. The signs of shock (hypovolemic shock) are indicative of low peripheral blood flow and sympatheticoadrenal activity excess. Septic shock results from the damaging consequences of bacteria and toxins which include poor functioning of the heart muscle, widening of the diameter of the blood vessels, a drop in blood pressure, activation of the blood clotting system causing blood clots, followed by a risk of uncontrollable bleeding, damage to the lungs causing acute respiratory distress syndrome, liver failure, kidney failure, and coma. The patient in shock condition appears to be restless, anxious, and fearful. This restlessness can vary to apathy; in this situation the patient seems sleepy. After a while, if untreated or if the blood loss is underestimated, the patient will complain of a chilly sensation and at this time the apathy rapidly progress to coma. The most common and important signs are: changes in blood pressure (arterial and venous blood pressure are decreased), nausea, vomiting, tachycardia, and vasoconstriction (in this case is an effort to compensate the reduced cardiac output). In haemorragic shock the heart can receive 25% of the total cardiac output versus the normal 5–8%. Other signs include pale and cold skin, tachypnea and all the bloods changes as hemodilution, hormonal changes, pH changes, or renal dysfunction. To treat shock in a patient, pharmaceutical compositions comprising thyronamine derivatives and analogs can be administered to lower systemic vascular resistance, increase blood volume, and exert inotropic effects upon cardiac function resulting in an increased cardiac output for the patient, in addition to providing treatment for the patient's underlying condition.

Compositions and methods comprising thyronamine derivatives and analogs are useful to treat neoplasias. Thyronamine derivatives and analogs lower body temperature and decrease metabolic rate and are effective in treating fast-growing neoplasias by limiting their metabolic rate. The method and compositions can be used to treat neoplasia in a subject in need of treatment. Neoplasias include, without limitation, carcinomas, particularly those of the bladder, breast, cervix, colon, head, kidney, lung, neck, ovary, prostate, and stomach; lymphocytic leukemias, particularly acute lymphoblastic leukemia and chronic lymphocytic leukemia; myeloid leukemias, particularly acute monocytic leukemia, acute promyelocytic leukemia, and chronic myelocytic leukemia; malignant lymphomas, particularly Burkitt's lymphoma and Non-Hodgkin's lymphoma; malignant melanomas; myeloproliferative diseases; sarcomas, particularly Ewing's sarcoma, hemangiosarcoma, Kaposi's sarcoma, liposarcoma, peripheral neuroepithelioma, and synovial sarcoma; and mixed types of neoplasias, particularly carcinosarcoma and Hodgkin's disease. The methods and compositions can be used to treat breast cancer, colon cancer, leukemia, lung cancer, malignant melanoma, ovarian cancer, or prostate cancer.

Thyronamine derivatives and analogs as described in the present compositions and methods are useful, e.g., to control uterine contractions and/or bleeding ante-partum or postpartum, and to control blood loss as a result of disease or injury.

Thyronamine derivatives and analogs as described in the present compositions and methods are useful, e.g., as an antipyrogen to treat fever, or to treat heatstroke, hot flashes related to menopause, antihelmenthic drinking (water balance) behavior, male fertility, or female fertility. Fever or heat stroke results in an increase in the core body temperature of the subject.

Thyronamine derivatives and analogs as described in the present compositions and methods are useful, e.g., to treat diseases related to pancreatic function, including insulin and non-insulin related aspects. The present compositions and methods are useful to treat diabetes, diabetic ketoacidosis, or obesity, and to lower elevated or abnormal levels of cholesterol/LDL.

Thyronamine derivatives and analogs as described in the present compositions and methods are useful, e.g., to treat diseases related to renal failure or hepatic cirrhosis.

The present compositions and methods are useful to treat diabetes or obesity. Thyronamine derivatives and analogs play a role in the development and function of brown and white adipose tissue. Thyronamine derivatives and analogs can regulate factors of brown adipose tissue development to increase adaptive thermogenesis, e.g., to regulate basal oxygen consumption, fat stores, lipogenesis, and lipolysis.

Thyronamine derivatives and analogs as described in the present compositions and methods are useful, e.g., for modulation of thyroid metabolism and to treat diseases related to hyperthyroidism or hypothyroidism. The compositions and methods are useful for treatment of osteoporosis, the risk being increased by hyperthyroidism. The compositions and methods are useful for treatment and/or prevention of cretinism. The compositions and methods are useful to regulate hormone status and for physiological antagonism/ agonism at catecholamine receptors, e.g., receptors for dopamine, noradrenaline, adrenaline.

Thyronamine derivatives and analogs as described in the present compositions and methods are useful to treat subclinical thyroid dysfunction as it affects the heart and circulatory system of a mammalian subject. Subclinical hypothyroidism or subclinical hyperthyroidism can be a physiological effect of thyronamine derivatives and analogs whose activity is up regulated or down regulated within the heart or circulatory system of a mammalian subject. Agonists or antagonists of thyronamine derivatives and analogs are useful as therapeutic compositions to treat subclinical hypothyroidism or subclinical hyperthyroidism.

Subclinical hypothyroidism is associated with impaired left ventricular diastolic function at rest, systolic dysfunction on effort, and enhanced risk for atherosclerosis and myocardial infarction. Subclinical hyperthyroidism is associated with increased heart rate, atrial arrhythmias, increased left ventricular mass with marginal concentric remodeling, impaired ventricular relaxation, reduced exercise performance, and increased risk for cardiovascular death. See, e.g., Biondi, et al., *Ann Intern Med.*, 2002, 137: 904–914. Such abnormalities can be reversed by treatment with a therapeutic pharmaceutical composition of an agonist of a thyronamine derivative or analog (to treat subclinical hypothyroidism) or by treatment with a therapeutic pharmaceutical composition of an antagonist of a thyronamine derivative or analog (to treat subclinical hyperthyroidism).

Thyronamine derivatives and analogs can affect normal bone growth and development. In children, hypothyroidism can cause short stature and delayed closure of the epiphyses. Thyronamine derivatives and analogs can affect the expression of various bone markers in serum, reflecting changes in both bone formation and resorption. Both osteoblast and osteoclast activities can be stimulated by thyronamine derivatives and analogs. Indeed, there is enhanced calcification and bone formation coupled to increased bone resorption in hyperthyroid patients. Additionally, the time interval between formation and subsequent mineralization of osteoid is shortened. The net effect on these bone cells is bone resorption and loss of trabecular bone thickness in hyperthyroidism. There also is marked increase in porosity and decreased cortical thickness in cortical bone in hyperthyroid patients. These effects can lead to osteoporosis and increased fractures. Thyronamine derivatives and analogs as described in the present compositions and methods are useful to treat osteoporosis and reverse the effects of bone loss.

Thyronamine derivatives and analogs as described in the present compositions and methods are useful, e.g., to treat psychological or psychophysiological disorders, for example, modulation of feeding behavior, starvation, eating disorders, anxiety, insomnia, migraine, and sleeping disorders. The present compositions and methods are useful to treat, for example, seizure, epilepsy, bipolar disorder, depression, attention deficit/hyperactivity disorder, and schizophrenia.

The present compositions and methods are useful, e.g., to enhance sedation or to treat cognition enhancement; memory enhancement, antiagression, antipsychotic, antispasmodic, antitremor, antidepressive, insomnia, seasonal affective disorder, augmentation or dampening of tricyclic antidepressant action, antiepileptic/antiseizure, mood modifier or enhancer, and psychological dissociative disorder.

The present compositions and methods are useful, e.g., to treat gastro esophogeal reflux disease (GERD), anti-diarrheal, and other diseases involving GI motility, for treatment of asthma, use as an antihistamine and for treatment of malignant disease related to uncontrolled cell growth and division as well as increased vascularization of the tumor.

Detection of Thyronamine Derivatives and Analogs

Thyronamine derivatives and analogs can be detected and quantified by any of a number of means well known to those of skill in the art. These include analytic biochemical methods such as electrophoresis, capillary electrophoresis, high performance liquid chromatography (HPLC), mass spectrometry, thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In one embodiment, thyronamine derivatives and analogs are detected using an immunoassay such as an ELISA assay (see, e.g., Crowther, John R. *ELISA Theory and Practice*. Humana Press: New Jersey, 1995). An "immunoassay" is an assay that utilizes an antibody to specifically bind to an thyronamine derivatives and analogs.

Antibodies to Thyronamine Derivatives and Analogs

Polyclonal antibodies, monoclonal antibodies, chimeric antibodies or humanized antibodies that react specifically to thyronamine derivatives and analogs, e.g., 3-iodothyronamine ($T_1AM$) is useful for determining the presence of thyronamine derivatives and analogs in primary cells and immortalized cell lines in vitro, as well as in vivo, in tissues and in biological fluids, for example, by radioimmunoassay and by immunocytochemistry.

Methods of producing polyclonal and monoclonal antibodies that react specifically with thyronamine derivatives and analogs are known to those of skill in the art (see, e.g., Coligan, *Current Protocols in Immunology* (1991); Harlow and Lane, *Antibodies: A Laboratory Manual*, Cold Spring Harbor Laboratory, 1988; Goding, *Monoclonal Antibodies: Principles and Practice* (2d ed. 1986); and Kohler & Milstein, *Nature* 256: 495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246: 1275–1281 (1989); Ward et al., *Nature* 341: 544–546 (1989)). Such antibodies can be used for therapeutic and diagnostic applications, e.g., in the treatment and/or detection of congestive heart failure.

A number of thyronamine derivatives and analogs, e.g., 3-iodothyronamine ($T_1AM$), 3,3'-diiodothyronamine (3,3'-$T_2AM$), 3,5-diiodothyronamine ($T_2AM$), or 3, 5, 3'-triiodothyronamine ($T_3AM$), can be used to produce antibodies specifically reactive with iodothyronamines. Synthetic or naturally occurring thyronamine derivatives and analogs can be used either in pure or impure form. The product is then injected into an animal capable of producing antibodies. Either monoclonal or polyclonal antibodies can be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to thyronamine derivatives and analogs. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies can be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6: 511–519, 1976). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells can be enhanced by various techniques, including injection into the peritoneal cavity of a vertebrate host. Alternatively, one can isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen in an immunoassay, for example, a solid phase immunoassay with the immunogen immobilized on a solid support. Typically, polyclonal antisera with a titer of $10^4$ or greater are selected and tested for their cross reactivity against other amines or even other related amines from other organisms, using a competitive binding immunoassay. Specific polyclonal antisera and monoclonal antibodies will usually bind with a $K_d$ of at least about 0.1 mM, more usually at least about 1 $\mu$M, preferably at least about 0.1 $\mu$M or better, and most preferably, 0.01 $\mu$M or better.

Once specific antibodies to thyronamine derivatives and analogs are available, iodo-thyronamine can be detected by a variety of immunoassay methods. For a review of immunological and immunoassay procedures, see *Basic and Clinical Immunology* (Stites & Terr eds., 7th ed. 1991). Moreover, the immunoassays as described herein can be performed in any of several configurations, which are reviewed extensively in *Enzyme Immunoassay* (Maggio, ed., 1980); and Harlow & Lane, supra.

Chimeric and Humanized Antibodies

Chimeric and humanized antibodies have the same or similar binding specificity and affinity as a mouse or other nonhuman antibody that provides the starting material for construction of a chimeric or humanized antibody. Some chimeric or humanized antibodies have affinities within a factor of 2-fold, 5-fold or 10-fold that of a mouse. Chimeric antibodies are antibodies whose light and heavy chain genes have been constructed, typically by genetic engineering, from immunoglobulin gene segments belonging to different species. For example, the variable (V) segments of the genes from a mouse monoclonal antibody can be joined to human constant (C) segments, such as $IgG_1$, $IgG_2$, $IgG_3$ and $IgG_4$. A typical chimeric antibody is thus a hybrid protein consisting of the V or antigen-binding domain from a mouse antibody and the C or effector domain from a human antibody.

Humanized antibodies have variable region framework residues substantially from a human antibody (termed an acceptor antibody) and complementarity determining regions substantially from a nonhuman antibody such as a mouse-antibody, (referred to as the donor immunoglobulin). See Queen et al., *Proc. Natl. Acad. Sci. USA* 86:10029–33, 1989, and WO 90/07861, U.S. Pat. Nos. 5,693,762, 5,693,761, 5,585,089, 5,530,101 and Winter, U.S. Pat. No. 5,225,539, each of which is herein incorporated by reference in its entirety for all purposes. The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653, incorporated herein by reference. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid: (1) noncovalently binds antigen directly, (2) is adjacent to a CDR region, (3) otherwise interacts with a CDR region (e.g. is within about 6A of a CDR region), or (4) participates in the $V_L$–$V_H$ interface.

Other candidates for substitution are acceptor human framework amino acids that are unusual for a human immunoglobulin at that position. These amino acids can be substituted with amino acids from the equivalent position of the donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

Human antibodies against thyronamine derivatives and analogs can be generated by a variety of techniques. Some human antibodies are selected by competitive binding experiments, or otherwise, to have the same epitope specificity as a particular mouse antibody. Human antibodies can also be screened for a particular epitope specificity by using only a fragment of thyronamine derivative and analog as the immunogen. One technique is the trioma methodology which can utilize an exemplary cell fusion partner, SPAZ-4, for use in this approach have been described by Oestberg et al., Hybridoma 2: 361–67, 1983; Oestberg, U.S. Pat. No. 4,634,664; and Engleman et al., U.S. Pat No. 4,634,666, each of which is incorporated by reference in their entirety for all purposes. In a second technique human antibodies against thyronamine derivatives and analogs can also be produced from non-human transgenic mammals having transgenes encoding at least a segment of the human immunoglobulin locus as discussed. Usually, the endogenous immunoglobulin locus of such transgenic mammals is functionally inactivated. Preferably, the segment of the human immunoglobulin locus includes unrearranged sequences of heavy and light chain components. A further approach for obtaining human anti-thyronamine derivatives and analogs is to screen a DNA library from human B cells according to the general protocol outlined by Huse et al., *Science* 246: 1275–81, 1989, incorporated herein by reference. The protocol described by Huse is rendered more efficient in combination with phage-display technology. See, e.g., Dower et al., WO 91/17271 and McCafferty et al. WO 92/01047, U.S. Pat. Nos. 5,877,218, 5,871,907, 5,858,657, 5,837,242, 5,733,743 and 5,565,332, 5,969,108, 6,172,197 (each of which is incorporated by reference in its entirety for all purposes). Additional methods for selecting and labeling antibodies, or other proteins, that bind to a particular ligand are described by U.S. Pat. Nos. 5,994,519 and 6,180,336, each incorporated herein by reference. The heavy and light chain variable regions of chimeric, humanized, or human antibodies can be linked to at least a portion of a human constant region. The choice of constant region depends, in part, whether antibody-dependent complement and/or cellular mediated toxicity is desired. Chimeric, humanized and human antibodies are typically produced by recombinant expression. Recombinant polynucleotide constructs typically include an expression control sequence operably linked to the coding sequences of antibody chains, including naturally-associated or heterologous promoter regions.

Immunological Binding Assays

Thyronamine derivatives and analogs can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991).

Immunoassays typically use direct or indirect labeling agents to label the complex formed by the antibody and antigen. The labeling agent can itself be one of the moieties comprising the antibody/antigen complex, i.e., a direct labeling agent. Thus, the labeling agent can be a labeled thyronamine derivative and analog or a labeled anti-iodothyronamine antibody. Alternatively, the labeling agent can be a third moiety, such as a secondary antibody, that specifically binds to the antibody/iodo-thyronamine complex (a secondary antibody is typically specific to antibodies of the species from which the first antibody is derived). Other proteins capable of specifically binding immunoglobulin constant regions, such as protein A or protein G can also be used as the label agent. These proteins exhibit a strong non-immunogenic reactivity with immunoglobulin constant regions from a variety of species (see, e.g., Kronval et al., *J. Immunol.* 111: 1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non competitive assay formats: Immunoassays for detecting thyronamine derivatives and analogs in samples can be either competitive or noncompetitive. Noncompetitive immunoassays are assays in which the amount of antigen is directly measured. In one preferred "sandwich" assay, for example, anti-iodo-thyronamine antibodies can be bound directly to a solid substrate on which they are immobilized. These immobilized antibodies then capture thyronamine derivatives and analogs present in the test sample. The iodo-thyronamine thus immobilized is then bound by a labeling agent, such as a second iodo-thyronamine antibody bearing a label. Alternatively, the second antibody can lack a label, but it can, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive assay formats: In competitive assays, the amount of thyronamine derivative and analog present in a sample is measured indirectly, e.g., by measuring the amount of added (exogenous) iodo-thyronamine displaced (or competed away) from an anti-iodothyronamine antibody by iodo-thyronamines present in a sample. For example, a known amount of labeled iodo-thyronamine is added to a sample and the sample is then contacted with an anti-iodothyronamine antibody. The amount of labeled iodo-thyronamine bound to the antibody is inversely proportional to the concentration of iodo-thyronamine present in the sample. In one embodiment, the antibody is immobilized on a solid substrate. The amount of iodo-thyronamine bound to the antibody can be determined either by measuring the amount of iodo-thyronamine present in a iodo-thyronamine/antibody complex, or alternatively by measuring the amount of remaining uncomplexed iodo-thyronamine. The amount of iodo-thyronamine can be detected by providing a labeled iodo-thyronamine molecule.

A hapten inhibition assay is another competitive assay. The hapten is generally conjugated to a carrier protein, for example, KLH or BSA. In this assay the known thyronamine derivative or analog is immobilized on a solid substrate. A known amount of anti-iodothyronamine antibody is added to the sample, and the sample is then contacted with the immobilized iodo-thyronamine. The amount of anti-iodothyronamine antibody bound to the known immobilized iodo-thyronamine is inversely proportional to the amount of iodo-thyronamines present in the sample. Again, the amount of immobilized antibody can be detected by detecting either the immobilized fraction of antibody or the fraction of the antibody that remains in solution. Detection can be direct where the antibody is labeled or indirect by the subsequent addition of a labeled moiety that specifically binds to the antibody as described above.

Other assay formats: Liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of non-specific binding: One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels for detection: The particular label or detectable group used in the assay is not a critical aspect, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied. Thus, a label is any composition detectable by spectroscopic, photochemical, biochemical, immunochemical, electrical, optical or chemical means. Useful labels include magnetic beads (e.g., DYNABEADS™), fluorescent dyes (e.g., fluorescein isothiocyanate, Texas red, rhodamine, and the like), radio-labels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic beads (e.g., polystyrene, polypropylene, latex, etc.).

The label can be coupled directly or indirectly to the desired component of the assay according to methods well known in the art. As indicated above, a wide variety of labels can be used, with the choice of label depending on sensitivity required, ease of conjugation with the compound, stability requirements, available instrumentation, and disposal provisions. For a review of various labeling or signal producing systems that can be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels can be detected by providing the appropriate substrates for the enzyme and detecting the resulting reaction product. Finally simple calorimetric labels can be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Pharmaceutical Compositions

Thyronamine derivatives and analogs useful in the present compositions and methods can be administered to a human patient per se, in the form of a stereoisomer, prodrug, pharmaceutically acceptable salt, hydrate, solvate, acid salt hydrate, N-oxide or isomorphic crystalline form thereof, or in the form of a pharmaceutical composition where the compound is mixed with suitable carriers or excipient(s) in a therapeutically effective amount, for example, heart disease or congestive heart failure.

Routes of Administration

The thyronamine derivatives and analogs and pharmaceutical compositions described herein can be administered by a variety of routes. Suitable routes of administration can, for example, include oral, rectal, transmucosal, or intestinal administration; parenteral delivery, including intramuscular, subcutaneous, intramedullary injections, as well as intrathecal, direct intraventricular, intravenous, intraperitoneal, spinal, epidural, intranasal, or intraocular injections. Alternatively, one can administer the compound in a local rather than systemic manner, for example via injection of the compound directly into the subject, often in a depot or sustained release formulation. Furthermore, one can administer the compound in a targeted drug delivery system, for example, in a liposome coated vesicle. The liposomes can be targeted to and taken up selectively by the tissue of choice. In a further embodiment, the thyronamine derivatives and analogs and pharmaceutical compositions described herein are administered orally.

Composition/Formulation

The pharmaceutical compositions described herein can be manufactured in a manner that is itself known, e.g., by means of conventional mixing, dissolving, granulating, dragee-making, levigating, emulsifying, encapsulating, entrapping or lyophilizing processes. Pharmaceutical compositions for use as described herein can be formulated in conventional manner using one or more physiologically acceptable carriers comprising excipients and auxiliaries which facilitate processing of the active compounds into preparations which can be used pharmaceutically. Proper formulation is dependent upon the route of administration chosen. For injection, the agents can be formulated in aqueous solutions, e.g., in physiologically compatible buffers such as Hanks' solution, Ringer's solution, or physiological saline buffer. For transmucosal administration, penetrants appropriate to the barrier to be permeated are used in the formulation. Such penetrants are generally known in the art. For oral administration, the compounds can be formulated readily by combining with pharmaceutically acceptable carriers that are well known in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores.

Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner. For administration by inhalation, the compounds for use are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides. In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

A suitable pharmaceutical carrier for hydrophobic compounds is a cosolvent system comprising benzyl alcohol, a nonpolar surfactant, a water-miscible organic polymer, and an aqueous phase. The cosolvent system can be the VPD co-solvent system. VPD is a solution of 3% (w/v) benzyl alcohol, 8% (w/v) of the nonpolar surfactant polysorbate 80, and 65% (w/v) polyethylene glycol 300, made up to volume in absolute ethanol. The VPD co-solvent system (VPD:5W) consists of VPD diluted 1:1 with a 5% (w/v) dextrose in water solution. This cosolvent system dissolves hydrophobic compounds well, and itself produces low toxicity upon systemic administration. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can substitute for dextrose. Alternatively, other delivery systems for hydrophobic pharmaceutical compounds can be employed. Liposomes and emulsions are well known examples of delivery vehicles or carriers for hydrophobic drugs. Certain organic solvents such as dimethylsulfoxide also can be employed, although usually at the cost of greater toxicity.

Additionally, the compounds can be delivered using a sustained-release system, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few weeks up to over 100 days. The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutically acceptable carriers are determined in part by the particular composition being administered, as well as by the particular method used to administer the composition. Accordingly, there is a wide variety of suitable formulations of pharmaceutical compositions for administering the iodo-thyronamine (see, e.g., *Remington's Pharmaceutical Sciences*, Mack Publishing Co., Easton, Pa. 18$^{th}$ ed., 1990, incorporated herein by reference). The pharmaceutical compositions generally comprise a differentially expressed protein, agonist or antagonist in a form suitable for administration to a patient. The pharmaceutical compositions are generally formulated as sterile, substantially isotonic and in full compliance with all Good Manufacturing Practice (GMP) regulations of the U.S. Food and Drug Administration.

Effective Dosages

Pharmaceutical compositions suitable for use include compositions wherein the thyronamine derivatives and analogs are contained in a therapeutically effective amount. Determination of an effective amount is well within the capability of those skilled in the art, especially in light of the detailed disclosure provided herein. For any compound used in the present method, a therapeutically effective dose can be estimated initially from cell culture assays. For example, a dose can be formulated in animal models to achieve a circulating concentration range that includes the I50 as determined in cell culture (i.e., the concentration of test compound that is lethal to 50% of a cell culture) or the $I_{100}$ as determined in cell culture (i.e., the concentration of compound that is lethal to 100% of a cell culture). Such information can be used to more accurately determine useful doses in humans. Initial dosages can also be formulated by comparing the effectiveness of the thyronamine derivatives and analogs described herein in cell culture assays with the effectiveness of known heart medications. In this method an initial dosage can be obtained by multiplying the ratio of effective concentrations obtained in cell culture assay for the thyronamine derivatives and analogs and a known heart drug by the effective dosage of the known heart drug. For example, if an thyronamine derivative or analog is twice as effective in cell culture assay than the heart drug (i.e., the $I_{50}$ $T_1$amine is equal to one half times the $I_{50}$ heart drug in the same assay), an initial effective dosage of the thyronamine derivative or analog would be one-half the known dosage for the heart drug. Using these initial guidelines one having ordinary skill in the art could determine an effective dosage in humans. Initial dosages can also be estimated from in vivo data. One having ordinary skill in the art could readily optimize administration to humans based on this data. Dosage amount and interval can be adjusted individually to provide plasma levels of the active compound which are sufficient to maintain therapeutic effect. Usual patient dosages for oral administration range from about 50–2000 mg/kg/day, typically from about 250–1000 mg/kg/day, from about 500–700 mg/kg/day or from about 350–550 mg/kg/day. Therapeutically effective serum levels will be achieved by administering multiple doses each day. In cases of local administration or selective uptake, the effective local concentration of the drug can not be related to plasma concentration. One having skill in the art will be able to optimize therapeutically effective local dosages without undue experimentation. The amount of composition administered will, of course, be dependent on the subject being treated, on the subject's weight, the severity of the affliction, the manner of administration and the judgment of the prescribing physician. The therapy can be repeated intermittently while congestive heart failure is detectable or even when they are not detectable. Moreover, due to its apparent nontoxicity, the therapy can be provided alone or in combination with other drugs, such as for example, anti-inflammatories, antibiotics, corticosteroids, vitamins and the like. Possible synergism between the thyronamine derivatives or analogs described herein and other drugs can occur. In addition, possible synergism between a plurality of thyronamine derivatives or analogs can occur.

The typical daily dose of a pharmaceutical composition of thyronamine derivatives and analogs varies according to individual needs, the condition to be treated and with the route of administration. Suitable doses are in the general range of from 0.001 to 10 mg/kg bodyweight of the recipient per day. Within this general dosage range, doses can be chosen at which the pharmaceutical composition of thyronamine derivatives and analogs has an inotropic effect to increase cardiac output without the chronotropic effect to increase heart rate. In general, but not exclusively, such doses will be in the range of from 0.5 to 10 mg/kg.

In addition, within the general dose range, doses can be chosen at which the compounds pharmaceutical composition of thyronamine derivatives and analogs has an inotropic effect to increase cardiac output without the chronotropic effect to increase heart rate. In general, but not exclusively, such doses will be in the range of from 0.001 to 0.5 mg/kg. It is to be understood that the 2 sub ranges noted above are not mutually exclusive and that the particular activity encountered at a particular dose will depend on the nature of the pharmaceutical composition of thyronamine derivatives and analogs used.

The pharmaceutical composition of thyronamine derivatives and analogs can be in unit dosage form, for example, a tablet or a capsule so that the patient can self-administer a single dose. In general, unit doses contain in the range of from 0.05-100 mg of a compound of the pharmaceutical composition of thyronamine derivatives and analogs. Unit doses contain from 0.05 to 10 mg of the pharmaceutical composition. The active ingredient can be administered from 1 to 6 times a day. Thus daily doses are in general in the range of from 0.05 to 600 mg per day. In an embodiment, daily doses are in the range of from 0.05 to 100 mg per day or from 0.05 to 5 mg per day.

Toxicity

Toxicity and therapeutic efficacy of the thyronamine derivatives and analogs described herein can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$ Compounds which exhibit high therapeutic indices are chosen. The data obtained from these cell culture assays and animal studies can be used in formulating a dosage range that is not toxic for use in human. The dosage of such compounds lies within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch. 1, p.1). One of the advantages, among others, of using the thyronamine derivatives and analogs described herein to treat congestive heart failure is their lack of toxicity. For example, it has been found that repeated intraperitoneal doses of 75 mg/kg produced no ill effects in mice (see Example 5). Since the i.v. serum half-life ($t_{1/2}$) of $T_1$amine is about 2–2.5 hours, repeated daily dosages of the iodo-thyronamine described herein without ill effects is predictable.

Methods of Preparation

The thyronamine derivatives and analogs can be prepared from the copper mediated coupling of a boronic acid or analog and the appropriate protected phenol as shown in Schemes 1–3. Variations in $R_6$ can be made by utilizing the appropriately protected boronic acid.

Scheme 1: Preparation of Protected Tyramines

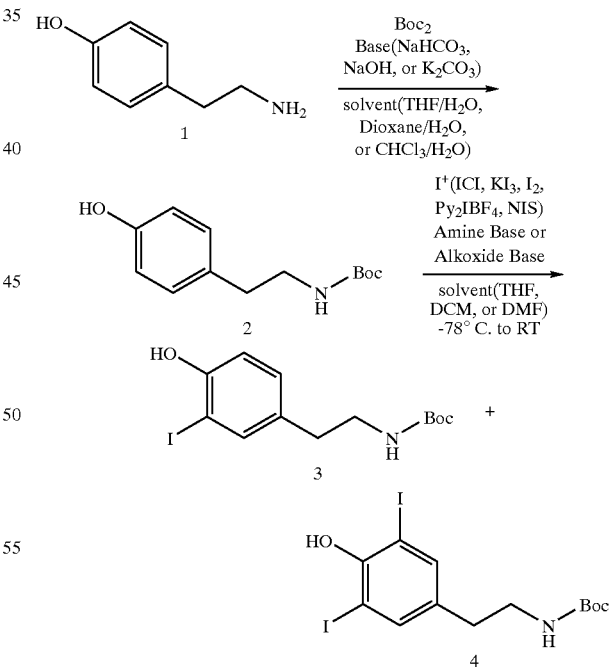

In Scheme 1, the appropriate amine-protected iodine-substituted tyramines 3 and 4 are prepared by first protecting the amino functionality of the tyramine 1 to form the protected tyramine 2 and then substituting one or more of the hydrogens (at the 3-position, 5position or both) on the phenyl with iodine to form compounds 3 and 4. Other substitutions can also be made in an analogous fashion known to those skilled in the art. The amino functionality of the tyramine is protected using a protecting group in the presence of base, such as NaHCO$_3$, NaOH, or K$_2$CO$_3$, and solvent, such as THF/H$_2$O, dioxane/H$_2$O or CHCl$_3$/H$_2$O. Suitable amine-protecting groups commonly used in the art can be found in Greene and Wuts, *Protective Groups in Organic Synthesis,* 2d ed, John Wiley & Sons, New York, 1991, the disclosure of which is hereby incorporated by reference in its entirety. Suitable protecting groups include but are not limited to, allyloxycarbonyl (Aloc), benzyloxycarbonyl (Cbz), ethoxycarbonyl, 9-fluorenylmethoxycarbonyl (Fmoc), and tert-butoxycarbonyl (t-Boc). The t-Boc is a preferred protecting group. The hydrogens on the phenyl group at 3-position, 5-position or both are substituted with iodine by employing electrophilic iodine reagents, for example, iodine monochloride (ICl), a solution of potassium iodide and iodine (KI$_3$), iodine (I$_2$), bispyridinium iodine tetrafluoroborate (Py$_2$IBF$_4$), N-iodosuccinimide (NIS) and the like, in the presence of base, such as amine base or alkoxide base. These conditions form a mixture of the appropriate amine-protected iodine-substituted tyramines 3 and 4 which can be separated by column chromatography.

Scheme 2: Preparation of Boronic Acid

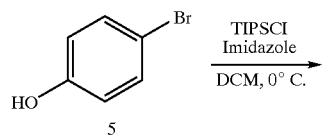

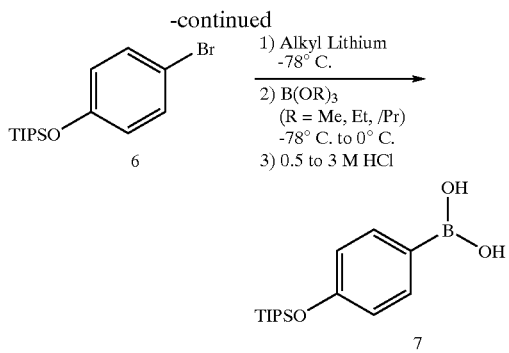

In Scheme 2, the appropriate phenylboronic acid 7 is prepared from the commercially available p-bromophenol 5 starting material. Phenol 5 is first protected with a hydroxyl protecting group, such as triisopropylsilyl chloride (TIPS), to form compound 6, which is subsequently reacted with alkyl lithium, B(OR)$_3$ (where R is methyl, ethyl, or isopropyl), then hydrolyzed to form compound 7. Suitable hydroxyl-protecting groups commonly used in the art can be found in Greene and Wuts, Protective Groups in Organic Synthesis, 2d ed, John Wiley & Sons, New York, 1991, the disclosure of which is hereby incorporated by reference in its entirety. Suitable protecting groups include but are not limited to triethylsilyl (TES), tert-butyldimethylsilyl (TBDMS), and triisopropylsilyl (TIPS). TIPSO is a preferred protecting group.

Scheme 3: Synthesis of Thyronamines

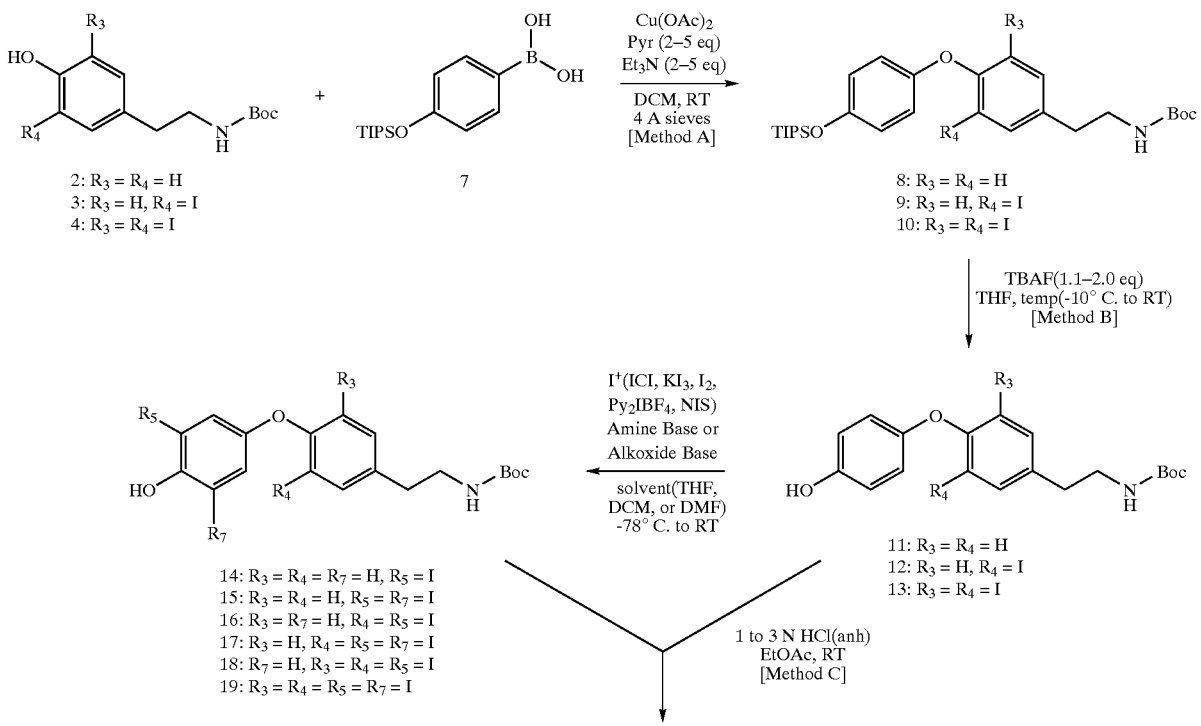

-continued

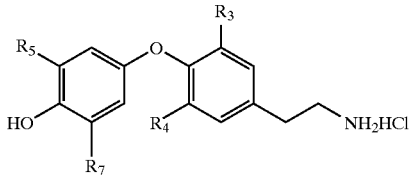

22: R₃ = R₄ = R₅ = R₇ = H
23: R₃ = R₅ = R₇ = H, R₄ = I
24: R₅ = R₇ = H, R₃ = R₄ = I
25: R₃ = R₄ = R₇ = H, R₅ = H
26: R₃ = R₄ = H, R₅ = R₇ = I
27: R₃ = R₇ = H, R₄ = R₅ = I
28: R₃ = H, R₄ = R₅ = R₇ = I
29: R₇ = H, R₃ = R₄ = R₅ = I
30: R₃ = R₄ = R₅ = R₇ = I where

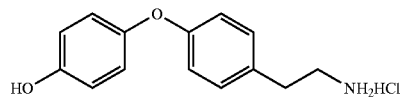

22

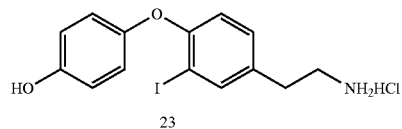

23

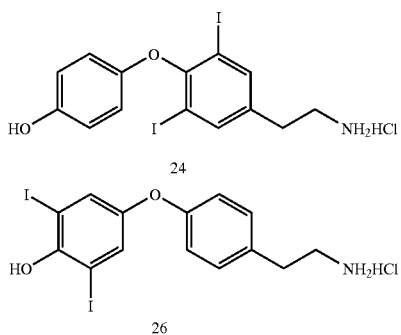

24

26

28

30

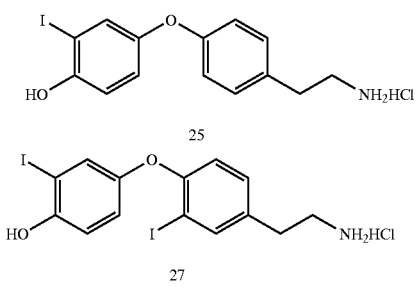

25

27

29

In Scheme 3, compound 7 prepared in Scheme 2 and the amine-protected iodine-substituted tyramine (compound 3 or 4) prepared in Scheme 1 are coupled in the presence of copper to give the thyronamine core. In subsequent steps, the hydroxyl-protecting group and the amino-protecting group are removed. Alternatively, Iodo substitutions can be made at the 3' position, 5'-position or both the 3'- and 5'-positions prior to amine deprotection. Other substitutions at the 3, 3', 5 and 5' positions, such as fluoro, methy, ethyl and nitrile, can be made by using electrophilic bromide and chloride or by using an appropriately substituted boronic acid of type 7 or protected amine of type 2.

Compounds with other changes at the X position, such as CH₂, S, and NH, can also be made. In particular, halogenation followed by formylation of phenol 2 and subsequent treatment with the alkyl lithium of 6 will give compounds of the general formula X is equal to CH₂ after catalytic hydrogenation. Nucleophilic addition of the appropriate thiophenol to compound 6 will give compounds of the general formula where X is S. Additionally, a palldium-mediated coupling can be used to synthesis compounds of the general formula where X is NH.

Description of Scheme 4

Compounds of the general formula where $R_6$ is H and X is O can be prepared by reacting the protected thyronamine 2 with phenyl boronic acid to give 20, as shown in Scheme 4. The coupling reaction utilizes a copper(II) salt and suitable amine bases such as pyridine and triethylamine. Anhydrous polar aprotic solvents are typically used, such as DCM. Temperatures can range from 0° C. to 50° C. The amine protecting group is then removed using standard deprotection conditions.

Scheme 4: Synthesis of Phenyl Derivative

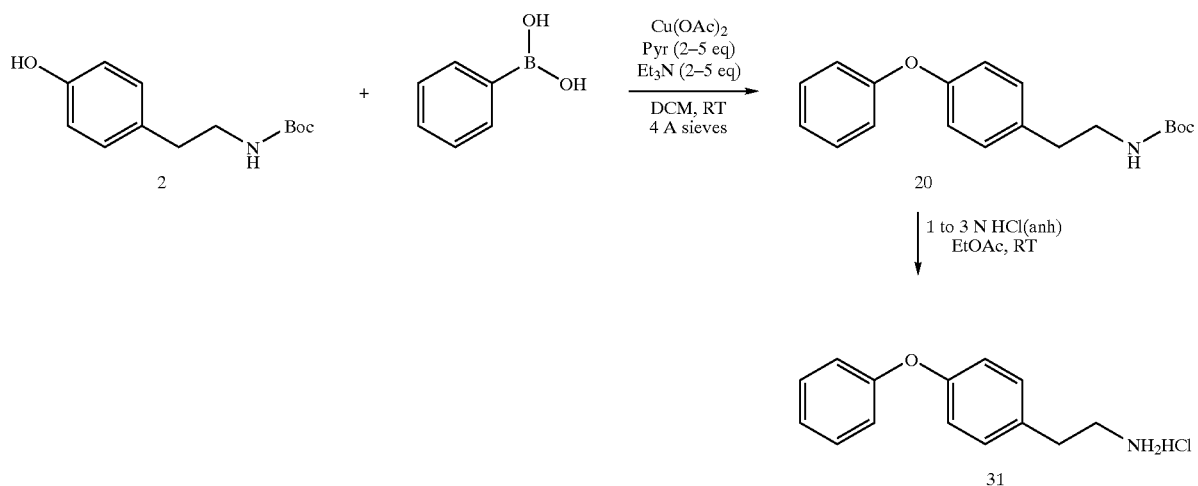

Description of Scheme 5

Compounds of the general formula where $R_6$ is H and X is $CH_2O$ or $CH_2CH_2O$ can be prepared by reacting the protected tyramine 2 with benzyl and alkyl halides, as shown in Scheme 5. The amine protecting group of the alkylated products can subsequently be deprotected using standard deprotection conditions. The alkylations can be done in a variety of polar aprotic solvents including, but not limited to, dimethylformamide (DMF), tetrahydrofuran (THF), acetone, diethyl ether, and dimethyl sulfoxide (DMSO). Temperatures can range from 0° C. to reflux. Typically, DMF at ambient temperature is sufficient.

Scheme 5: Synthesis of O-Alkylated Tyramine Derivatives

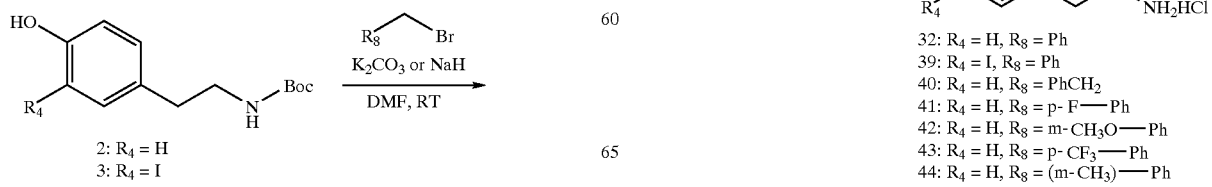

2: $R_4$ = H
3: $R_4$ = I

-continued

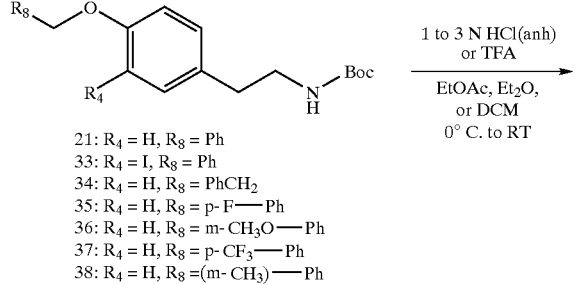

21: $R_4$ = H, $R_8$ = Ph
33: $R_4$ = I, $R_8$ = Ph
34: $R_4$ = H, $R_8$ = PhCH$_2$
35: $R_4$ = H, $R_8$ = p-F—Ph
36: $R_4$ = H, $R_8$ = m-CH$_3$O—Ph
37: $R_4$ = H, $R_8$ = p-CF$_3$—Ph
38: $R_4$ = H, $R_8$ =(m-CH$_3$)—Ph 1 to 3 N HCl(anh) or TFA
EtOAc, Et$_2$O, or DCM
0° C. to RT 32: $R_4$ = H, $R_8$ = Ph
39: $R_4$ = I, $R_8$ = Ph
40: $R_4$ = H, $R_8$ = PhCH$_2$
41: $R_4$ = H, $R_8$ = p-F—Ph
42: $R_4$ = H, $R_8$ = m-CH$_3$O—Ph
43: $R_4$ = H, $R_8$ = p-CF$_3$—Ph
44: $R_4$ = H, $R_8$ = (m-CH$_3$)—Ph -continued
where
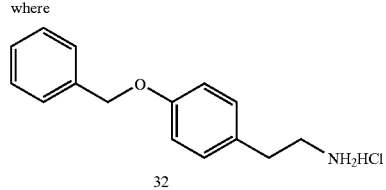
32
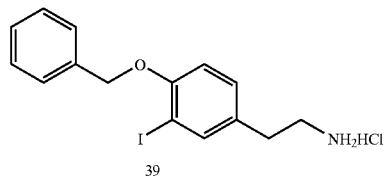
39
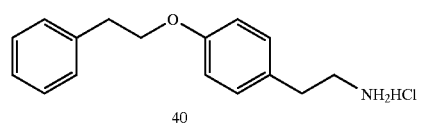
40
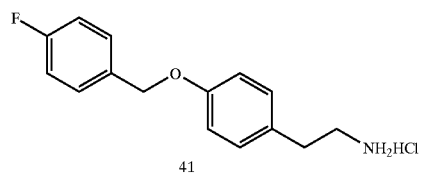
41
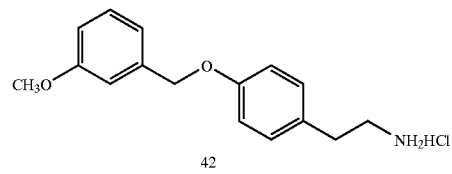
42
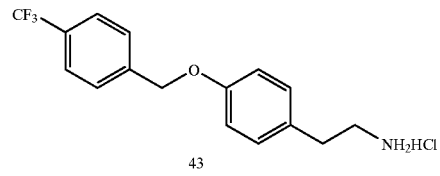
43
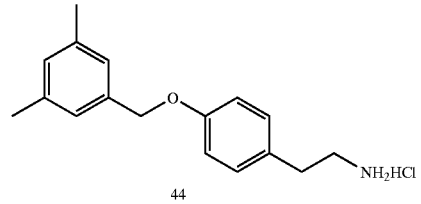
44
Scheme 6: Synthesis of N-Alkylated Derivatives
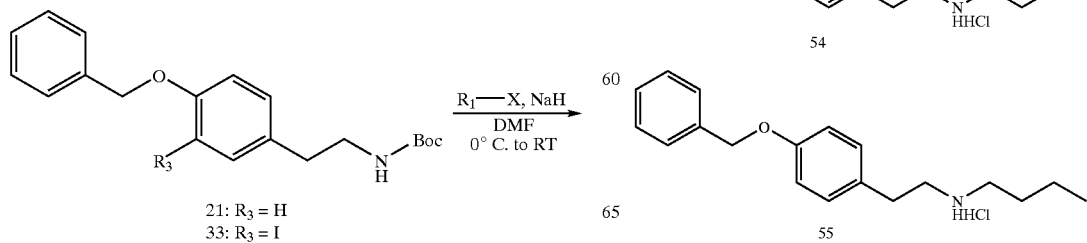
21: R₃ = H
33: R₃ = I
-continued
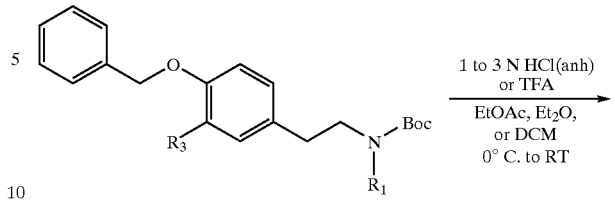
45: R₃ = H, R₁ = Me
46: R₃ = I, R₁ = Me
47: R₃ = H, R₁ = Et
48: R₃ = H, R₁ = Pr
49: R₃ = H, R₁ = Bu
50: R₃ = H, R₁ = Bn
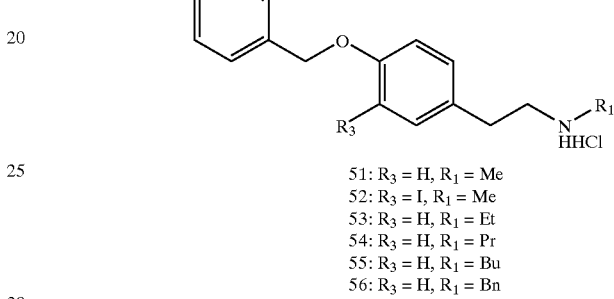
51: R₃ = H, R₁ = Me
52: R₃ = I, R₁ = Me
53: R₃ = H, R₁ = Et
54: R₃ = H, R₁ = Pr
55: R₃ = H, R₁ = Bu
56: R₃ = H, R₁ = Bn
where
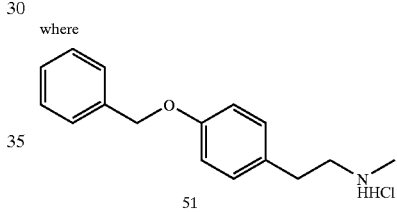
51
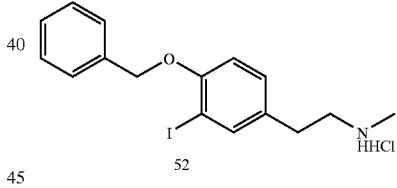
52
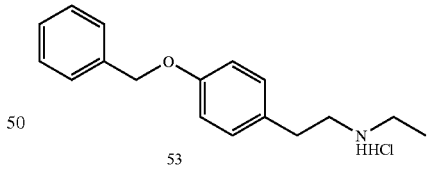
53
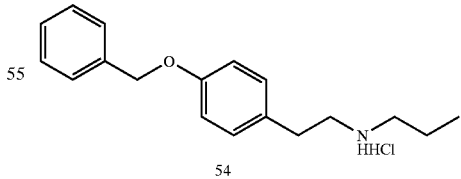
54
55

-continued

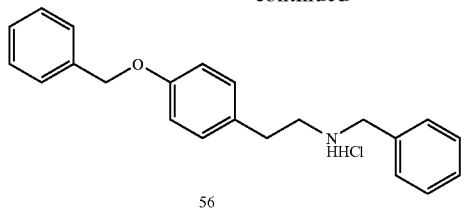

56

Description of Scheme 6

Compounds where R₁ is lower alkyl or benzyl can be synthesized as described in Scheme 6. The appropriately protected derivates of type 21 can be N-alkylated utilizing a strong base such as sodium hydride and the necessary alkyl in a suitable polar aprotic solvent such as DMF or DMSO. Temperatures range from 0° C. to 50° C. The amine protecting group of the alkylated products are subsequently removed under standard deprotection conditions.

In connection with the preparation of thyronamine derivatives and analogs, the methods can offer improved yields, purity, ease of preparation and/or isolation of intermediates and final product, and more industrially useful reaction conditions and workability over prior art methods of preparation. The present methods are particularly useful for the preparation of thyronamine derivatives and analogs on a large scale, including commercial scale, for example, from multi-kilogram to ton quantities or more of thyronamine derivative or analog. Specifically, isolation and/or purification steps of intermediates to the thyronamine derivatives and analogs can be advantageously substantially or completely avoided using the present methods. The present methods can be particularly advantageous in that the thyronamine derivatives and analogs can be obtained in substantially pure form. The term "substantially pure form", as used herein, means that the thyronamine derivative or analog prepared using the present processes can preferably be substantially devoid of organic impurities. The term "organic impurities", as used herein, refers to organic materials, compounds, etc., other than the desired product, that can be typically associated with synthetic organic chemical transformations including, for example, unreacted starting reagents, unreacted intermediate compounds, and the like. In preferred form, the present processes can provide thyronamine compounds that are at least about 75% pure, as measured by standard analytical techniques such as, for example, HPLC. Preferably, the thyronamine derivatives and analogs prepared using the present methods can be at least about 80% pure, with a purity of at least about 85% being more preferred. Even more preferably, the thyronamine derivatives and analogs prepared using the present methods can be at least about 90% pure, with a purity of at least about 95% being more preferred. In particularly preferred embodiments, the thyronamine derivatives and analogs prepared using the present methods can be more than about 95% pure, with a purity of about 99.8% being even more preferred, and with a purity of about 100% being especially preferred.

Alternatively, if a salt of the thyronamine derivative or analog is desired, a suitable acid can be added followed by cooling and seeding of the resultant solution to provide the crystalline salt. Preferably, the acid chosen will be able to form the salt without affecting the integrity of the target compound. Thus, mild acids, such as sulfonic acids, are preferred. In particular, methane sulfonic acid, benzenesulfonic acid, toluenesulfonic acid, hydroxyethanesulfonic acid, camphorsulfonic acid, and other sulfonic acids can prepare suitable crystalline salts. A particularly preferred acid is methane sulfonic acid. It will be appreciated, however, that numerous other salts are possible, when an anhydrous form of the acid is available. For example, mineral acids, such as hydrochloric, hydrobromic, phosphoric, sulfuric, or nitric acid can prepare suitable crystalline salts. Other organic acids, such as fumaric, succinic, oxalic, citric, and the like, can prepare suitable crystalline salts provided that they are sufficiently acidic to protonate the basic moiety of the thyronamine compound.

Under appropriate conditions, however, other solvents can be used to prepare crystalline salts of thyronamine compound, such as ester solvents, including, but not limited to ethyl acetate, propyl acetate, isopropyl acetate, isobutyl acetate, ethyl propionate, propyl propionate, isopropyl propionate; ether solvents, including, but not limited to t-butyl methyl ether, tetrahydrofuran, ethyl ether, isopropyl ether, butyl ether; and aromatic solvents, including, but not limited to toluene and anisole. Other solvents will be readily understood to those of ordinary skill in the art. Filtration and washing of the product, preferably with additional crystallization solvent, affords the thyronamine compound.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present compositions and methods.

Certain acidic or basic compounds can exist as zwitterions. All forms of the compounds, including free acid, free base and zwitterions, are contemplated to be within the scope of the present compositions and methods. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

The reactions of the synthetic methods described and claimed herein can be carried out in suitable solvents which can be readily selected by one skilled in the art of organic synthesis. Generally, suitable solvents are solvents which are substantially non-reactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction, suitable solvents for a particular work-up following the reaction can be selected. Suitable solvents, as used herein can include, by way of example and without limitation, chlorinated solvents, hydrocarbon solvents, aromatic solvents, ether solvents, protic solvents, polar aprotic solvents, and mixtures thereof.

Suitable halogenated solvents include, but are not limited to carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable hydrocarbon solvents include, but are not limited to alkane or aromatic solvents such as cyclohexane, pentane, hexane, toluene, cycloheptane, methylcyclohexane, heptane, ethylbenzene, m-, o-, or p-xylene, octane, indane, nonane, benzene, ethylbenzene, and m-, o-, or p-xylene.

Suitable ether solvents include, but are not limited to dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol diisopropyl ether, anisole, or t-butyl methyl ether.

Suitable protic solvents include, but are not limited to water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, 1-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, and glycerol.

Suitable aprotic solvents include, but are not limited to dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile (ACN), dimethylsulfoxide (DMSO), propionitrile, ethyl formate, methyl acetate, hexachloroacetone, acetone, ethyl methyl ketone, ethyl acetate, isopropyl acetate, t-butyl acetate, sulfolane, N,N-dimethylpropionamide, nitromethane, nitrobenzene, and hexamethylphosphoramide.

The compositions and methods are further described in the following examples. All of the examples are actual examples. These examples are for illustrative purposes only, and are not to be construed as limiting the appended claims.

EXAMPLES

General: All reactions were conducted under inert argon passed through a Drierite drying tube in flame dried glassware unless otherwise noted. Anhydrous tetrahydrofuran (THF) was dried in a sodium benzophenone ketyl radical still. All other anhydrous solvents and reagents were purchased from Aldrich, Sigma-Aldrich, Fluka, or Acros and were used without any further purification unless otherwise stated. $^1$H and $^{13}$C NMR spectra were taken on a Varian 400 (400 MHz and 100 MHz respectively). Data reported are calibrated to internal TMS (0.0 ppm) for all solvents unless otherwise noted and are reported as follows: chemical shift, multiplicity (app=apparant, par obsc=partially obscured, ovrlp=overlapping, brd=broad, s=singlet, d=doublet, t=triplet, q=quartet, m=multiplet), coupling constant, and integration. High resolution mass spectra were obtained from the departmental mass spectrometry facility. Thin-layer chromatography (TLC) was performed on 0.25 mm Merck precoated silica gel plates and silica gel chromatography was performed using Silica Gel 60 Geduran (EM Science).

Example 1

Preparation of N-t-Boc-tyramine (2)

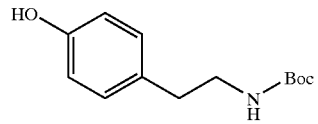

A solution of NaHCO$_3$ (10.7 g, 127 mmol) in water (250 ml) was added to a solution of tyramine (1) (15.8 g, 115 mmol) suspended in THF (500 ml) and vigorously stirred. After 24 hours the mixture was diluted with excess ether and the aqueous was extracted with ether (2x). The combined organic layers were sequentially washed with 0.5 M HCl, water, and brine then dried over MgSO$_4$. Concentration gave a crude yellow oil which was purified by flash SiO$_2$ chromatography (dry loaded, eluted with hexanes/ethyl acetate (3:1)) to give 2 as a white solid (24.7 g, 91% yield): $^1$H-NMR (400 MHz, chloroform-d) δ 6.99 (d, J=8.4 Hz, 2H), 6.78 (d, J=8.4 Hz, 2H), 4.67 (brd s, 1H), 4.47 (brd s, 1H), 3.32 (brd q, J=6.4 Hz, 2H), 2.69 (t, J= 6.8. Hz, 2H), 1.44 (s, 9H); $^{13}$C-NMR (100 MHz, chloroform-d) δ 156.3, 154.8, 130.2, 129.7, 115.5, 79.7, 42.0, 35.2, 28.4; HRMS (EI+) for C$_{13}$H$_{19}$NO$_3$ calcd. 237.1365 found 237.1367.

Example 2

Preparation of N-t-Boc-3-iodotyramine (3) and N-t-Boc-3,5-diiodotyramine (4)

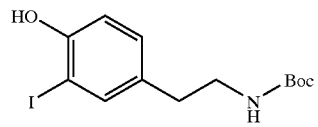

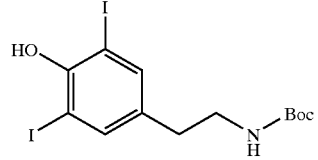

The N-t-Boc-tyramine 2 (15.0 g, 63.3 mmol) was dissolved in DCM (250 ml) and DMF (60 ml). The resulting solution was cooled to −40° C. and sodium methoxide (6.84 g, 127 mmol) was added in one portion. Iodine monochloride (100 ml, 100 mmol) was added to the reaction dropwise and the mixture was stirred keeping the temperature below −30° C. for 30 minutes. The reaction mixture was diluted with ether and washed with 0.5 M HCl. The aqueous was extracted with ether and then the combined organic layers were sequentially washed with 0.1 M Na$_2$S$_2$O$_3$ (2x), water, and brine, then dried over MgSO$_4$. The crude product was purified via SiO$_2$ flash chromatography (dry loaded, eluted with DCM/ethyl acetate (100:1) to (50:1) to (10:1)) to give products 3 and 4 as slightly yellow solids (3: 4.29 g, 19% yield; 4: 9.28 g, 30% yield). For compound 3: $^1$H-NMR (400 MHz, chloroform-d) δ 7.49 (s, 1H), 7.05 (d, J=7.6 Hz, 1H), 6.91 (d, J=8.0 Hz, 1H), 5.62 (brd s, 1H), 4.56 (brd s, 1H), 3.31 (brd q, J=5.6 Hz, 2H), 2.69 (brd t, J=6.8 Hz, 2H), 1.44 (s, 9H); $^{13}$C-NMR (100 MHz, chloroform-d) δ 155.9, 153.6, 138.3, 133.0, 130.0, 115.0, 85.5, 79.4, 41.8, 34.8, 28.4; HRMS (EI+) for $C_{13}H_{18}INO_3$ calcd. 363.0331 found 363.0336. For compound 4: $^1$H-NMR (400 MHz, chloroform-d) δ 7.51 (s, 2H), 5.74 (s, 1H), 4.58 (brd s, 1H), 3.30 (app q, J=6.2 Hz, 2H), 2.67 (t, J=6.4 Hz, 2H), 1.40 (s, 9 H); $^{13}$C-NMR (100 MHz, chloroform-d) δ155.8, 152.2, 139.4, 135.1, 82.3, 79.5, 41.6, 34.2, 28.4; HRMS (EI+) for $C_{13}H_{17}I_2NO_3$ [M-$C_4H_9$+H] calcd. 432.8672 found 432.8663.

Example 3

Preparation of 1-bromo-4-(triisopropyl)silyloxy-benzene (6)

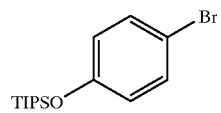

6

To a stirred solution of p-bromophenol (5) (4.0 g, 23.1 mmol) in DCM (40 ml) was added triisopropylsilyl chloride (5 ml, 23.4 mmol). The reaction mixture was cooled to 0° C. and imidazole (3.94 g, 57.9 mmol) was added and the mixture was stirred at 0° C. for 30 minutes then allowed to warm to ambient temperature over 12 hours. The reaction mixture was diluted with ether and sequentially washed with 0.5 M HCl (2×), sat. aq. NaHCO$_3$, water and brine then dried over MgSO$_4$. The crude product was purified by bulb to bulb distillation (boiling point: 149–150° C. at 2.0 mmHg) to give 6 as a clear oil (6.23 g, 82% yield): $^1$H-NMR (400 MHz, chloroform-d) δ7.30 (d, J=8.8 Hz, 2H), 6.75 (d, J=8.8 Hz, 2H), 1.24 (septet, J=7.2 Hz, 3H), 1.09 (d, J=7.2 Hz, 18H); $^{13}$C-NMR (100 MHz, chloroform-d) δ155.2, 132.2, 121.7, 113.2, 17.8, 12.6; FTIR (thin film) 2945, 2892, 2867, 1586, 1487, 1274, 909, 883, 828, 732 cm$^{-1}$; HRMS (EI+) for $C_{15}H_{25}BrOSi$ calcd. 328.0858 found 328.0844.

Example 4

Preparation of 4-(triisopropyl)silyloxyphenyl boronic acid (7)

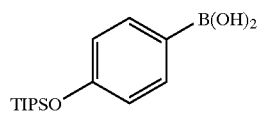

7

To a stirring solution of 4-(triisopropyl)silyloxy-1-bromobenzene (6) (540 mg, 1.64 mmol) in THF (15 ml) at −78° C. was added n-butyl lithium (0.9 ml, 2.18 M in hexanes, 1.96 mmol) dropwise. The reaction mixture was stirred for 30 minutes then triisopropyl borate (0.5 ml, 2.17 mmol) was added in one portion. The reaction was stirred at −78° C. for 1 hour, allowed to warm to ambient temperature over 4 hours, quenched with 3 N HCl (5 ml) and stirred for 30 minutes at 0° C. The aqueous layer was extracted with ethyl acetate (3×) and the combined organic layers were dried over MgSO$_4$. Purification by flash SiO$_2$ chromatography (loaded with DCM, eluted with hexanes/ethyl acetate (10:1) to (3:1) to (1:1)) gave 7 as a white solid (328 mg, 68% yield): $^1$H-NMR (400 MHz, chloroform-d) δ 8.10 (d, J=8.4 Hz, 2H), 6.98 (d, J=8.4 Hz, 2H), 1.30 (septet, J=7.6 Hz, 3H), 1.13 (d, J=7.6 Hz, 18H); $^{13}$C-NMR (100 MHz, chloroform-d) δ 160.1, 137.4, 119.6, 17.9, 12.7.

Method A: General Procedure for Copper Mediated Coupling

The boronic acid (11.3 mmol) and the phenol (5.52 mmol) were dissolved in DCM (60 ml) at ambient temperature in a flask flushed with dry air. A large excess of 4 Å powdered molecular sieves were added and the mixture was allowed to stir for 10 minutes with a drying tube attached. Copper(II) acetate (5.60 mmol), triethylamine (27.3 mmol), and pyridine (27.2 mmol) were added in succession and the reaction was stirred at ambient temperature overnight. The reaction mixture was diluted with ether and filtered through celite and the filtrate was sequentially washed with 0.5 M HCl (1×), water (1×), and brine (1×) then dried over MgSO$_4$. The crude product was purified via flash SiO$_2$ chromatography as described below.

Example 5

Preparation of N-t-Boc-4'-triisopropylsilyloxy-thyronamine (8)

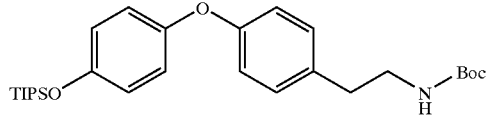

8

Refer to Method A for the general procedure. The crude product was purified via flash SiO$_2$ chromatography (loaded with DCM, eluted with hexanes/ethyl acetate (10:1) to (5:1)) to give 8 as a slightly yellow oil (122 mg, 40% yield): $^1$H-NMR (400 MHz, chloroform-d) δ 7.10 (d, J=8.0 Hz, 2H), 6.90–6.83 (m, 6H), 4.59 (brd s, 1H), 3.35 (brd q, J=6.0 Hz, 2H), 2.74 (brd t, J=7.0 Hz, 2H), 1.43 (s, 9H), 1.27 (septet, J=7.6 Hz, 3H), 1.10 (d, J=7.2 Hz, 18H); HRMS (EI+) for $C_{28}H_{43}NO_4Si$ calcd. 485.2961 found 485.2958.

Example 6

Preparation of N-t-Boc-4'-triisopopylsilyloxy-3-iodothyronamine (9)

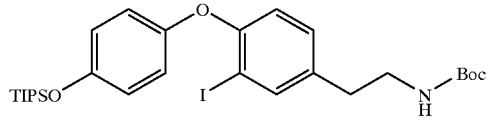

9

Refer to Method A for the general procedure. The crude product was purified via flash SiO$_2$ chromatography (dry loaded, eluted with hexanes/ethyl acetate (10:1)) to give 9 as a slightly yellow oil (923 mg, 36% yield). $^1$H-NMR (400 MHz, chlorofom-d) δ7.65 (d, J=1.6 Hz, 1H), 7.05 (app d, J=8.0 Hz, 1H), 6.86 (s, 4H), 6.68 (d, J=8.8 Hz, 1H), 4.57 (brd s, 1H), 3.33 (brd q, J=6.5 Hz, 2H), 2.72 (t, J=6.8 Hz, 2H), 1.44 (s, 9H), 1.25 (septet, J=7.2 Hz, 3H), 1.10 (d, J=7.2 Hz, 18H); $^{13}$C-NMR (100 MHz, chlorofom-d) δ156.1, 155.7, 152.3, 150.1, 139.7, 135.3, 129.8, 120.7, 120.1, 117.5, 87.6, 79.2, 41.6, 34.8, 28.3, 17.8, 12.5; FTIR (thin film) 3360, 2944, 2867, 1704, 1502, 1479, 1366, 1232, 1194, 1171, 910, 883, 734 cm$^{-1}$; HRMS (EI+) for $C_{28}H_{421}NO_4Si$ calcd. 611.1928 found 611.1917.

Example 7

Preparation of N-t-Boc-4'-triisopropylsilyloxy-3,5-diiodothyronamine (10)

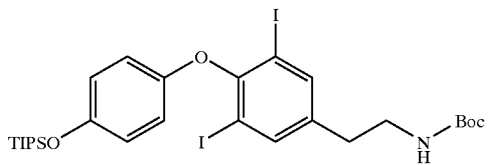

10

Refer to method A for the general procedure. The crude product was purified by flash SiO$_2$ chromatography (dry loaded, eluted with hexanes/ethyl acetate (10:1) to (8:1)) to give 10 as a slightly yellow oil (1.28 g, 51% yield (based on recovered starting material)): $^1$H-NMR (400 MHz, chloroform-d) δ 7.67 (s, 2H), 6.79 (d, J=9.2 Hz, 2H), 6.63 (d, J=9.2 Hz, 2H), 4.79 (brd s, 1H), 3.33 (brd q, J=6.7 Hz, 2H), 2.72 (brd t, J=6.8 Hz, 2H), 1.45 (s, 9H), 1.23 (septet, J=7.6 Hz, 3H), 1.08 (d, J=7.2 Hz, 18H); $^{13}$C-NMR (100 MHz, chloroform-d) δ 155.6, 152.7, 150.8, 150.4, 140.3, 139.6, 120.4, 116.1, 91.1, 79.2, 41.4, 34.5, 28.3, 17.8, 12.4; FTIR (thin film) 3446, 2944, 2867, 1705, 1500, 1438, 1241, 1187, 908, 734 cm$^{-1}$; HRMS (EI+) for $C_{28}H_{41}I_2NO_4Si$ calcd. 737.0894 found 737.0888.

Method B: General Procedure for Silyl Deprotection

To a stirred solution of protected phenol (1.0 mmol) in THF (10 ml) was added TBAF (1.5 ml, 1.5 mmol, 1 M solution in THF) dropwise. The reaction mixture was stirred for 10–30 minutes until complete by TLC analysis, then diluted with ethyl acetate. The reaction mixture was washed with 0.5 M HCl and the aqueous was extracted with ethyl acetate. The combined organic layers were sequentially washed with water and brine then dried over MgSO$_4$. The crude product was purified by flash SiO$_2$ chromatography as described below.

Example 8

Preparation of N-t-Boc-thyronamine (11)

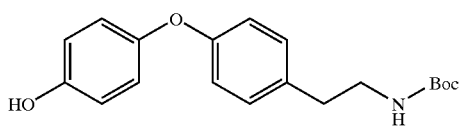

11

Refer to Method B for the general procedure. The crude product was purified via flash SiO$_2$ chromatography (loaded with DCM, eluted with hexanes/ethyl acetate (10:1) to (3:1)) to give 11 as a clear oil (42.4 mg, 86% yield): $^1$H-NMR (400 MHz, methanol-d$_4$) δ 7.11 (d, J=8.0 Hz, 2H), 6.83–6.73 (m, 6H), 4.85 (s, 1H), 3.21 (brd t, J=7.4 Hz, 2H), 2.69 (t, J=7.0 Hz, 2H), 1.40 (s, 9H); HRMS (EI+) for $C_{19}H_{23}NO_4$ calcd. 329.1627 found 329.1615.

Example 9

Preparation of N-t-Boc-3-iodothyronamine (12)

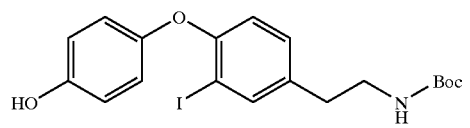

12

Refer to Method B for the general procedure. The crude was purified via flash SiO$_2$ chromatography (loaded with DCM, eluted with hexanes/ethyl acetate (5:1) to (3:1)) to give 12 as a clear oil (54.3 mg, 85% yield): $^1$H-NMR (400 MHz, chloroform-d) δ 7.64 (d, J=2.0 Hz, 1H), 7.01 (app dd, J=8.4, 2.0 Hz, 1H), 6.87 (app dt, J=9.2, 2.8 Hz, 2H), 6.82 (app dt, J=9.2, 2.8 Hz, 2H), 6.67 (d, J=8.4 Hz, 1H), 6.20 (brd s, 1H), 4.65 (brd s, 1H), 3.33 (brd q, J=6.5 Hz, 2H), 2.71 (brd t, J=7.0 Hz, 2H), 1.45 (s, 9H); $^{13}$C-NMR (100 MHz, chloroform-d) δ 156.2, 156.1, 152.5, 149.8, 139.7, 135.2, 129.8, 120.4, 117.6, 116.3,87.8,79.7,41.8, 34.9,28.4; HRMS (EI+) for $C_{19}H_{221}NO_4$ [M+H-$C_4H_9$] calcd. 398.9968 found 398.9950.

Example 10

Preparation of N-t-Boc-3,5-diiodothyronamine (13)

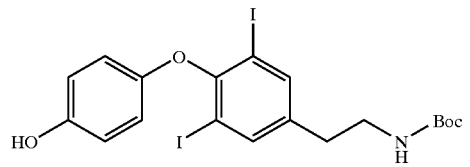

13

Refer to Method B for the general procedure. The crude product was purified by flash SiO$_2$ chromatography (dry loaded, eluted with hexanes/ethyl acetate (10:1) to (5:1)) to give 13 as a yellow oil (221 mg, 72% yield): $^1$H-NMR (400 MHz, methanol-d$_4$) δ 7.74 (s, 2H), 6.67 (d, J=9.2 Hz, 2H), 6.54 (d, J=9.2 Hz, 2H), 4.84 (brd s, 1H), 3.25 (t, J=6.8 Hz, 2H), 2.69 (t, J=6.8 Hz, 2H), 1.41 (s, 9H); $^{13}$C-NMR (100 MHz, methanol-d$_4$) δ 158.4, 154.2, 153.3, 151.1, 141.9, 141.7, 117.3, 116.8, 91.9, 80.0, 42.4, 35.4, 28.8; HRMS (EI+) for $C_{19}H_{21}I_2NO_4$ [M+H]+calcd. 581.9638 found 581.9626.

Example 11

Preparation of N-t-Boc-3'-iodothyronamine (14) and N-t-Boc-3',5'-diiodothyronamine (15)

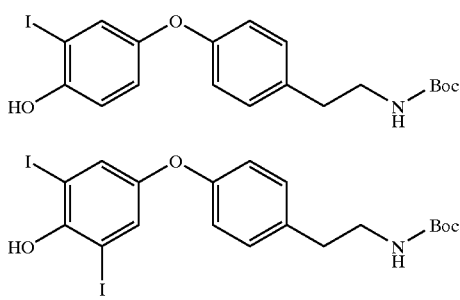

Iodine monochloride (0.24 ml, 0.24 mmol, 1 M solution in DCM) was added dropwise to a stirred solution of N-t-Boc-O-(4-hydroxy)phenyl tyramine 11 (52.1 mg, 0.16 mmol) and butyl amine (0.08 ml, 0.81 mmol) in DCM (1.0 ml) and DMF (0.25 ml) at −40° C. The reaction was kept below −35° C. for one hour, then allowed to warm to ambient temperature overnight. The crude reaction mixture was diluted with ethyl acetate and sequentially washed with 0.1 M $Na_2S_2O_3$ (1×), 0.5 M HCl (1×), water, and brine then dried over $MgSO_4$. The crude products were separated via flash $SiO_2$ chromatography (loaded with DCM, eluted with DCM/ethyl acetate (100:1) to (50:1)) to give 14 and 15 as slighty yellow oils (14: 17.3 mg, 24% yield; 15: 39.1 mg, 43% yield). For compound 14: $^1$H-NMR (400 MHz, chloroform-d) δ 7.33 (d, J=1.6 Hz, 1H), 7.12 (d, J=8.0 Hz, 2H), 6.96–6.94(m, 2H), 6.87 (d, J=8.4 Hz, 2H), 5.47 (s, 1H), 4.57 (brd s, 1H), 3.36 (app brd q, J=6.0 Hz, 2H), 2.76 (t, J=6.8 Hz, 2H), 1.44 (s, 9H); HRMS (EI+) for $C_{19}H_{22}INO_4$ calcd. 455.0594 found 455.0610. For compound 15: $^1$H-NMR 400 MHz, chloroform-d) δ 7.37 (s, 2H), 7.15 (d, J=8.4 Hz, 2H), 6.88 (d, J=8.4 Hz, 2H), 5.63 (brd s, 1H), 4.57 (brd s, 1H), 3.37 (brd q, J=6.4 Hz, 2H), 2.77 (t, J=6.8 Hz, 2H), 1.44 (s, 9H); $^{13}$C-NMR (100 MHz, chloroform-d) δ 155.8, 155.7, 151.1, 150.1, 134.2, 130.2, 129.7, 118.3, 81.3, 41.8, 35.4, 28.4; HRMS (EI+) for $C_{19}H_{21}I_2NO_4$ [M-$C_4H_9$+H] calcd. 524.8934 found 524.8940.

Example 12

Preparation of N-t-Boc-3,3'-diiodothyronamine (16)

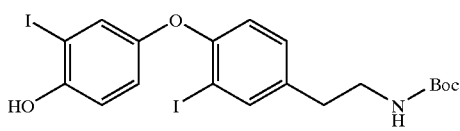

Iodine (41.8 mg, 0.16 mmol) was added to a saturated potassium iodide solution (0.1 ml) and the resulting solution was added dropwise to a stirred solution of phenol 12 (41.9 mg, 0.092 mmol) in an ethyl amine solution (1 ml, 1 M in THF) at −40° C. After 30 minutes the reaction mixture was warmed to 0° C. and stirred for an additional hour. The reaction mixture was diluted with ethyl acetate and sequentially washed with 3 M HCl, 0.1 M $Na_2S_2O_3$, and brine then dried over $MgSO_4$. The crude product was purified by flash $SiO_2$ chromatography (loaded with DCM, eluted with DCM/ethyl acetate (100:1)) to give 16 as a slightly yellow oil (18.2 mg, 34% yield): $^1$H-NMR (400 MHz, chloroform-d) δ 7.67 (d, J=2.0 Hz, 1H), 7.29 (d, J=2.8, 1H), 7.09 (d, J=8.4 Hz, 1H), 6.96 (d, J=8.8 Hz, 1H), 6.91 (dd, J=8.8, 2.8 Hz, 1H), 6.73 (d, J= 8.4 Hz, 1H), 5.37 (s, 1H), 4.57 (brd s, 1H), 3.34 (brd q, J=6.4 Hz, 2H), 2.74 (t, J=7.0 Hz, 2H), 1.45 (s, 9H); $^{13}$C-NMR (100 MHz, chloroform-d) δ 155.8, 155.5, 151.5, 150.4, 139.9, 136.2, 130.1, 128.2, 120.8, 118.2, 115.3, 88.1, 85.1, 79.5, 41.7, 35.0, 28.4; HRMS (EI+) for $C_{19}H_{21}I_2NO_4$ [M-$C_4H_9$+H] calcd. 524.8934 found 524.9560.

Example 13

Preparation of N-t-Boc-3,3',5'-triiodothyronamine (17)

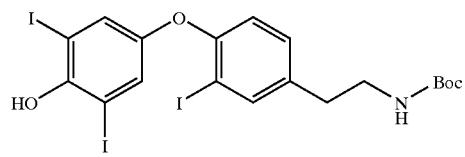

Iodine monochloride (0.16 ml, 0.16 mmol, 1 M solution in DCM) was added dropwise to a stirred solution of phenol 12 (34.1 mg, 0.075 mmol) and butyl amine (0.04 ml, 0.40 mmol) in DMF (0.5 ml) and DCM (2 ml) at 0° C. The reaction stirred at 0° C. until complete by TLC analysis (20 min), then diluted with ethyl acetate and sequentially washed with 0.5 M HCl, 0.1 M $Na_2S_2O_3$, water, and brine then dried over $MgSO_4$. The crude product was purified via flash $SiO_2$ (loaded with DCM, eluted with hexanes/ethyl acetate (5:1) to (2:1)) to give 17 as a slightly yellow oil (41.4 mg, 78% yield): $^1$H-NMR (400 MHz, chloroform-d) δ 7.68 (d, J=1.6 Hz, 1H), 7.33 (s, 2H), 7.12 (dd, J=8.4, 1.6 Hz, 1H), 6.76 (d, J=8.4 Hz, 1H), 5.61 (brd s, 1H), 4.58 (brd s, 1H), 3.35 (q, J=6.4 Hz, 2H), 2.75 (t, J=7.0 Hz, 2H), 1.45 (s, 9H); HRMS (EI+) for $C_{19}H_{20}I_3NO_4$ calcd. 706.8527 found 706.8529.

Example 14

Preparation of N-t-Boc-3,3',5-triiodothyronamine (18)

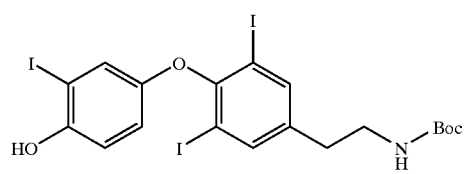

Iodine (17.0 mg, 0.067 mmol) was added to a saturated potassium iodide solution (0.07 ml) and the resulting solution was added dropwise to a stirred solution of phenol 13 (32.1 mg, 0.055 mmol) in THF (1 ml) and butyl amine (0.5 ml) at −40° C. After 30 minutes the reaction mixture was warmed to 0° C. and stirred for an additional hour. The reaction mixture was diluted with ethyl acetate and sequentially washed with 3 M HCl, 0.1 M Na$_2$S$_2$O$_3$, and brine then dried over MgSO$_4$. The crude product was purified by flash SiO$_2$ chromatography (loaded with DCM, eluted with DCM/ethyl acetate (100:1)) to give 18 as a slightly yellow oil (10.3 mg, 26% yield): $^1$H-NMR (400 MHz, chloroform-d) δ 7.76 (s, 2H), 7.01 (d, J=2.8 Hz, 1H), 6.72 (d, J=9.2 Hz, 1H), 6.57 (dd, J=8.8, 2.8 Hz, 1H), 4.86 (s, 1H), 3.27 (obsc brd t, J=6.0 Hz, 2H), 2.71 (t, J=6.8 Hz, 2H), 1.41 (s, 9H).

Example 15

Preparation of N-t-Boc-3,3',5,5'-tetraioodothyronamine (19)

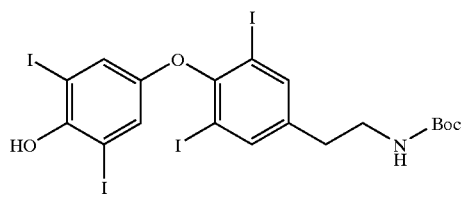

Iodine monochloride (0.11 ml, 0.11 mmol, 1 M solution in DCM) was added dropwise to a stirred solution of phenol 13 (27.7 mg, 0.048 mmol) and butyl amine (0.5 ml, 2.53 mmol) in THF (1 ml) at −45° C. After 30 minutes the reaction was partitioned between 0.5 M HCl and ethyl acetate. The organic phase was sequentially washed with 0.1 M Na$_2$S$_2$O$_3$ and brine then dried over MgSO$_4$. The crude product was purified by flash SiO$_2$ chromatography (dry loaded, eluted with hexanes/ethyl acetate (5:1)) to give 19 as a slightly yellow oil (18.4 mg, 46% yield). $^1$H-NMR (400 MHz, methanol-d$_4$) δ 7.78 (s, 2H), 7.08 (s, 2H), 3.30 (brd s, 2H), 2.73 (t, J=7.0 Hz, 2H), 1.42 (s, 9H).

Method C: General Procedure for t-Boc Deprotection

The protected amine (31.2 mg, 0.054 mmol) was dissolved in a 1 N HCl or 3 N HCl solution in ethyl acetate (2 ml, anhydrous) and the reaction mixture was stirred at ambient temperature for 5–15 hours. A white precipitate was noted after 1.5 hours. Additional HCl was added as needed (2 ml) and the reaction mixture was stirred over night. The reaction was completed as described below.

Example 16

Preparation of thyronamine hydrochloride (22)

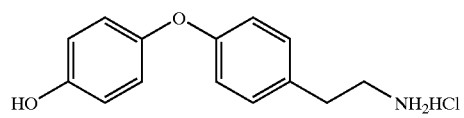

Refer to Method C for the general procedure. The crude reaction mixture was concentrated in vacuo and dried under high vacuum pressure to give 22 as a slightly tan solid (32.9 mg, 100% yield): $^1$H-NMR (400 MHz, dimethylsulfoxide-d$_6$) δ 9.37 (s, 1H), 7.90 (brd s, 3H), 7.20 (d, J=8.4 Hz, 1H), 6.86 (ovrlp d, J=8.8 Hz, 1H), 6.85 (ovrlp d, J=8.4 Hz, 1H), 6.78 (d, J=8.8 Hz, 1H), 2.99 (app brd q, J=8.0 Hz, 2H), 2.81 (t, J=8.2 Hz, 2H); HRMS (EI+) for C$_{14}$H$_{15}$NO$_2$ calcd. 229.1103 found 229.1107.

Example 17

Preparation of 3-iodothyronamine hydrochloride (23)

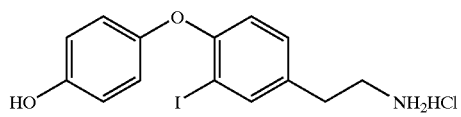

Refer to Method C for the general procedure. The crude precipitate was filtered to give 23 as a white solid (816 mg, 93% yield): $^1$H-NMR (400 MHz, DMSO-d$_6$) δ 9.44 (s, 1H), 8.12 (brd s, 3H), 7.76 (s, 1H), 7.20 (d, J=8.0 Hz, 1H), 6.79 (s, 4H), 6.68 (d, J=8.4 Hz, 1H), 2.98 (app brd q, J=7.2 Hz, 2H), 2.84 (t, J=7.4 Hz, 2H); HRMS (EI+) for C$_{14}$H$_{14}$INO$_2$ [M-NH$_3$] calcd. 337.9804 found 337.9812.

Example 18

Preparation of 3,5-diiodothyronamine hydrochloride (24)

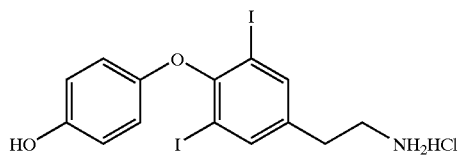

Refer to Method C for the general procedure. The crude reaction mixture was concentrated in vacuo and dried under high vacuum pressure to give 24 as a white solid (26.7 mg, 96% yield): $^1$H-NMR (400 MHz, D$_2$O) δ 7.97 (s, 2H), 6.89 (d, J=6.8 Hz, 2H), 6.79 (d, J= 7.2 Hz, 2H), 3.29 (app t, J=6.4 Hz, 2H), 3.01 (app t, J=6.4 Hz, 2H); HRMS (EI+) for C$_{14}$H$_{13}$I$_2$NO$_2$ calcd. 480.9036 found 480.9050.

Example 19

Preparation of 3'-iodothyronamine hydrochloride (25)

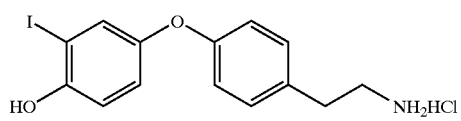

Refer to Method C for the general procedure. The crude reaction mixture was concentrated in vacuo and dried under high vacuum pressure to give 25 as a white solid (12.7 mg, 98% yield): $^1$H-NMR (400 MHz, DMSO-d$_6$) δ 10.24 (s, 1H), 7.86 (s, 3H), 7.30 (d, J=2.4 Hz, 1H), 7.23 (d, J=8.4 Hz, 2H), 6.96–6.86 (m, 4H), 3.01 (brd s, 2H), 2.83 (app t, J=7.6 Hz, 2H); HRMS (EI+) for $C_{14}H_{14}INO_2$ [M–NH$_3$] calcd. 337.9804 found 337.9809.

Example 20

Preparation of 3',5'-diiodothyronamine hydrochloride (26)

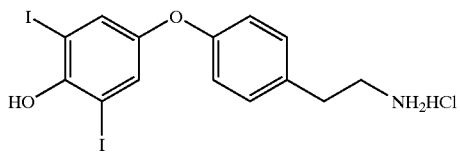

26

Refer to Method for the general procedure. The crude reaction mixture was diluted with ether and the precipitated product was collected via vacuum filtration to give 26 as a white solid (32.3 mg, 88% yield): $^1$H-NMR (400 MHz, DMSO-d$_6$) δ 9.41 (s, 1H), 7.95 (s, 3H), 7.39 (s, 2H), 7.27 (d, J=8.4 Hz, 2H), 6.96 (d, J=8.4 Hz, 2H), 3.02 (brd s, 2H), 2.86 (app brd t, J=8.0 Hz, 2H); HRMS (EI+) for $C_{14}H_{13}I_2NO_2$ [M-NH$_3$] calcd. 463.8770 found 463.8748.

Example 21

Preparation of 3,3'-diiodothyronamine hydrochloride (27)

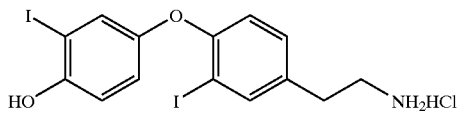

27

Refer to Method C for the general procedure. The crude reaction mixture was concentrated in vacuo and dried under high vacuum pressure to give 27 as a white solid (14.6 mg, 100% yield): $^1$H-NMR (400 MHz, DMSO-d$_6$) δ 10.27 (s, 1H), 7.96 (brd s, 3H), 7.79 (d, J= 1.6 Hz, 1H), 7.25 (ovrlp dd, J=8.4, 2.0 Hz, 1H), 7.23 (ovrlp d, J=2.8 Hz, 1H), 6.92 (ovrlp d, J=8.8 Hz, 1H), 6.87 (ovrlp dd, J=8.8, 2.8 Hz, 1H), 6.81 (d, J=8.0 Hz, 1H), 3.03 (app brd s, 2H), 2.84 (brd t, J=7.6 Hz, 2H).

Example 22

Preparation of 3,3',5'-triiodothyronamine hydrochloride (28)

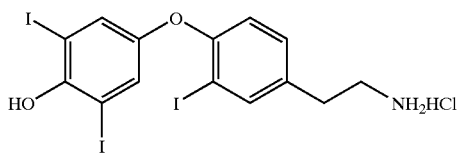

28

Refer to Method C for the general procedure. The crude reaction mixture was diluted with ether and the white precipitate was collected by vacuum filtration to give 28 as a white solid (27.1 mg, 85% yield). $^1$H-NMR (400 MHz, DMSO-d$_6$) δ 9.39 (s, 1H), 7.92 (brd s, 3H), 7.81 (d, J=2.0 Hz, 1H), 7.29 (ovrlp dd, J=8.0, 2.0 Hz, 1H), 7.29 (ovrlp s, 2H), 6.95 (d, J= 8.4 Hz, 1H), 3.05 (brd s, 2H), 2.85 (t, J=7.6 Hz, 2H).

Example 23

Preparation of 3,3',5-triiodothyronamine hydrochloride (29)

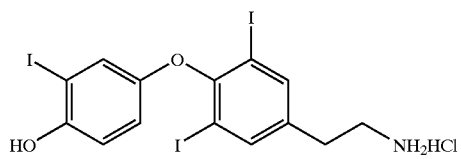

29

Refer to Method C for the general procedure. The crude reaction was concentrated in vacuo and dried under high vacuum pressure to give 29 as a tan solid (9.6 mg, 100% yield): $^1$H-NMR (400 MHz, DMSO-d$_6$) δ 10.00 (s, 1H), 7.86 (ovrlp s, 2H), 7.80 (ovrlp brd s, 3H), 6.98 (d, J=2.8 Hz, 1H), 6.83 (d, J=9.2 Hz, 1H), 6.65 (dd, J=8.8, 3.2 Hz, 1H), 3.11 (t, J=7.2 Hz, 2H), 2.84(t, J=7.2 Hz, 2H).

Example 24

Preparation of 3,3',5,5'-tetraiodothyronamine hydrochloride (30)

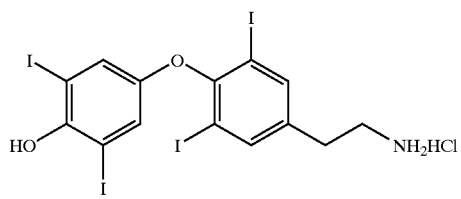

30

Refer to Method C for the general procedure. The crude reaction was concentrated in vacuo and dried under high vacuum pressure to give 30 as a tan solid (13.8 mg, 100% yield): $^1$H-NMR (400 MHz, DMSO-d$_6$) δ 9.25 (s, 1H), 7.87 (s, 2H), 7.11 (s, 2H), 3.12 (app brd s, 2H), 2.85 (t, J=7.2 Hz, 2H).

Example 25

Preparation of N-t-Boc-O-phenyl tyramine (20)

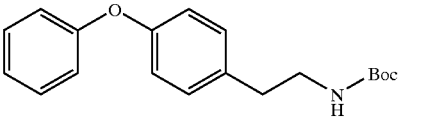

20

Refer to Method A for the general procedure. The crude product was purified via flash SiO$_2$ chromatography (dry loaded, eluted with hexanes/ethyl acetate (10:1) to (5:1)) to give 20 as a white crystalline solid (50.5 mg, 73% yield): $^1$H-NMR (400 MHz, chlorofom-d) δ 7.32 (app t, J=7.6 Hz, 2H), 7.14 (d, J=8.4 Hz, 2H), 7.08 (t, J=7.6 Hz, 1H), 6.99 (d, J=7.6 Hz, 2H), 6.94 (app d, J=8.4 Hz, 2H), 4.57 (brd s, 1H), 3.36 (brd q, J=6.0 Hz, 2H), 2.77 (t, J= 7.0 Hz, 2H), 1.44 (s, 9H); $^{13}$C-NMR (100 MHz, chlorofom-d) δ 157.4, 155.8, 133.8, 130.0, 129.7, 123.1, 119.0, 118.7, 79.2, 41.8, 35.5, 28.4; HRMS (EI+) for $C_{19}H_{23}NO_3$ 313.1678 found 313.1686.

Example 26

Preparation of O-phenyl-tyramine hydrochloride (31)

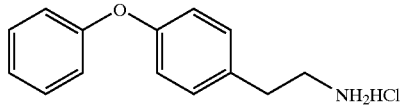

Refer to Method C for the general procedure. The crude reaction was concentrated in vacuo and dried under high vacuum pressure to give 31 as a tan solid (18.3 mg, 100% yield): $^1$H-NMR (400 MHz, DMSO-d$_6$) δ 8.17 (brd s, 3H), 7.38 (app t, J=7.6 Hz, 2H), 7.28 (d, J=8.4 Hz, 2H), 7.13 (t, J=7.4 Hz, 1H), 7.02–6.94 (m, 4H), 3.02 (app brd t, J=8.0 Hz, 2H), 2.90 (app t, J=8.4 Hz, 2H); HRMS (EI+) for $C_{14}H_{15}NO$ calcd. 213.1154 found 213.1158.

Method D: General Procedure for O-alkylation of N-t-Boc Tyramine

The requisite alkyl halide (20.2 mmol) and potassium carbonate (3.50 g, 25.3 mmol) were added to a stirred solution of N-t-Boc tyramine (4.02 g, 17.0 mmol) in DMF (25 ml) at ambient temperature. The reaction mixture was vigorously stirred at ambient temperature for 4 to 48 hours, then diluted with ether and washed with 0.5 M HCl. The aqueous was extracted with ether and the combined organic layers were sequentially washed with water (2×) and brine then dried over MgSO$_4$. Concentration gave the crude O-alkylated product which was purified as described below.

Example 27

Preparation of N-t-Boc-O-benzyl-tyramine (21)

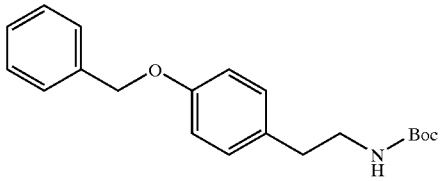

Refer to Method D for the general procedure. The crude product was purified via flash SiO$_2$ (loaded with DCM, eluted with hexanes/ethyl acetate (10:1) to (5:1)) to give 21 as a flaky white solid (3.24 g, 58% yield): $^1$H-NMR (400 MHz, chloroform-d) δ 7.42-7.27 (m, 5H), 7.08 (d, J=8.4 Hz, 2H), 6.90 (d, J=8.4 Hz, 2H), 5.02 (s, 2H), 4.60 (brd s, 1H), 3.32 (app brd q, J=6.0 Hz, 2H), 2.71 (app brd t, J=6.6 Hz, 2H), 1.43 (s, 9H); $^{13}$C-NMR (100 MHz, chloroform-d) δ 157.3, 155.8, 137.0, 131.2, 129.6, 128.5, 127.8, 127.3, 114.8, 79.0, 69.9, 41.8, 35.2, 28.3; HRMS (EI+) for $C_{20}H_{25}NO_3$ calcd. 327.1834 found 327.1819.

Example 28

Preparation of N-t-Boc-O-benzyl-3-iodotyramine (33)

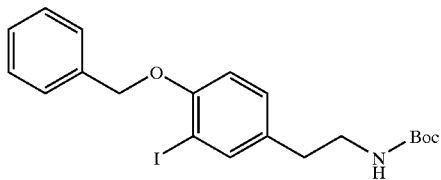

Benzyl bromide (0.07 ml, 0.59 mmol) and K$_2$CO$_3$ (89 mg, 0.64 mmol) were added to a stirred solution of phenol 2 (104 mg, 0.28 mmol) in DMF (2 ml). The mixture was vigorously stirred for 3 hours until the reaction was complete by TLC analysis. The reaction mixture was partitioned between ether and 0.5 M HCl. The organic layer was sequentially washed with water (2×) and brine then dried over MgSO$_4$. Concentration resulted in a yellow oil which was purified via flash SiO$_2$ chromatography (dry loaded, eluted with hexanes/ethyl acetate (10:1) to (5:1)) to give 33 as a clear oil (98.8 mg, 78% yield). $^1$H-NMR (400 MHz, DMSO-d$_6$) δ 7.63 (d, J=2.0 Hz, 1H), 7.49 (d, J=7.6 Hz, 2H), 7.39 (t, J=7.6 Hz, 2H), 7.32 (app t, J=7.4 Hz, 1H), 7.08 (app dd, J=7.2, 2.0 Hz, 1H), 6.78 (d, J=8.4 Hz, 1H), 5.13 (s, 2H), 4.52 (brd s, 1H), 3.31 (app q, J=6.8 Hz, 2H), 2.69 (app t, J=7.0 Hz, 2H), 1.44 (s, 9H); HRMS (EI+) for $C_{20}H_{24}INO_3$ calcd. 453.0801 found 453.0806.

Example 29

Preparation of N-t-Boc-O-(2-phenyl)ethyl tyramine (34)

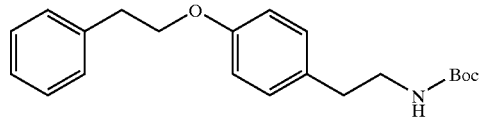

Refer to Method D for the general procedure. The crude product was purified via flash SiO$_2$ chromatography (dry loaded, eluted with hexanes/ethyl acetate (5:1)) to give 34 as a clear oil (38.6 mg, 49% yield based on recovered starting material): $^1$H-NMR (400 MHz, chloroform-d) δ 7.38–7.22 (m, 5H), 7.08 (d, J=8.0 Hz, 2H), 6.83 (d, J=8.4 Hz, 2H), 4.52 (brd s, 1H), 4.15 (t, J=7.2 Hz, 2H), 3.33 (app brd q, J=6.0 Hz, 2H), 3.09 (t, J=7.0 Hz, 2H), 2.72 (t, J=6.8 Hz, 2H), 1.43 (s, 9H); $^{13}$C-NMR (100 MHz, chloroform-d) δ 157.4, 155.8, 138.2, 131.0, 129.7, 129.0, 128.4, 126.4, 114.6,79.1, 68.7, 41.9,35.8,35.2, 28.4; HRMS (EI+) for $C_{21}H_{27}NO_3$ calcd. 341.1991 found 341.1990.

Example 30

Preparation of N-t-Boc-O-(p-fluoro)benzyl tyramine (35)

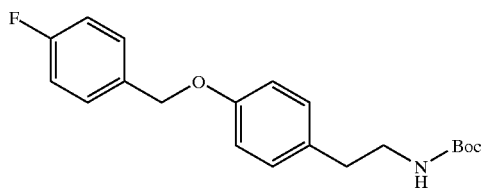

Refer to Method D for the general procedure. The crude product was purified via flash SiO$_2$ chromatography (loaded with DCM, eluted with hexanes/ethyl acetate (10:1) to (5:1)) to give 35 as a white solid (653 mg, 86% yield): $^1$H-NMR (400 MHz, chloroform-d) δ 7.40 (app dd, J=8.4, 5.2 Hz, 2H), 7.10 (ovrlp d, J=8.4 Hz, 2H), 7.06 (ovrlp app t, J=8.8 Hz, 2H), 6.90 (app d, J=8.8 Hz, 2H), 5.00 (s, 2H), 4.52 (brd s, 1H), 3.34 (app brd q, J=6.4 Hz, 2H), 2.73 (t, J=7.0 Hz, 2H), 1.43 (s, 9H); $^{13}$C-NMR (100 MHz, chloroform-d) δ 162.7 ($J_{CF}$=245 Hz), 157.5, 156.1, 133.0, 131.7, 130.0, 129.5 ($J_{CF}$=8.2 Hz), 115.7 ($J_{CF}$=21.4 Hz), 115.1, 79.4, 69.6, 42.1, 35.5, 28.6.

Example 31

Preparation of N-t-Boc-O-(m-methoxy)benzyl tyramine (36)

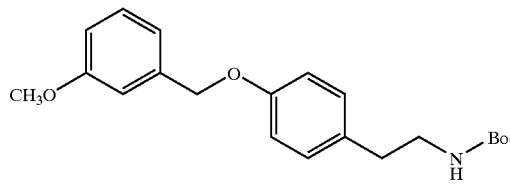

Refer to Method D for the general procedure. The crude product was purified via flash SiO$_2$ chromatography (loaded with DCM, eluted with hexanes/ethyl acetate (10:1) to (5:1)) to give 36 as a white solid (577 mg, 74% yield): $^1$H-NMR (400 MHz, chloroform-nd) δ 7.29 (t, J=8.0 Hz, 1H), 7.09 (d, J=8.4 Hz, 2H), 6.99 (app d, J=8.4 Hz, 2H), 6.91 (d, J=8.4 Hz, 2H), 6.85 (app dd, J=8.4, 2.4 Hz, 1H), 5.02 (s, 2H), 4.54 (brd s, 1H), 3.81 (s, 3H), 3.33 (brd q, J=6.0 Hz, 2H), 2.73 (t, J=6.8 Hz, 2H), 1.43 (s, 9H).

Example 32

Preparation of N-t-Boc-O-(p-trifluoromethyl)benzyl tyramine (37)

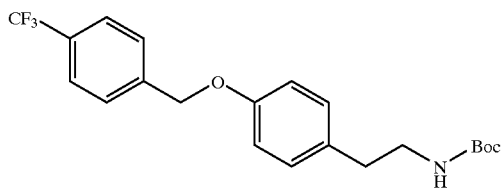

Refer to Method D for the general procedure. The crude product was purified via flash SiO$_2$ chromatography (loaded with DCM, eluted with hexanes/ethyl acetate (10:1) to (5:1)) to give 37 as a white solid (740 mg, 87% yield): $^1$H-NMR (400 MHz, chloroform-d) δ 7.63 (d, J=8.4 Hz, 2H), 7.54 (d, J=8.0 Hz, 2H), 7.11 (d, J=8.0 Hz, 2H), 6.90 (d, J=8.8 Hz, 2H), 5.10 (s, 2H), 4.53 (brd s, 1H), 3.34 (brd q, J=6.4 Hz, 2H), 2.74 (t, J=7.0 Hz, 2H), 1.43 (s, 9H).

Example 33

Preparation of N-t-Boc-O-(m,m-dimethyl)benzyl tyramine (38)

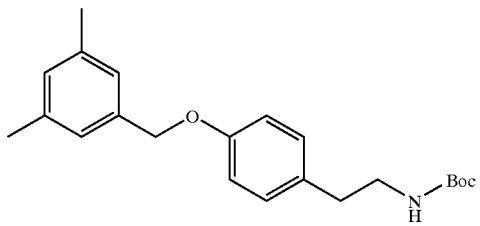

Refer to Method D for the general procedure. The crude product was purified via flash SiO$_2$ chromatography (loaded with DCM, eluted with hexanes/ethyl acetate (20:1) to (10:1)) to give 38 as a white solid (74.7 mg, 40% yield): $^1$H-NMR (400 MHz, chloroform-d) δ 7.10 (d, J=8.8 Hz, 2H), 7.04 (s, 2H), 6.96 (s, 1H), 6.92 (d, J=8.8 Hz, 2H), 4.97 (s, 2H), 4.53 (brd s, 1H), 3.33 (app brd q, J=5.6 Hz, 2H), 2.73 (t, J=6.8 Hz, 2H), 1.43 (s, 9H).

Example 34

Preparation of O-benzyl-tyramine hydrochloride (32)

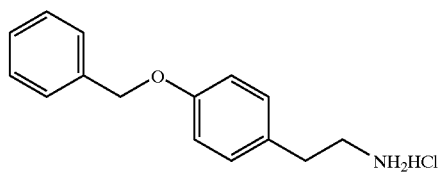

Refer to Method C for the general procedure. The crude reaction mixture was diluted with ether and the white precipitate was collected by vacuum filtration to give 32 as a white solid (156 mg, 97% yield): $^1$H-NMR (400 MHz, DMSO-d$_6$) δ 8.03 (s, 3H), 7.46–7.30 (m, 5H), 7.17 (app d, J=8.8 Hz, 2H), 6.97 (app d, J=8.4 Hz, 2H), 5.08 (s, 2H), 2.97 (app t, J= 7.5 Hz, 2H), 2.81 (app t, J=7.5 Hz, 2H); HRMS (EI+) for C$_{15}$H$_{17}$NO calcd. 227.1310 found 227.1316.

Example 35

Preparation of O-benzyl-3-iodotyramine hydrochloride (39)

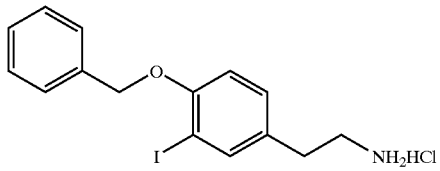

39

Refer to Method C for the general procedure. The crude reaction mixture was diluted with ether and the white precipitate was collected by vacuum filtration to give 36 as a white solid (18.6 mg, 88% yield): $^1$H-NMR (400 MHz, DMSO-$d_6$) δ 7.90 (brd s, 3H), 7.69 (d, J= 2.0 Hz, 1H), 7.48 (d, J=7.2 Hz, 2H), 7.40 (t, J=7.4 Hz, 2H), 7.32 (app t, J=7.2 Hz, 1H), 7.23 (dd, J=8.4, 2.0 Hz, 1H), 7.03 (d, J=8.8 Hz, 1H), 5.17 (s, 2H), 2.99 (brd s, 2H), 2.78 (t, J=7.8 Hz, 2H).

Example 36

Preparation of O-(2-phenyl)ethyl tyramine hydrochloride (40)

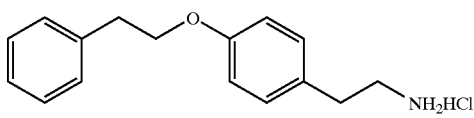

40

Refer to Method C for the general procedure. The crude reaction mixture was diluted with ether and the precipitate was collected by vacuum filtration to give 40 as a white solid (22.4 mg, 93% yield): $^1$H-NMR (400 MHz, DMSO-$d_6$) δ 7.86 (brd s, 3H), 7.16–7.23 (m, 5H), 7.12 (d, J=8.4 Hz, 2H), 6.86 (d. J=8.0 Hz, 2H), 4.13 (t, J=6.8 Hz, 2H), 2.98 (ovrlp t, J= 7.0 Hz, 2H), 2.40 (ovrlp app t, J=8.0 Hz, 2H), 2.75 (app t, J=8.0 Hz, 2H).

Example 37

Preparation of O-(p-fluoro)benzyl tyramine hydrochloride (41)

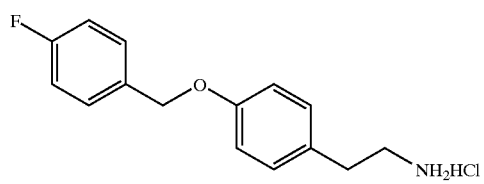

41

Refer to Method C for the general procedure. The crude reaction mixture was diluted with ether and the precipitate was collected by vacuum filtration to give 41 as a white solid (50.4 mg, 90% yield): $^1$H-NMR (400 MHz, DMSO-$d_6$) δ 7.93 (brd s, 3H), 7.45 (app dd, J= 8.4, 5.6 Hz, 2H), 7.22 (ovrlp app t, J=8.8 Hz, 2H), 7.18 (d, J=8.8 Hz, 2H), 6.97 (d, J=8.8 Hz, 2H), 5.07 (s, 2H), 2.98 (app t, J=7.8 Hz, 2H), 2.80 (app t, J=8.0 Hz, 2H).

Example 38

Preparation of O-(m-methoxy)benzyl tyramine hydrochloride (42)

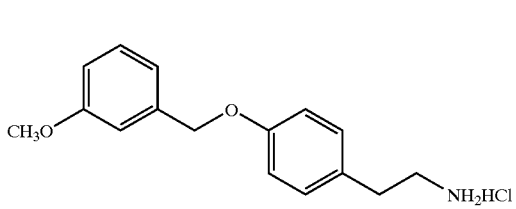

42

Refer to Method C for the general procedure. The crude reaction mixture was diluted with ether and the precipitate was collected by vacuum filtration to give 42 as a white solid (67.0 mg, 97% yield): $^1$H-NMR (400 MHz, DMSO-$d_6$) δ 7.87 (brd s, 3H), 7.30 (t, J=8.0 Hz, 1H), 7.17 (d, J=8.4 Hz, 2H), 6.94–7.20 (m, 4H), 6.88 (app d, J=7.2 Hz, 1H), 5.06 (s, 2H), 3.75 (s, 3H), 2.98 (brd s, 2H), 2.79 (app t, J=7.8 Hz, 2H).

Example 39

Preparation of O-(p-trifluoromethyl)benzyl tyramine hydrochloride (43)

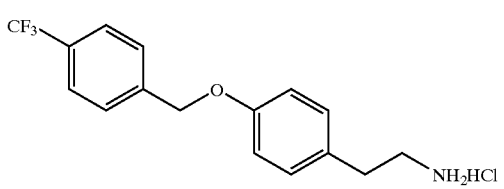

43

Refer to Method C for the general procedure. The crude reaction mixture was diluted with ether and the precipitate was collected by vacuum filtration to give 43 as a white solid (37.3 mg, 84% yield): $^1$H-NMR (400 MHz, DMSO-$d_6$) δ 7.90 (s, 3H), 7.77 (d, J=8.4 Hz, 2H), 7.66 (d, J=8.0 Hz, 2H), 7.19 (d, J=8.8 Hz, 2H), 6.99 (d, J=8.4 Hz, 2H), 5.22 (s, 2H), 2.99 (app t, J=8.0 Hz, 2H), 2.80 (app t, J=7.8 Hz, 2H).

Example 40

Preparation of O-(m,m-dimethyl)benzyl tyramine hydrochloride (44)

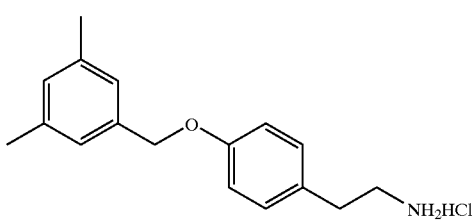

44

Refer to Method C for the general procedure. The crude reaction mixture was diluted with ether and the precipitate was collected by vacuum filtration to give 44 as a white solid (28.6 mg, 86% yield): $^1$H-NMR (400 MHz, chloroform-d) δ 7.97 (brd s, 3H), 7.17 (d, J= 8.4 Hz, 2H), 7.03 (s, 2H), 6.96 (ovrlp d, J=8.4 Hz, 2H), 6.95 (ovrlp s, 1H), 4.99 (s, 2H), 2.97 (brd s, 2H), 2.81 (app t, J=8.0 Hz, 2H), 2.27 (s, 6H).

Method E: General Procedure for N-Alkylated Derivatives

A solution of the requisite protected amine (3.0 mmol) in DMF (5 ml) was added dropwise to a slurry of sodium hydride (150 mg, 3.75 mmol, 60% dispersion in oil) in DMF (10 ml) at 0° C. The reaction was stirred until evolution of hydrogen ceased (10 to 60 min). The desired alkyl halide (7.30 mmol) was then added at 0° C. over 5 minutes and the stirring was continued for an additional 45 minutes. The reaction mixture was allowed to warm to ambient temperature over 2 hours, after which excess sodium hydride was quenched with either methanol (5 ml) or 0.5 m HCl. The mixture was then diluted with ether and sequentially washed with water (3x), brine, then dried over MgSO4. Concentration gave the crude N-alkylated product which was purified as described below.

Example 41

Preparation of
N-t-Boc-N-methyl-O-benzyl-tyramine (45)

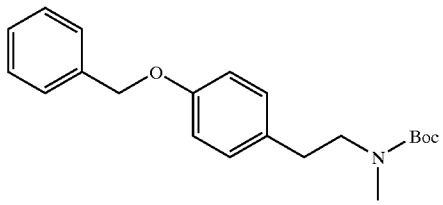

45

Refer to Method E for the general procedure. The crude N-methylated product was purified by flash SiO$_2$ chromatography (loaded with DCM, eluted with hexanes/ethyl acetate (20:1) to (5:1)) to give 45 as a clear oil (0.86 mg, 84% yield): $^1$H-NMR (400 MHz, chloroform-d) δ 7.43–7.31 (m, 5H), 7.07 (brd s, 2H), 6.90 (d, J=8.4 Hz, 2H), 5.04 (s, 2H), 3.37 (brd s, 2H) 2.81 (brd s, 2H) 2.74 (brd s, 3H) 1.40 (s, 9H); HRMS (EI+) for $C_{21}H_{27}NO_3$ calcd. 341.1991 found 341.1983.

Example 42

Preparation of
N-t-Boc-N-methyl-O-benzyl-3-iodotyramine (46)

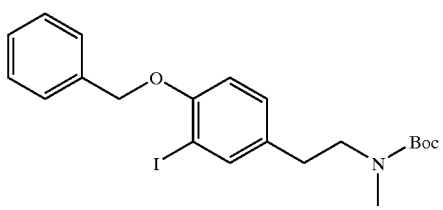

46

Refer to Method E for the general procedure. The crude N-methylated product was purified by flash SiO$_2$ chromatography (loaded with DCM, eluted with hexanes/ethyl acetate (10:1) to (5:1)) to give 46 as a clear oil (0.86 mg, 84% yield): $^1$H-NMR (400 MHz, DMSO-d$_6$) δ 7.62 (d, J=2.0 Hz, 1H), 7.48 (d, J=7.2 Hz, 2H), 7.40 (t, J=7.6 Hz, 2H), 7.32 (appt, J=7.2 Hz, 1H), 7.13 (brd d, J=7.2 Hz, 1H), 6.99 (d, J=8.4 Hz, 1H), 5.16 (s, 2H), 3.32 (obsc brd s, 2H), 2.73 (s, 3H), 2.66 (t, J=7.0 Hz, 2H), 1.36 (brd s, 3H), 1.25 (brd s, 6H)[Note: signals at 1.36 and 1.25 ppm are rotamers of the t-Boc group].

Example 43

Preparation of N-t-Boc-N-ethyl-
O-benzyl-tyramine (47)

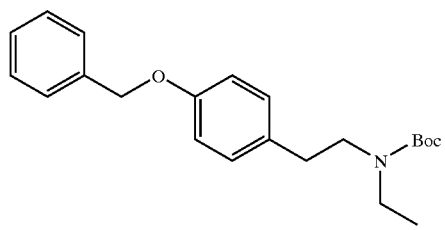

47

Refer to Method E for the general procedure. The crude ethylated product was purified via flash SiO$_2$ chromatography (loaded with DCM, eluted with hexanes/ethyl acetate (100:1) to (10:1)) to give 47 as a slightly yellow oil (123 mg, 80% yield): $^1$H-NMR (400 MHz, chloroform-d) δ 7.43-7.26 (m, 5H), 7.09 (brd s, 2H), 6.89 (d, J=8.4 Hz, 2H), 5.02 (s, 2H), 3.33 (brd s, 2H), 3.19 (brd s, 2H), 2.75 (brd s, 2H), 1.45 (s, 9H), 1.06 (brd t, J=6.2 Hz, 3H).

Example 44

Preparation of N-t-Boc-N-propyl-
O-benzyl tyramine (48)

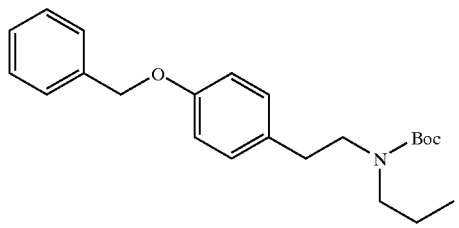

48

Refer to Method E for the general procedure. The crude propylated product was purified via flash SiO$_2$ chromatography (loaded with DCM, eluted with hexanes/ethyl acetate (100:1) to (10:1)) to give 48 as a slightly yellow oil (145 mg, 82% yield): $^1$H-NMR (400 MHz, chloroform-d) δ 7.42–7.20 (m, 5H), 7.09 (brd s, 2H), 6.89 (d, J=8.8 Hz, 2H), 5.02 (s, 2H), 3.32 (brd s, 2H), 3.11 (app brd s, 2H), 2.75 (brd s, 2H), 1.48 (ovlrp brd s, 2H), 1.44 (s, 9H), 0.85 (t, J=7.2 Hz, 3H).

Example 45

Preparation of N-t-Boc-N-butyl-O-benzyl tyramine (49)

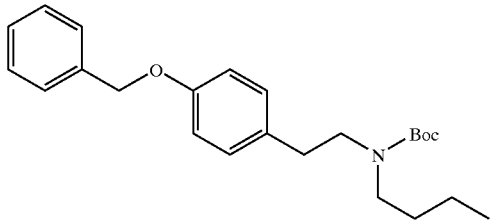

49

Refer to Method E for the general procedure. The crude butylated product was purified via flash $SiO_2$ chromatography (loaded with DCM, eluted with hexanes/ethyl acetate (100:1) to (10:1)) to give 49 as a slightly yellow oil (126 mg, 75% yield): $^1$H-NMR (400 MHz, chloroform-d) δ 7.44–7.30 (m, 5H), 7.09 (brd s, 2H), 6.90 (d, J=8.4 Hz, 2H), 5.04 (s, 2H), 3.32 (brd s, 2H), 3.13 (brd s, 2H), 2.75 (brd s, 2H), 1.45 (s, 1H), 1.27 (sextet, J=7.3 Hz, 2H), 0.90 (t, J=7.4 Hz, 3H).

Example 46

Preparation of N-t-Boc-N-benzyl-O-benzyl tyramine (50)

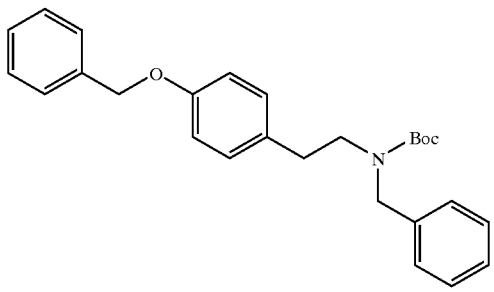

50

Refer to Method E for the general procedure. The crude benzylated product was purified via flash $SiO_2$ chromatography (loaded with DCM, eluted with hexanes/ethyl acetate (100:1) to (10:1)) to give 50 as a slightly yellow oil (167 mg, 80% yield): $^1$H-NMR (400 MHz, chloroform-$d_6$) δ 7.40–7.20 (m, 10H), 7.07 (brd s, 1H), 7.02 (brd s, 1H), 6.88 (d, J=6.4 Hz, 2H), 5.04 (s, 2H), 4.38 (brd s, 1H), 4.31 (brd s, 1H), 3.39 (brd s, 1H), 3.29 (brd s, 1H), 2.75 (brd s, 1H), 2.69 (brd s, 1H), 1.47 (brd s, 9H).

Example 47

Preparation of N-methyl-O-benzyl-tyramine hydrochloride (51)

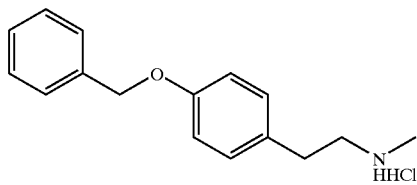

51

Refer to Method C for the general procedure. The crude reaction mixture was concentrated in vacuo to give 51 which was dried under high vacuum (118 mg, 89% yield). $^1$H-NMR 400 MHz, DMSO-$d_6$) δ 8.90 (brd s, 1H), 7.45–7.32 (m, 5H), 7.18 (d, J=8.4 Hz, 2H), 6.75 (d, J=8.4 Hz, 2H), 5.08 (s, 2H), 3.33 (s, 1H) 3.05 (brd s, 2H) 2.86 (t, J=8.8 Hz, 2H) 2.54 (s, 3H).

Example 48

Preparation of N-methyl-O-benzyl-3-iodotyramine hydrochloride (52)

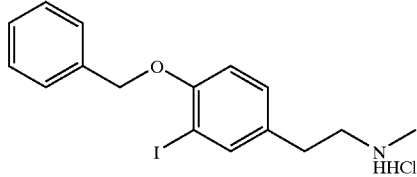

52

Refer to Method C for the general the procedure. The crude reaction mixture was diluted with ether and the white precipitate was collected by vacuum filtration to give 52 as a white solid (35.9 mg, 91% yield): $^1$H-NMR (400 MHz, DMSO-$d_6$) δ 8.64 (brd s, 2H), 7.71 (d, J=2.0 Hz, 1H), 7.49 (d, J=7.2 Hz, 2H), 7.41 (app t, J=7.3 Hz, 2H), 7.33 (app t, J=7.4 Hz, 1H), 7.24 (dd, J=8.2, 2.2 Hz, 1H), 7.05 (d, J=8.4 Hz, 1H), 5.18 (s, 2H), 3.10 (brd s, 2H), 2.83 (app t, J=7.8 Hz, 2H), 2.55 (brd s, 3H).

Example 49

Preparation of N-ethyl-O-benzyl tyramine hydrochloride (53)

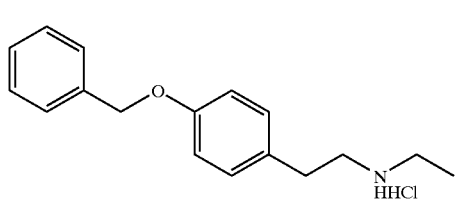

53

Refer to Method C for the general procedure. The crude reaction mixture was diluted with ether and the white precipitate was collected by vacuum filtration to give 53 as a white solid (38.9 mg, 92% yield): $^1$H-NMR (400 MHz, DMSO-d$_6$) δ 8.70 (brd s, 2H), 7.45–7.30 (m, 5H), 7.18 (d, J=8.4 Hz, 2H), 6.97 (d, J=8.4 Hz, 2H), 5.09 (s, 2H), 3.08 (app t, J= 7.6 Hz, 2H), 2.95 (q, J=7.2 Hz, 2H), 2.85 (app t, J=8.2 Hz, 2H), 1.19 (t, J=7.2 Hz, 3H).

Example 50

Preparation of N-propyl-O-benzyl tyramine hydrochloride (54)

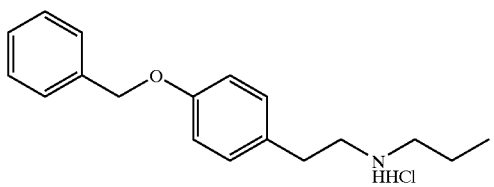

54

Refer to Method C for the general procedure. The crude reaction mixture was diluted with ether and the white precipitate was collected by vacuum filtration to give 54 as a white solid (35.9 mg, 88% yield): $^1$H-NMR (400 MHz, DMSO-d$_6$) δ 8.72 (brd s, 2H), 7.45–7.30 (m, 5H), 7.17 (d, J=8.4 Hz, 2H), 6.98 (d, J=8.8 Hz, 2H), 5.09 (s, 2H), 308 (app t, J= 8.2 Hz, 2H), 2.89–2.84 (m, 4H), 1.62 (sextet, J=7.5 Hz, 2H), 0.91 (t, J=7.6 Hz, 3H).

Example 51

Preparation of N-butyl-O-benzyl tyramine hydrochloride (55)

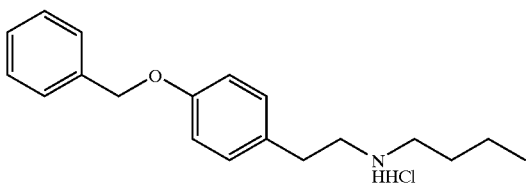

55

Refer to Method C for the general procedure. The crude reaction mixture was diluted with ether and the white precipitate was collected by vacuum filtration to give 55 as a white solid (32.1 mg, 91% yield): $^1$H-NMR (400 MHz, DMSO-d$_6$) δ 8.71 (brd s, 2H), 7.45–7.30 (m, 5H), 7.17 (d, J=8.8 Hz, 2H), 6.98 (d, J=8.8 Hz, 2H), 5.09 (s, 2H), 3.08 (app t, J= 8.2 Hz, 2H), 2.92–2.84 (m, 4H), 1.58 (quintet, J=7.7 Hz, 2H), 1.33 (sextet, J=7.4 Hz, 2H), 0.89 (t, J=7.2 Hz, 3H).

Example 52

Preparation of N-benzyl-O-benzyl tyramine hydrochloride (56)

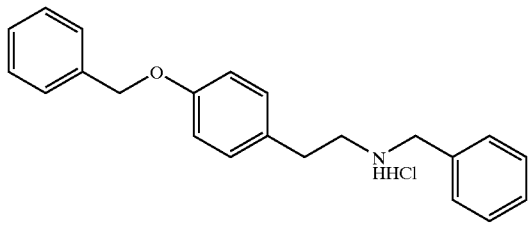

56

Refer to Method C for the general procedure. The crude reaction mixture was diluted with ether and the white precipitate was collected by vacuum filtration to give 56 as a white solid (66.2 mg, 85% yield): $^1$H-NMR (400 MHz, DMSO-d$_6$) δ 9.21 (brd s, 2H), 7.56–7.30 (m, 10H), 7.16 (d, J=8.4 Hz, 2H), 6.97 (d, J=8.4 Hz, 2H), 5.08 (s, 2H), 4.16 (brd s, 2H), 3.09 (brd s, 2H), 2.91 (app t, J=8.2, 2H).

Example 53

Thyronamine Derivatives and Analogs Mediate Rapid Physiologic Action Via Trace Amine Receptors The biological activity of thyroid hormones are generally mediated by the nuclear thyroid hormone receptors (TRs). However, certain physiological actions of thyroid hormone occur rapidly (in a matter of seconds), and therefore cannot be accounted for transcriptional regulation by TRs.

Biogenic amines such as dopamine, norepinephrine, and seratonin mediate rapid responses through activation of their cognate receptors, which belong to the 7-transmembrane containing G-protein coupled receptor (GPCR) superfamily. These biogenic amines are synthesized from their corresponding amino acids by an enzymatic sequence that involves decarboxylation of the amino acid as the key step that generates the arylethylamine substructure common to this group of signaling molecules. For example, the decarboxylation reaction that provides dopamine from L-DOPA (FIG. 2) is catalyzed by the non-selective enzyme aromatic amino acid decarboxylase (AAD), which also catalyzes the conversion of histadine to histamine and 5-hydroxytryptophan to seratonin. In fact, AAD is known to catalyze the decarboxylation of a wide variety of natural and synthetic aromatic amino acids, apparently requiring an aromatic group linked to an alanine amino acid as the key feature of substrate recognition.

Figure 2:
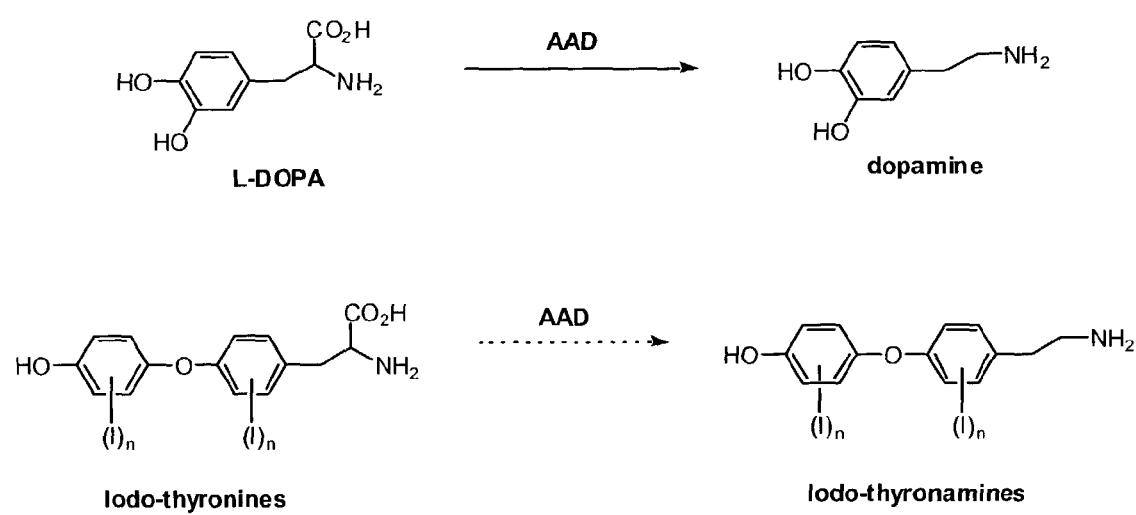
Figure 3:
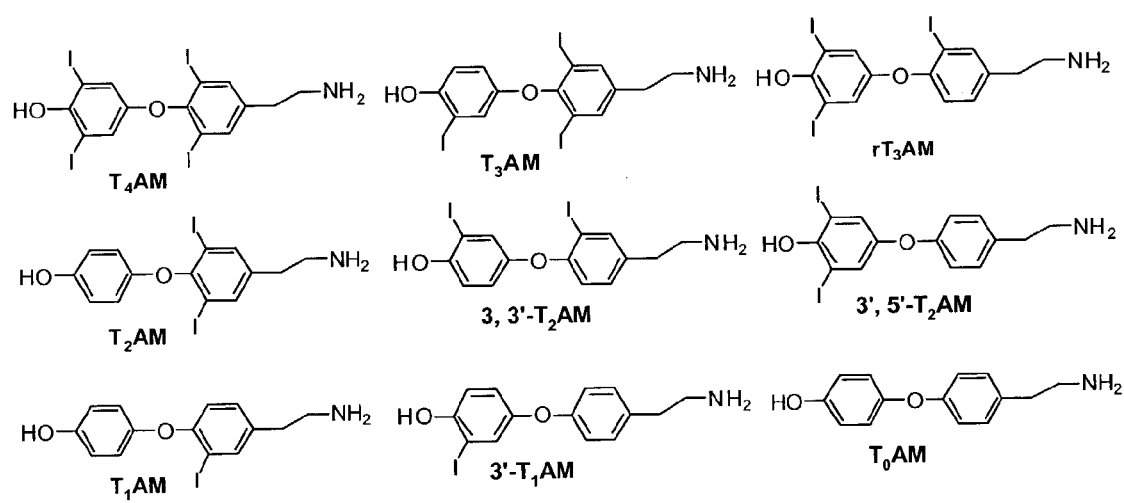
FIG. 3. Thyronamine synthetic products
FIG. 4. Dose-response for thyronamines on the trace amine receptor (rTAR-1).

Thyroid hormones, i.e. $T_3$ and $T_4$ as well as the lower iodination state metabolites (FIG. 1), can be substrates for AAD, giving rise to the aryl ethylamine compounds hereafter referred to as thyronamine derivatives and analogs or as iodo-thyronamines (FIG. 2). On the basis of the structural similarity between the iodo-thyronamines and dopamine, one or more of these iodo-thyronamines activating a cognate iodo-thyronamine GPCR can constitute a new signaling pathway to mediate rapid effects of thyroid hormone. In an embodiment, chemical synthesis of a panel of thyronamines is shown in FIG. 3, the members of which correspond to every possible iodination state between thyroxamine (T$_4$AM) and thyronamine (T$_0$AM). From this panel, T$_4$AM, T$_3$AM, and T$_0$AM have been described previously. See, for example, Thibault, O., 1951 *C. R. Soc. Chim. biol.*, 797–800; Meyer, T., 1983, *Horm. metabol. Res.* 15: 602–606; Buu-Hoi, 1966, *Med. Pharmacol. exp.* 15: 17–23. The other six iodothyronamines in the panel have not been described previously. The synthesis of iodothyronamines, T$_1$AM, T$_2$AM, 3'-T$_1$AM, 3,3'-T$_2$AM, 3,5'-T$_2$AM, and rT$_3$AM have not been previously synthesized or described in the literature.

A physiological role for iodo-thyronamines can be reasoned as follows: (1) Thyroid hormones are aromatic amino acids ultimately derived from tyrosine; (2) Thyroid hormones are chemically and biosynthetically similar to L-DOPA and 5hydroxytryptophan, the biosynthetic precursors of the neurotransmitters dopamine, norepinephrine, and serotonin (5-hydroxytryptamine), respectively; (3) The AAD-catalyzed decarboxylation of L-DOPA gives rise to the neurotransmitter dopamine as shown in FIG. 2. Since AAD is a non-selective enzyme that will promote the efficient decarboxylation of a wide variety of aromatic amino acids, the thyroid hormones (T$_4$, T$_3$) and their deiodinated metabolites (shown in FIG. 1), are effective substrates for AAD resulting in iodo-thyronamine products (FIG. 2); (4) These iodothyronamines would be ligands for membrane bound receptors, for example, G-protein coupled receptors (GPCRs), and iodo-thyronamine induced activation of these receptors could be responsible for the rapid signaling effects of thyroid hormone.

The cloning and characterization of a rat receptor (subsequently from mice and human also) that is activated by several biogenic trace amines has been reported. See, e.g., Bunzow, et al., 2001, *Mol. Pharmacol.* 60: 1181–1188; Borowsky, et al., 2001, *Proc. Natl. Acad. Sci.* 98: 8966–8971. This receptor is designated as trace amine receptor (TAR), a 7-transmembrane G protein coupled receptor (GPCR) and a homolog of catecholamine and 5-hydroxytryptophan receptors. Multiple subtypes exist: 15 rat TARs and 5 human TARs. TARs are expressed in tissues including, but not limited to brain, heart, pancreas, kidney, stomach, small intestine, skeletal mucle, prostate, liver, and spleen.

In an embodiment, metabolites of thyroid hormone, for example, thyronamines and iodo-thyronamines, bind to rTAR. Using a cAMP assay, thyroid hormone metabolites, e.g., 3-iodothyronamine, bind to the TAR receptor with high affinity (in the same range as the natural ligands). Thyroid hormone metabolites, e.g., 3-iodothyronamine, are also present in the crude extract of rat and mouse brain. Finally, the rapid action of the thyroid hormone metabolite, e.g., 3-iodothyronamine, was demonstrated in a physiological heart model system (13–19 day old chick embryo). For example, 3-iodothyronamine, or more stable and potent synthetic analogs, can be useful for treating cardiovascular disorders such as congestive heart failure. Additionally, these compounds could also have many other uses as therapeutics for diseases related to thyroid hormone status.

Example 54

Thyronamine Derivatives and Analogs Mediate Rapid Physiologic Action Via Trace Amine Receptors The biological activity of thyroid hormones are generally mediated by the nuclear thyroid hormone receptors (TRs). However, certain physiological actions of thyroid hormone occur rapidly (in a matter of seconds), and therefore cannot be accounted for transcriptional regulation by TRs.

Biogenic amines such as dopamine, norepinephrine, and seratonin mediate rapid responses through activation of their cognate receptors, which belong to the 7-transmembrane containing G-protein coupled receptor (GPCR) superfamily. These biogenic amines are synthesized from their corresponding amino acids by an enzymatic sequence that involves decarboxylation of the amino acid as the key step that generates the arylethylamine substructure common to this group of signaling molecules. For example, the decarboxylation reaction that provides dopamine from L-DOPA (FIG. 2) is catalyzed by the non-selective enzyme aromatic amino acid decarboxylase (AAD), which also catalyzes the conversion of histadine to histamine and 5-hydroxytryptophan to seratonin. In fact, AAD is known to catalyze the decarboxylation of a wide variety of natural and synthetic aromatic amino acids, apparently requiring an aromatic group linked to an alanine amino acid as the key feature of substrate recognition.

Thyroid hormones, i.e. T$_3$ and T$_4$ as well as the lower iodination state metabolites (FIG. 1), can be substrates for AAD, giving rise to the aryl ethylamine compounds hereafter referred to as thyronamine derivatives and analogs or as iodo-thyronamines (FIG. 2). On the basis of the structural similarity between the iodo-thyronamines and dopamine, one or more of these iodo-thyronamines activating a cognate iodo-thyronamine GPCR can constitute a new signaling pathway to mediate rapid effects of thyroid hormone. In an embodiment, chemical synthesis of a panel of thyronamines is shown in FIG. 3, the members of which correspond to every possible iodination state between thyroxamine (T$_4$AM) and thyronamine (T$_0$AM). From this panel, T$_4$AM, T$_3$AM, and T$_0$AM have been described previously. See, for example, Thibault, O., 1951 *C. R. Soc. Chim. biol.*, 797–800; Meyer, T., 1983, *Horm. metabol. Res.* 15: 602–606; Buu-Hoi, 1966, *Med. Pharmacol. exp.* 15: 17–23; Stohr, R., 1931, *Hoppe-Seyler Z. physiol. Chem.* 201, 142; Petit and Buu-Hoi, 1961, *J. org. Chem.* 26, 3832; Cody et al., 1984, *Endocrine Research*, 10, 91–99. The other six iodo-thyronamines in the panel have not been described previously. The synthesis of iodo-thyronamines, T$_1$AM, T$_2$AM, 3'-T$_1$AM, 3,3'-T$_2$AM, 3,5'-T$_2$AM, and rT$_3$AM have not been previously synthesized or described in the literature.

A physiological role for iodo-thyronamines can be reasoned as follows: (1) Thyroid hormones are aromatic amino acids ultimately derived from tyrosine; (2) Thyroid hormones are chemically and biosynthetically similar to L-DOPA and 5-hydroxytryptophan, the biosynthetic precursors of the neurotransmitters dopamine, norepinephrine, and serotonin (5-hydroxytryptamine), respectively; (3) The AAD-catalyzed decarboxylation of L-DOPA gives rise to the neurotransmitter dopamine as shown in FIG. 2. Since AAD is a non-selective enzyme that will promote the efficient decarboxylation of a wide variety of aromatic amino acids, the thyroid hormones (T$_4$, T$_3$) and their deiodinated metabolites (shown in FIG. 1), are effective substrates for AAD resulting in iodo-thyronamine products (FIG. 2); (4) These iodothyronamines would be ligands for membrane bound receptors, for example, G-protein coupled receptors (GPCRs), and iodo-thyronamine induced activation of these receptors could be responsible for the rapid signaling effects of thyroid hormone.

The cloning and characterization of a rat receptor (subsequently from mice and human also) that is activated by several biogenic trace amines has been reported. See, e.g., Bunzow, et al., 2001, *Mol. Pharmacol.* 60: 1181–1188; Borowsky, et al., 2001, *Proc. Natl. Acad. Sci.* 98: 8966–8971. This receptor is designated as trace amine receptor (TAR), a 7transmembrane G protein coupled receptor (GPCR) and a homolog of catecholamine and 5-hydroxytryptophan receptors. Multiple subtypes exist: 15 rat TARs and 5 human TARs. TARs are expressed in tissues including, but not limited to brain, heart, pancreas, kidney, stomach, small intestine, skeletal muscle, prostate, liver, and spleen.

In an embodiment, metabolites of thyroid hormone, for example, thyronamines and iodo-thyronamines, bind to rTAR. Using a cAMP assay, thyroid hormone metabolites, e.g., 3-iodothyronamine, bind to the TAR receptor with high affinity (in the same range as the natural ligands). Thyroid hormone metabolites, e.g., 3-iodothyronamine, are also present in the crude extract of rat and mouse brain. Finally, the rapid action of the thyroid hormone metabolite, e.g., 3-iodothyronamine, was demonstrated in a physiological heart model system (13–19 day old chick embryo). For example, 3-iodothyronamine, or more stable and potent synthetic analogs, can be useful for treating cardiovascular disorders such as congestive heart failure. Additionally, these compounds could also have many other uses as therapeutics for diseases related to thyroid hormone status.

Example 55

Functional Role for Thyronamine Derivatives and Analogs as Signaling Molecules in an in Vitro Rat Trace Amine Receptor (TAR) Assay A G-protein coupled receptor (GPCR) called the trace amine receptor (TAR-1) belongs to the subfamily of receptors for biogenic amines. TAR-1 is homologous to receptors for dopamine, norephinephrine, and serotonin (5-hydroxytryptamine), but these biogenic amines are not potent agonists of TAR-1. Instead, TAR-I has been found to respond to endogenous trace amines such as p-tyramine, 3-methoxy-p-tyramine, and phenethylamine, as well as a variety of synthetic phenethylamine derivatives. TAR-1 couples to $G\alpha_s$ in response to these agonists resulting in cAMP accumulation in cells expressing TAR-1. See, e.g., Bunzow, et al., 2001, *Mol. Pharmacol.* 60: 1181–1188; Borowsky, et al., 2001, *Proc. Natl. Acad. Sci.* 98: 8966–8971.

Figure 4:
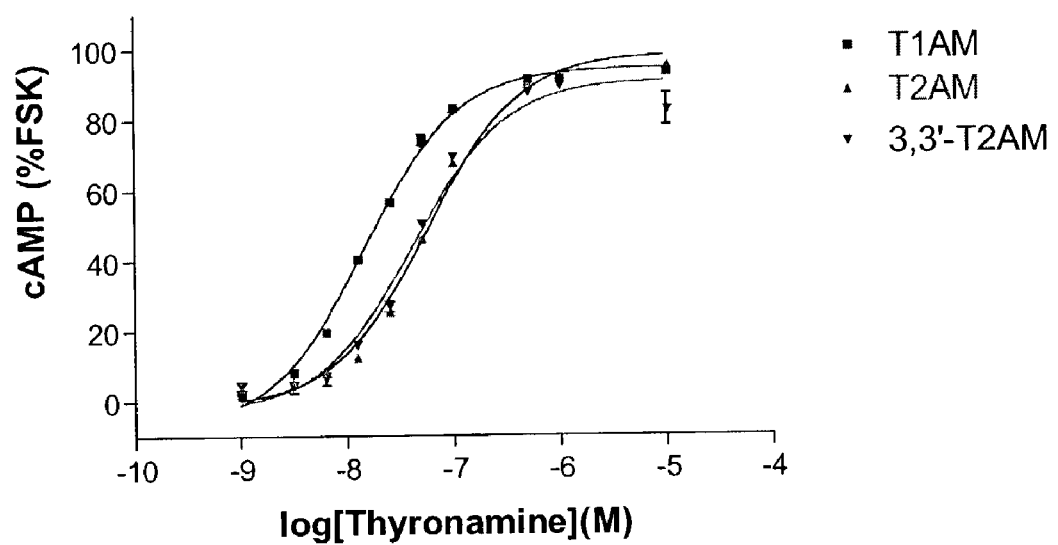

Given the chemical similarity between iodo-thyronamines and biogenic amines, and because TAR-1 belongs to the biogenic amine GPCR subfamily whose endogenous agonist remains to be established, TAR-1 is an ideal candidate receptor for iodo-thyronamines. To test this, the synthetic iodo-thyronamines were assayed for their ability to stimulate cAMP accumulation in human embryonic kidney (HEK) cells stably expressing rTAR-1, as well as cells transfected with an empty vector. None of the compounds tested had any effect on cAMP accumulation in the cells that received empty vector. However, several of the iodo-thyronamines were found to stimulate cAMP accumulation in the rTAR-1 expressing cells in a dose-dependent fashion (FIG. 4). To address the issue of receptor selectivity, all of the iodo-thyronamines were tested for their ability to activate the dopamine receptors and the β-adrenergic receptors. As with rTAR-1, HEK cells stably expressing either $D_1R$ or $β_2AR$ (both $G\alpha_s$ coupled) were treated with the panel of iodo-thyronamines and no ligand stimulation of cAMP accumulation was found (data not shown), demonstrating that the iodo-thyronamines are not promiscuous agonists of catecholamine receptors.

The potency index of effective concentration for half-maximal stimulation ($EC_{50}$) of rTAR-1 was calculated from the dose-response curve for each compound (Table 1). The spectrum of potencies across the thyronamine series demonstrates that the specific number and placement of iodine atoms influences potency in a critical way. 3-iodothyronamine ($T_1AM$) is the most potent rTAR-1 agonist with an $EC_{50}$ of 14 nM, and thyronamine ($T_0AM$) is the least potent agonist with an $EC_{50}$ of 131 nM. Thus, addition of a single iodine atom to the 3-position of $T_0AM$ results in an approximate 10-fold increase in agonist potency for rTAR-1. All other combinations of iodines on the thyronamine skeleton result in decreased potency. $T_4AM$ and $rT_3AM$ showed no ability to stimulate cAMP accumulation in this assay further demonstrating that potent iodo-thyronamine activation of rTAR-1 follows specific requirements regarding number and regiochemical positioning of iodines within the thyronamine carbon skeleton.

We also tested the panel of iodo-thyronamines for activation of the mouse TAR-1 and found that $T_1AM$ was again the most potent agonist in the collection (Table 1). The $EC_{50}$ value for $T_1AM$ activation of mTAR-1 is 112 nM, and the only other iodo-thyronamine with an $EC_{50}$ value less than 1 $\mu$M against mTAR-1 is $T_2AM$. The observed potency for $T_1AM$ compares favorably to the potency of other biogenic amines activating their cognate GPCRs. For example, in similar cell-culture based assays, $EC_{50}$ values ranging from 2 to 275 nM have been reported for dopamine activation of dopamine receptors. The differences in potency of $T_1AM$ as well as the rank order potency of the other thyronamines in the series are manifestations of each species specific TAR-1 polypeptide sequence which should inform future molecular structure-activity studies.

TABLE 1

Rank Order Potencies of Iodo-Thyronamine Activation of rTAR-1

| Compound Name | Rat TAR $EC_{50}$ (nM) |
| --- | --- |
| 3-iodothyronamine ($T_1AM$) | 14 |
| 3,3'-diodothyronamine (3,3'-$T_2AM$) | 41 |
| 3,5-diodothyronamine ($T_2AM$) | 56 |
| 3,5,3'-tri-iodothyronamine ($T_3AM$) | 87 |
| thyronamine ($T_0AM$) | 131 |
| 3,3',5'-triodothyronamine ($rT_3AM$) | >1000 |
| thyroxamine ($T_4AM$) | >1000 | cAMP Assay. HEK293 cells were harvested in Krebs-Ringer-HEPES buffer (KRH) and preincubated in KRH with 200 $\mu$M 3-isobutyl-methylxanthine. For drug treatments, cells were incubated in KRH with 100 $\mu$M 3-isobutyl-1-methylxanthine with the test compound (or 10 [M forskolin) for 1 hour at 37° C. The cells were then boiled for 20 minutes after adding an equal volume of 0.5 mM sodium acetate buffer, centrifuged to remove cell debris, and the resulting extract was analyzed for cAMP content using competitive binding of [$^3$H]cAMP to a cAMP binding protein (Diagnostic Products Corp., Los Angeles, Calif.). Data were normalized according to protein content as determined using the Bradford reagent (Bio-Rad). Concentration-response curves were plotted and $EC_{50}$ values calculated with Prism software (GraphPad, San Diego, Calif.).

Example 56

Identification of 3-Iodo-Thyronamine, T$_1$AM, in Rat, Mouse, and Guinea Pig Brain To investigate whether 3-iodothyronamine, T$_1$AM, the most potent iodothyronamine found to activate TAR-1, was a naturally occurring metabolite, liquid chromatography/mass spectrometry (LC/MS) was performed on rat brain. Rat whole brain homogenates were prepared in 0.1 M perchloric acid (PCA), conditions that are standard for the extraction of biogenic amines such as dopamine. The crude extracts were analyzed by liquid chromatography/mass spectrometry (LC/MS) using an elution and detection protocol that was optimized with the synthetic T$_1$AM standard. The mass spectrometer for these studies was a triple quadrapole MS/MS instrument that is ideal for single ion monitoring in complex biological mixtures. Nevertheless, no T$_1$AM was detected in crude PCA brain homogenates using this method.

Figure 5A:
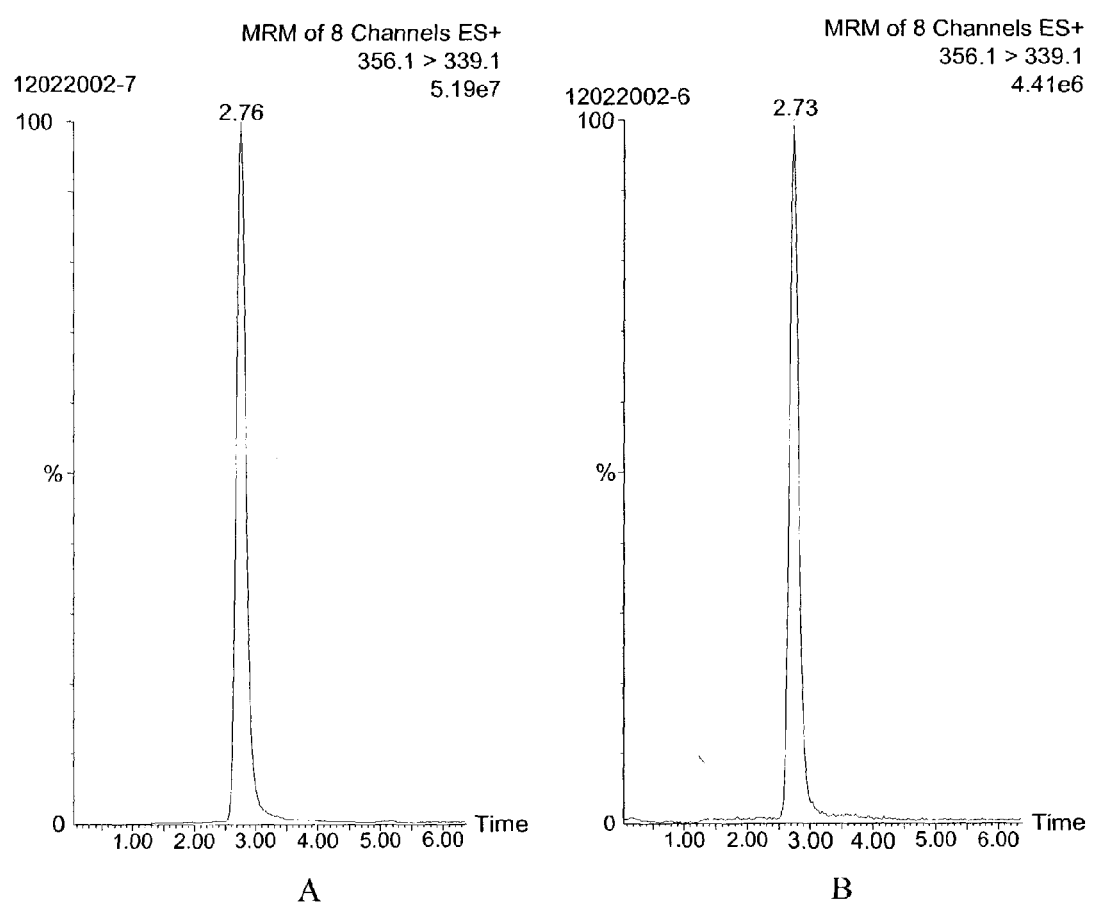
Figure 5B:
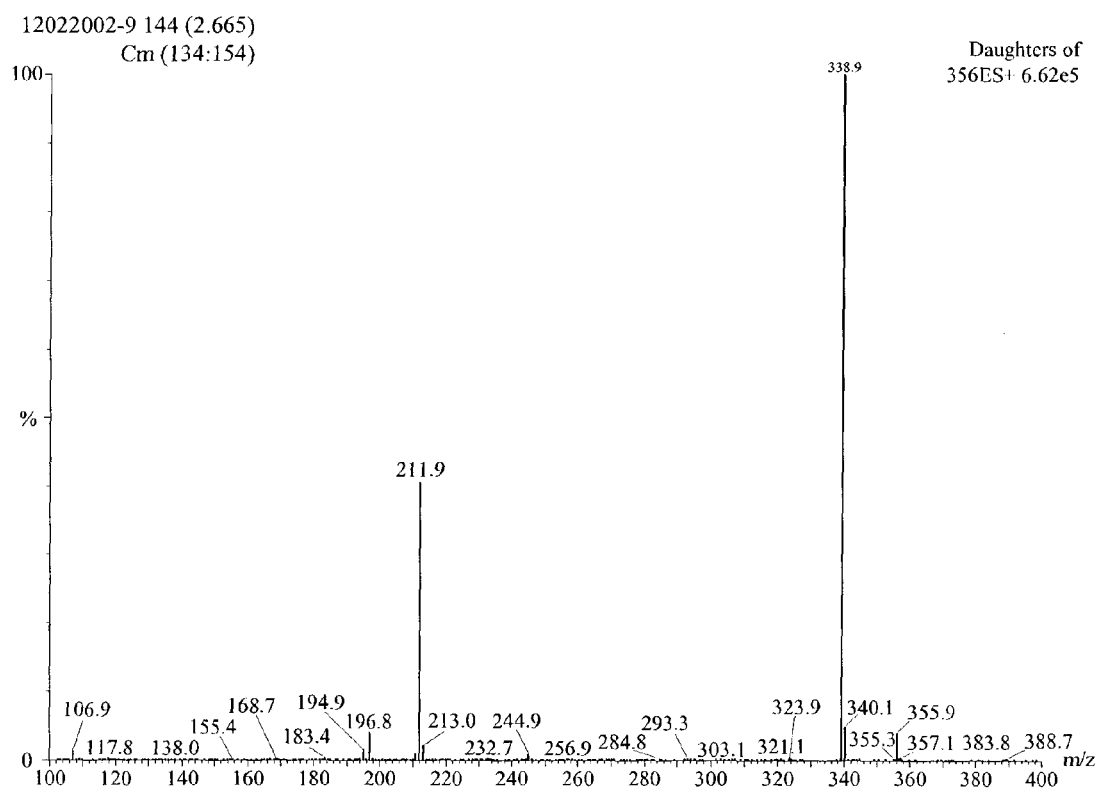
Figure 5B:
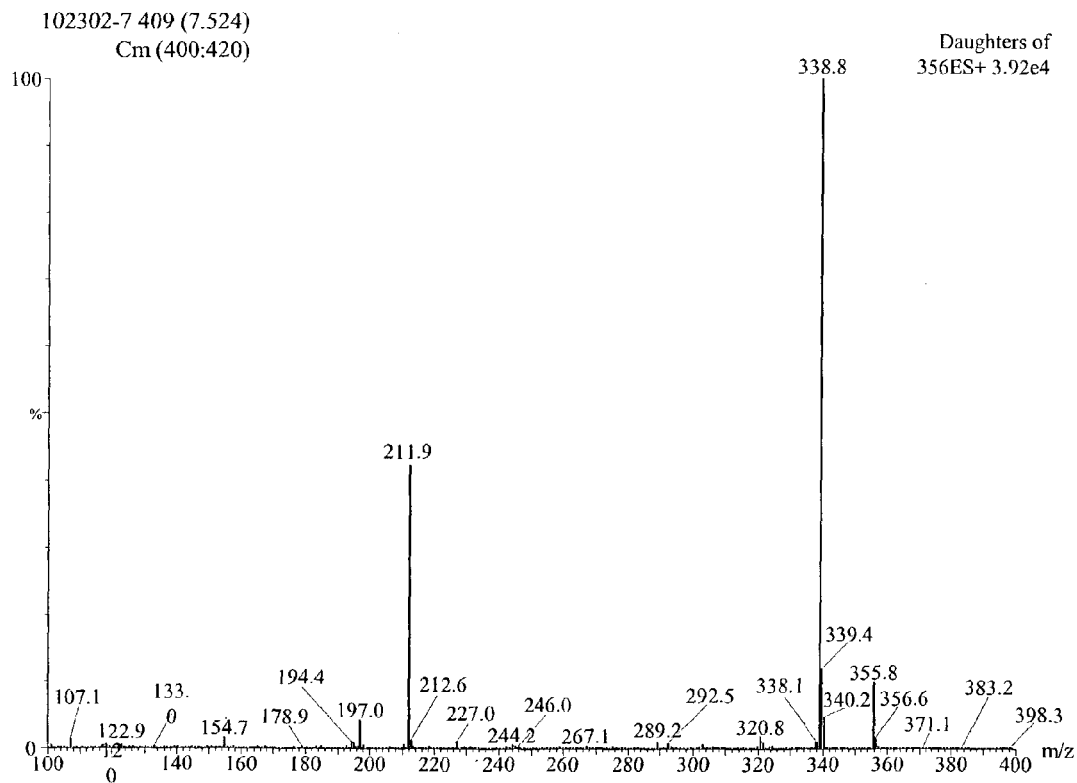

The detection limit of this system is about 50 fmol, leading one to conclude that T$_1$AM is present in whole brain extracts below this limit. Accordingly, an alternative extraction procedure was developed: (i) adjusting the pH of PCA homogenate to pH 12, (ii) extracting the free-base biogenic amines with ethyl acetate, (iii) concentrating the ethyl acetate fraction to dryness, and (iv) dissolving the concentrated residue in $\frac{1}{100}$ the initial volume of 0.1 M PCA. Analysis of this concentrated and partially purified brain extract unambiguously revealed the presence of T$_1$AM (FIG. 5). The endogenous T$_1$AM identified from the brain extract was found to be chemically identical to the synthetic T$_1$AM standard in terms of HPLC column retention time, parent ion mass (356) and first daughter ion mass (339) corresponding to loss of ammonia (FIG. 5B). A second daughter ion common to both synthetic and biological samples of 212 m/e, corresponding to loss of iodide from the first daughter ion, confirms the presence of iodine in both samples. Moreover, the Q1 and Q3 mass spectra of both the synthetic and biologically derived T$_1$AM were identical (FIGS. 5B,C), providing further confirmation that T$_1$AM is biogenic amine. T$_1$AM in rat brain is approximately 600 fmol per rat brain or approximately 200 fmol per gram of rat brain. T$_1$AM level is approximately 3 to 20% of T$_4$ level in rat brain. In addition to rat brain, T$_1$AM in brain extracts from mouse and guinea pig has been detected using this protocol (data not shown).

These data verify that T$_1$AM is a naturally occurring biogenic amine. Since T$_1$AM contains an iodine atom attached to the elements of a thyronine carbon skeleton, and since thyroid hormone is the only organically bound source of iodine in vertebrates, there is little doubt that T$_1$AM is an endogenous metabolite of thyroid hormone. The dual action of amino acid decarboxylase (AAD) and deiodinases on T$_4$ represents the simplest pathway of metabolic reactions that produce T$_1$AM from thyroid hormone.

Figure 6A:
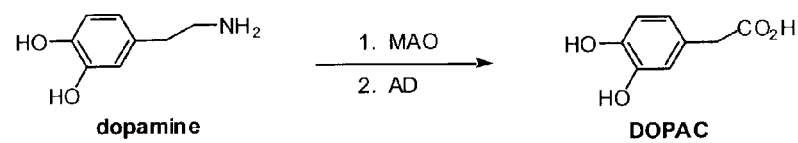
FIG. 6A, 6B Metabolites of dopamine and $T_1$amine from sequential action of monoamine oxidase and aldehyde dehydrogenase.
Figure 6B:
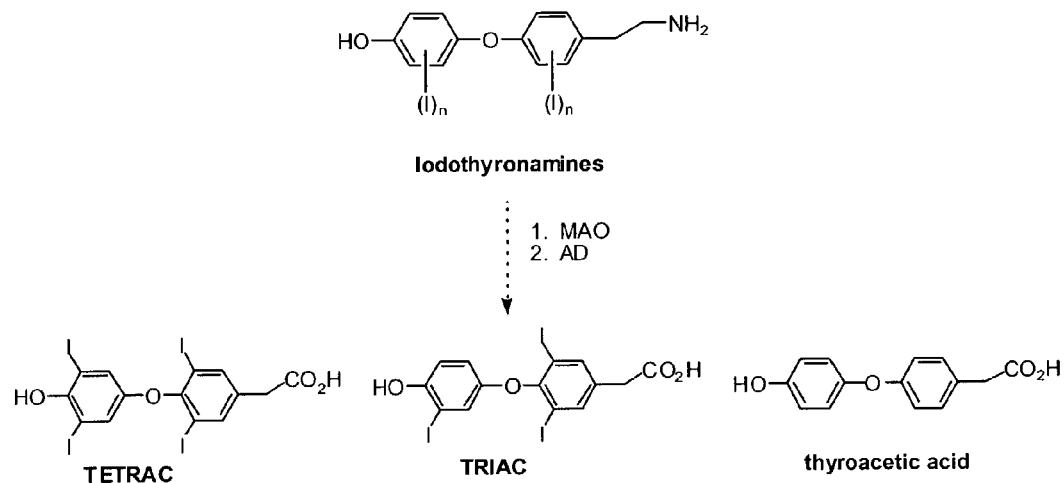

Like dopamine, T$_1$AM is a biogenic amine that contains the phenethylamine substructure and should be a substrate for the non-selective amine-degrading enzyme, monoamine oxidase (MAO). One of the primary metabolites of dopamine is DOPAC (FIG. 6A), which arises from the sequential action of MAO and aldehyde dehydrogenase on dopamine. It is interesting to note that similar aryl acetic acid metabolites of thyroid hormone have been known for some time, including the compounds TETRAC, TRIAC, and thyroacetic acid (FIG. 6B), and a definitive account of the enzymatic processing that gives rise to these metabolites has not been reported. On the basis of the demonstration that T$_1$AM is naturally occurring, it is reasonable to postulate that other thyronamines with different iodine content such as T$_4$AM, T$_3$AM, and T$_0$AM are also present endogenously. This provides a concise metabolic route for the formation of the aryl acetic acid metabolites of thyroid hormone; the corresponding thyronamines are processed in the same way as dopamine by the non-selective action of MAO and aldehyde dehydrogenase.

Example 57

Figure 7:
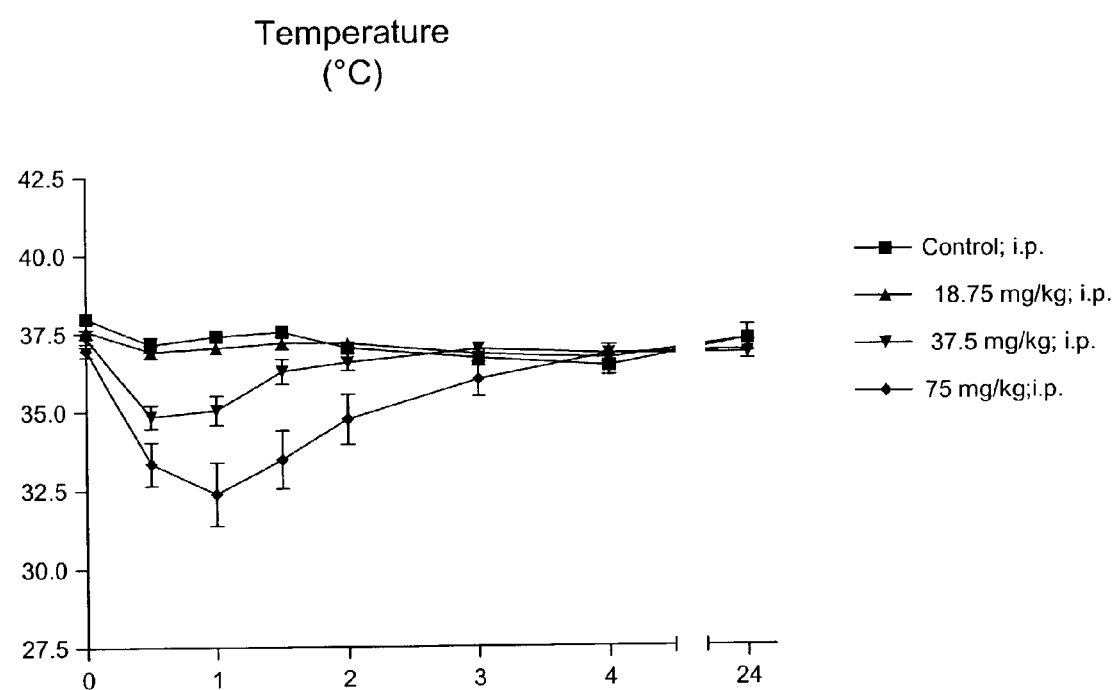
FIG. 7: Graph of core body temperature (° C.) vs. time (hours) following intraperitoneal injection into mice (n=8) of an iodo-thyronamine compound, $T_1$amine.

Function of 3-Iodo-Thyronamine, T$_1$AM, on Core Body Temperature of Mice Injected Intraperitoneally or Intracerebrally Eight week old male C57 Black 6J (C57B1/6J) mice were injected intraperitoneally (i.p.) with the indicated dose of 3-iodothyronamine (T$_1$AM) dissolved in 60% DMSO and normal saline (pH 7.4). Mice were injected intraperitoneally with a dose of T$_1$AM at 18.75, 37.5, or 75 mg/kg body weight. Core body temperature was measured as rectal temperature every 30 minutes for the first 2 hours and then again at 3, 4, and 24 hours post injection. The core body temperature response (with standard error) to each dose reflects the response of 7–8 mice in a room maintained at 24° C. See FIG. 7.

Figure 8:
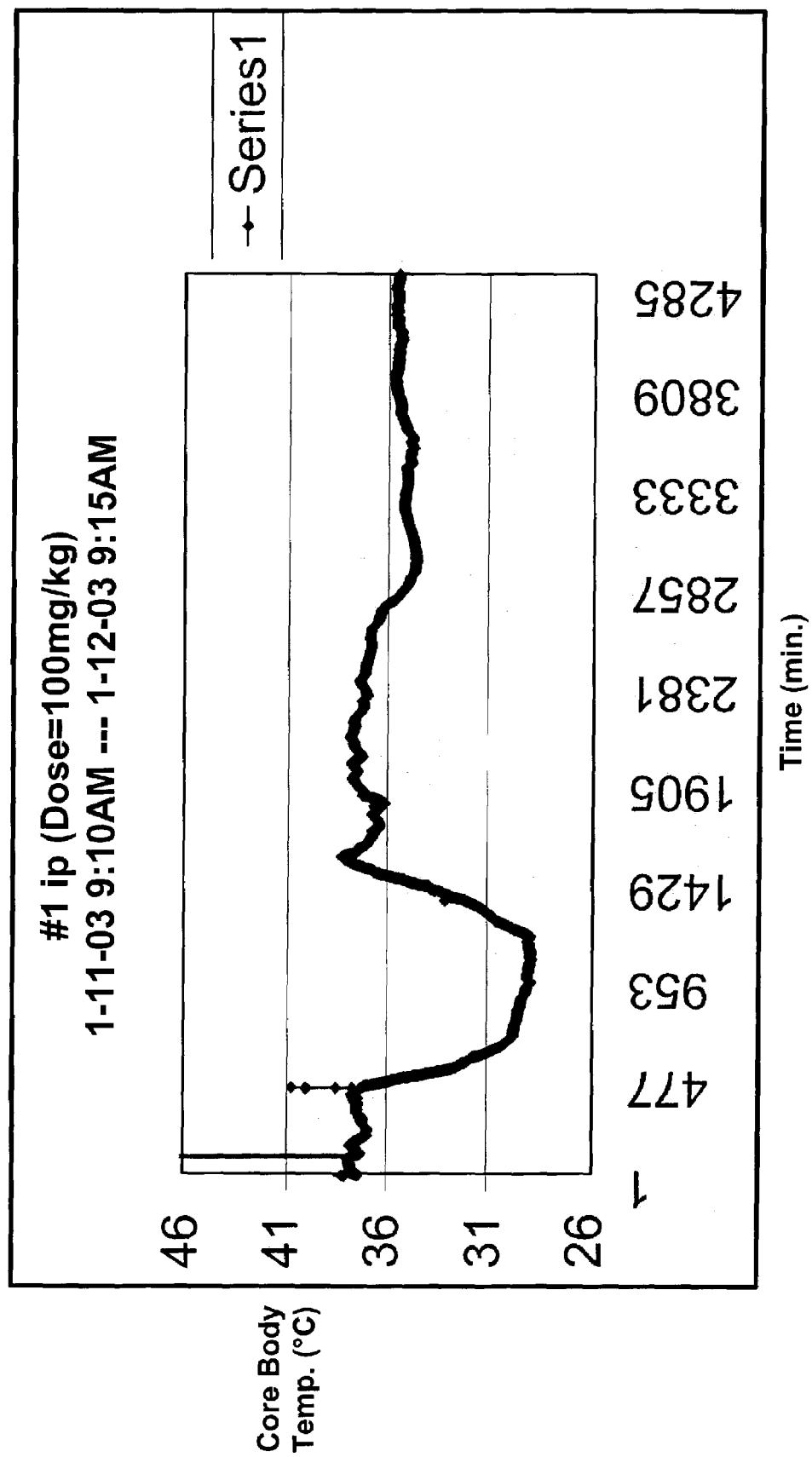
FIG. 8: Graph of core body temperature (° C.) vs. time (hours) following intraperitoneal injection into a mouse of an iodo-thyronamine compound, $T_1$amine.

Core body temperature response was measured in an adult male C57B1/6J mouse injected intraperitoneally with a dose of T$_1$AM at 100 mg/kg T$_1$AM. The mouse was implanted with a telemetry-emitting temperature sensing probe for more accurate measurement of core body temperature. See FIG. 8.

Figure 9:
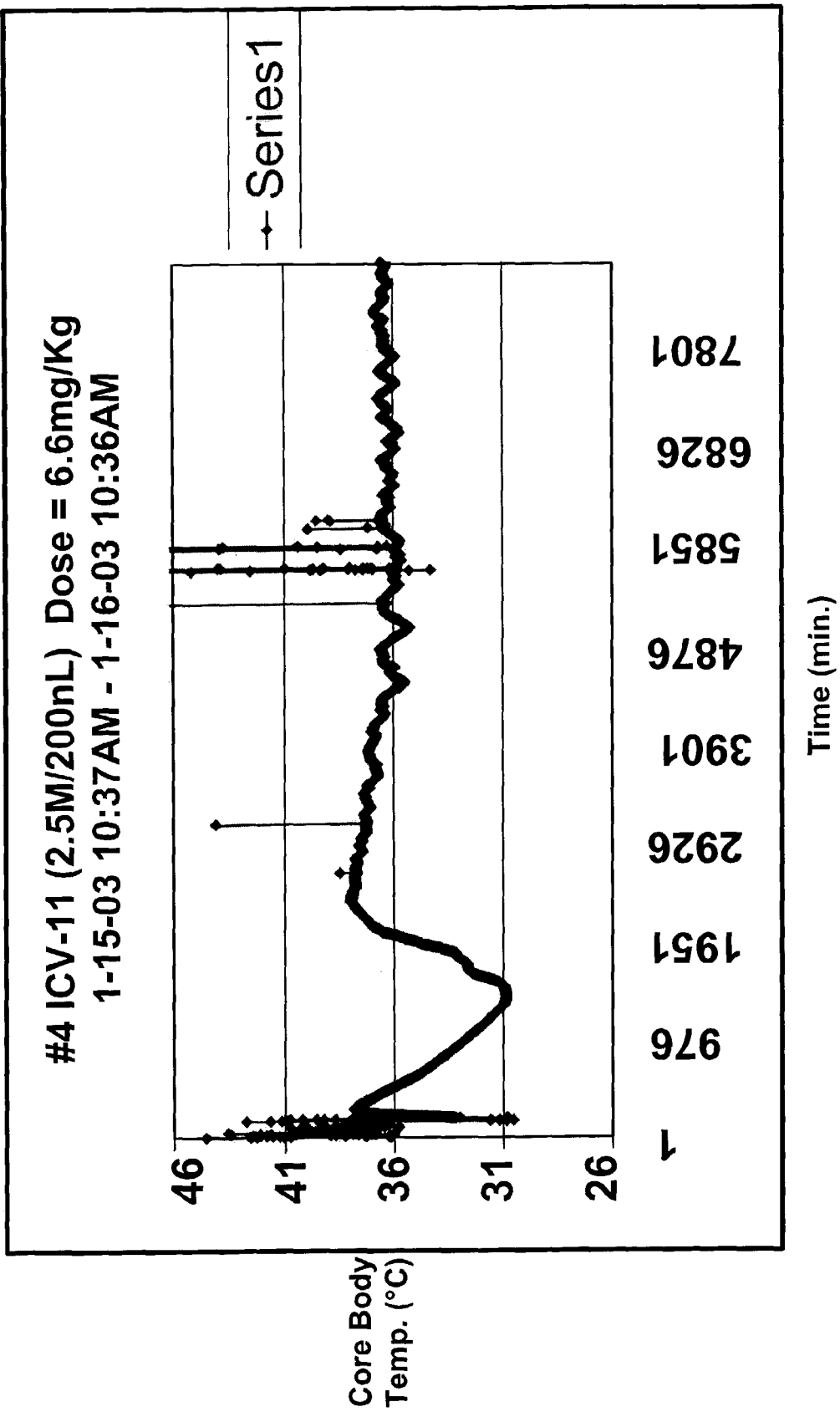
FIG. 9: Graph of core body temperature (° C.) vs. time (hours) following intracerebroventricular injection into a mouse of an iodo-thyronamine compound, $T_1$amine.
Figure 10C:
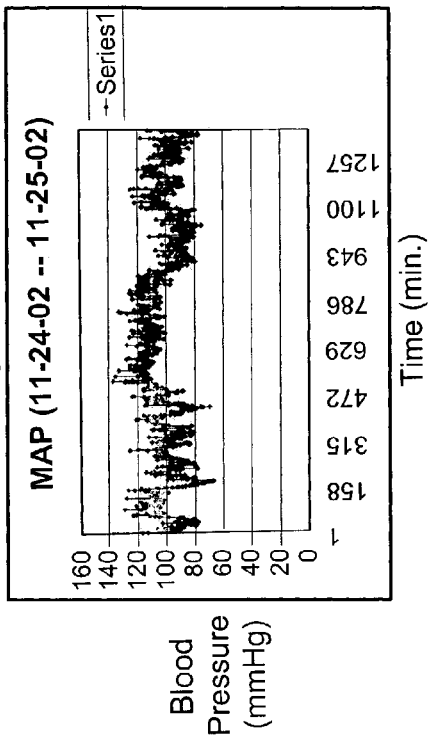
FIG. 10C, 10D: Graph of heart rate vs. time (minutes), or blood pressure (mm Hg) vs. time (minutes), in a mouse in the absence of treatment with an iodo-thyronamine compound.
Figure 10D:
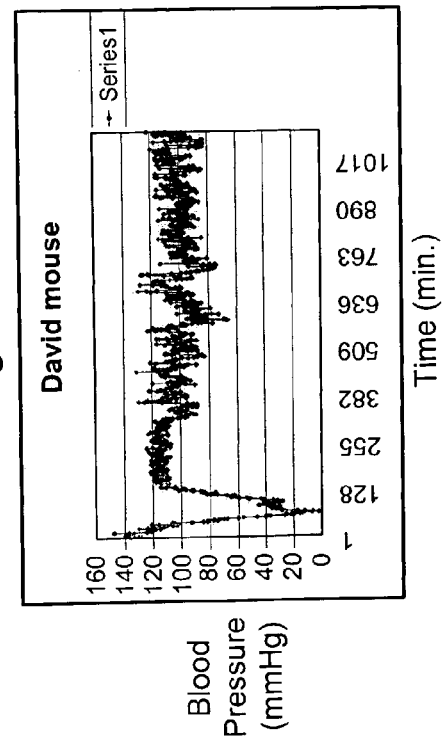
Figure 10A:
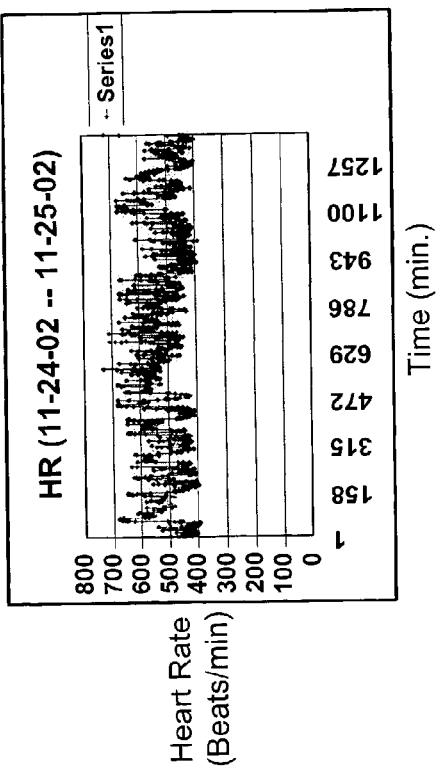
FIG. 10A, 10B: Graph of heart rate vs. time (minutes), or blood pressure (mm Hg) vs. time (minutes), following intraperitoneal injection into a mouse of an iodo-thyronamine compound, $T_1$amine.
Figure 10B:
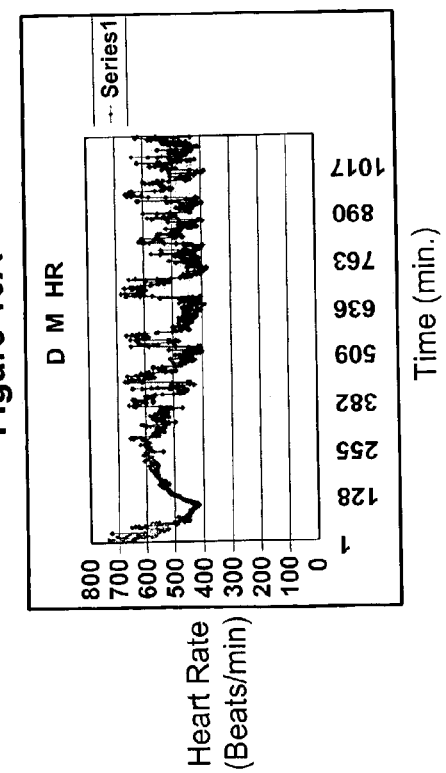
Figure 11A:
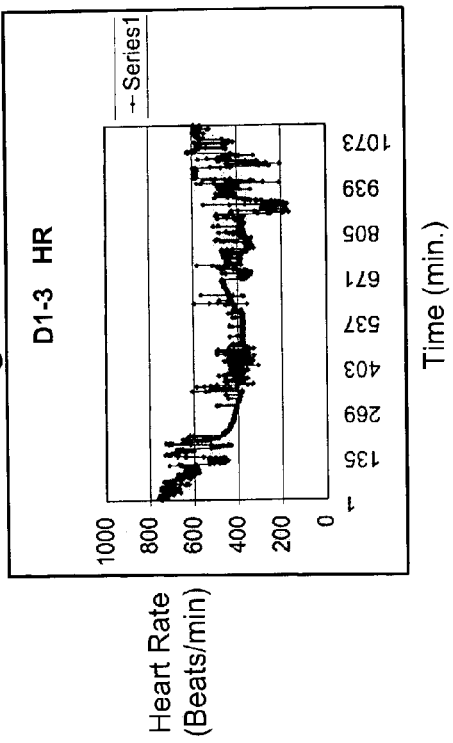
FIG. 11A, 11B: Graph of heart rate vs. time (minutes), or blood pressure (mm Hg) vs. time (minutes), following intraperitoneal injection into a mouse of an iodo-thyronamine compound, T$_1$amine, measured over an approximately 4 hour period.
Figure 11D:
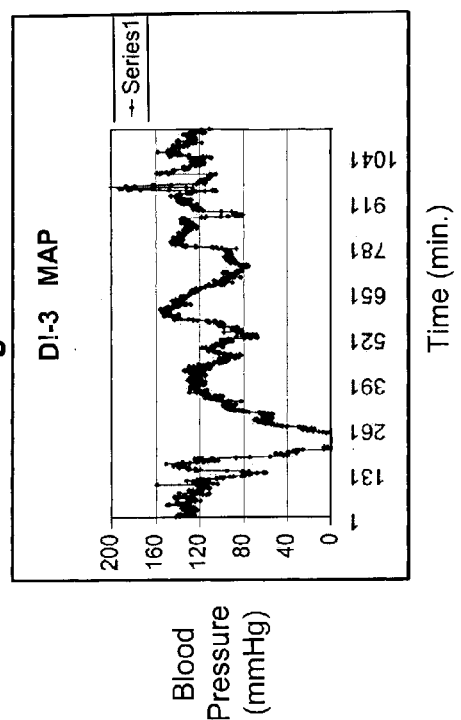
FIG. 11C, 11D: Graph of heart rate vs. time (minutes), or blood pressure (mm Hg) vs. time (minutes), following intraperitoneal injection into a mouse of an iodo-thyronamine compound, T$_1$amine, measured over an approximately 17 hour period.
Figure 11B:
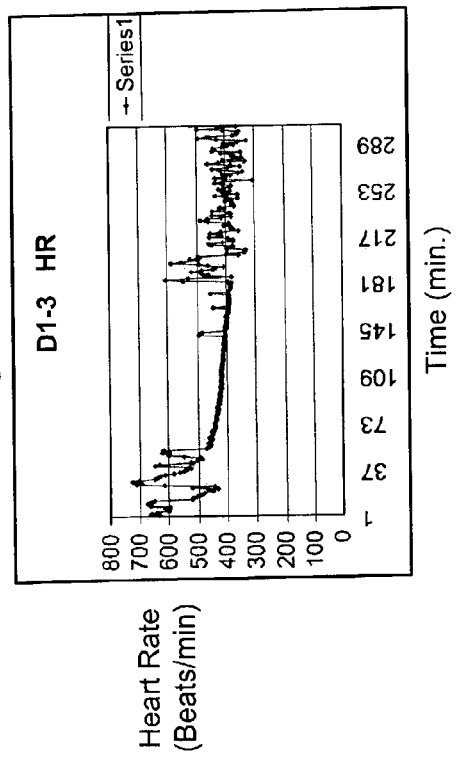
Figure 11C:
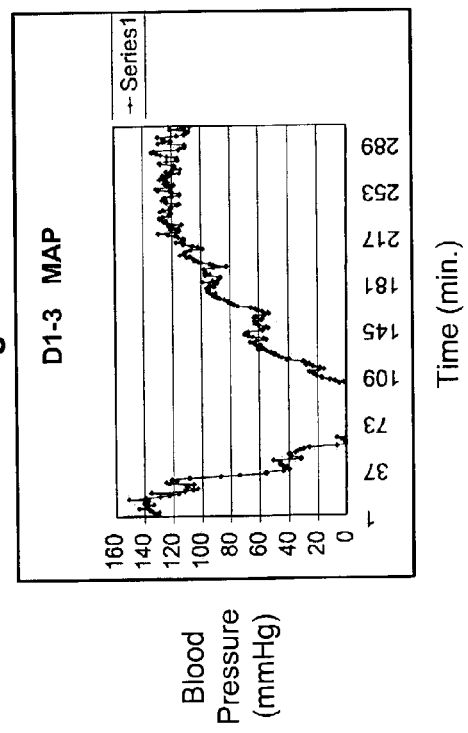
Figure 12A:
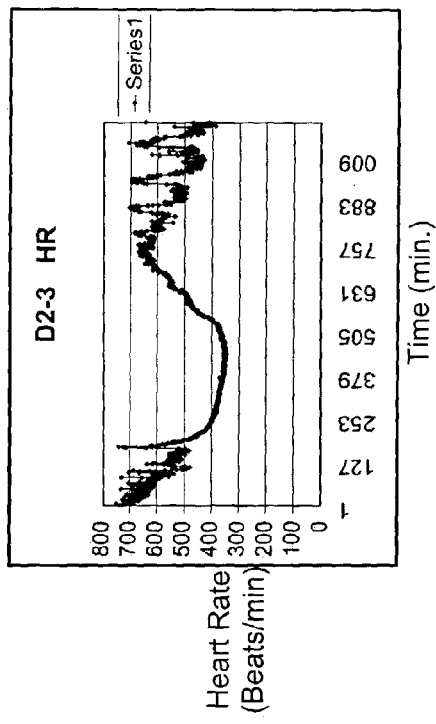
FIG. 12A, 12B: Graph of heart rate vs. time (minutes), or blood pressure (mm Hg) vs. time (minutes), following intraperitoneal injection into a mouse of an iodo-thyronamine compound, T$_1$amine, measured over an approximately 4 hour period.
Figure 12B:
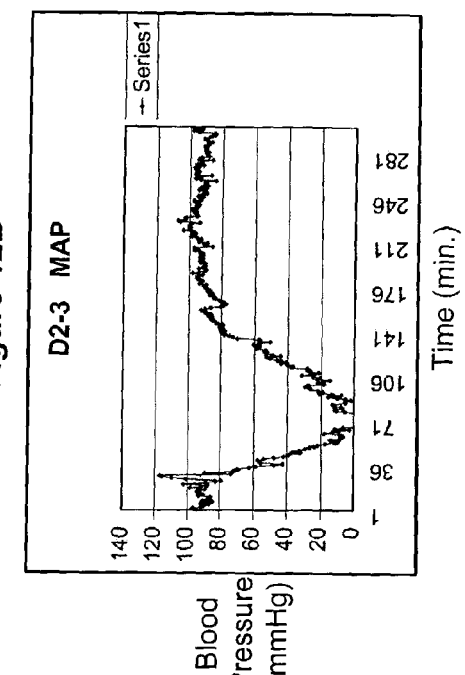
Figure 12C:
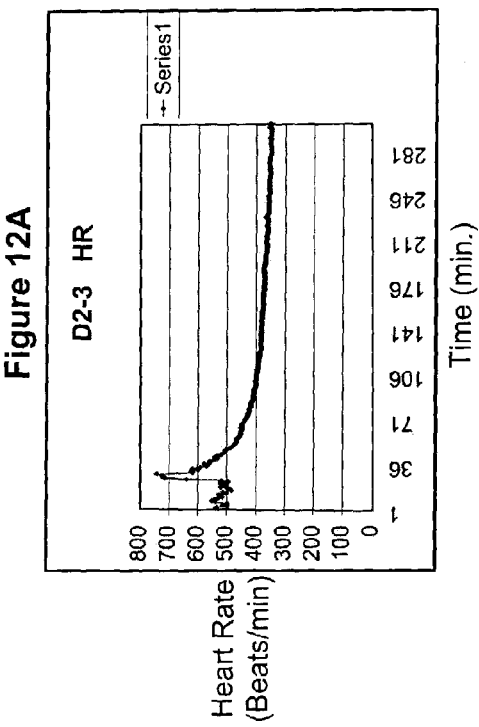
FIG. 12C, 12D: Graph of heart rate vs. time (minutes), or blood pressure (mm Hg) vs. time (minutes), following intraperitoneal injection into a mouse of an iodo-thyronamine compound, T$_1$amine, measured over an approximately 17 hour period.
Figure 12D:
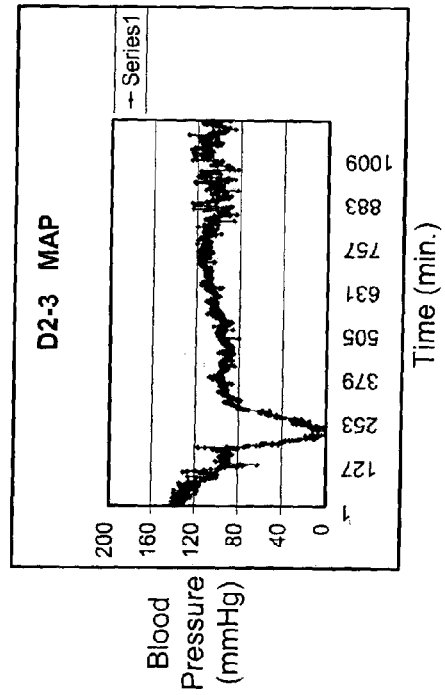

Thermal response was measured in an adult male C57B1/6J mouse to a unilateral intracerebroventricular injection of T$_1$AM dissolved in 60% DMSO/40% normal saline at a dose of 6.6 mg/kg body weight. The mouse was instrumented with a telemetry-emitting temperature sensing probe. See FIG. 9.

Heart rate and blood pressure responses were measured in an adult male C57B1/6J mouse injected intraperitoneally with T$_1$AM in 60% DMSO/40% normal saline at a dose of approximately 75–80 mg/kg body weight in two replicate experiments. See FIGS. 10 and 11.

Heart rate and blood pressure responses were measured in two drug naive adult male C57B1/6J mouse following intraperitoneal injection of T$_1$AM at a dose of approximately 75 mg/kg body weight. See FIGS. 12 and 13.

In each experiment, intraperitoneal or intracerebral injection of T$_1$AM resulted in a decrease in core body temperature of the animal from approximately 38° C. to approximately 29° C. for a period of approximately 6.5 to 8 hours. This period was followed by a full recovery to a stable core body temperature of approximately 38° C. Heart rate of the animals remained constant throughout the treatment period. Blood pressure of the animals varied with the drop in body core temperature, but returned to normal levels within the same time frame as the body core temperature recovery.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula:

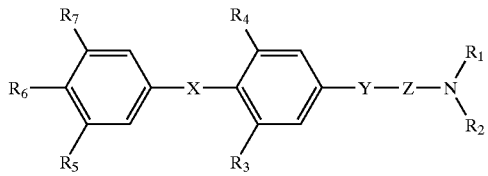

or a stereoisomer, prodrug, pharmaceutically acceptable salt, hydrate, solvate, acid salt hydrate, N-oxide or isomorphic crystalline form thereof;
wherein independently;
$R_1$ and $R_2$ are: H;
Y and Z are: $CH_2$;
$R_3$, is I;
$R_4$, $R_5$, and $R_7$ are: H;
$R_6$ is: OH; and
X is: O.

2. A pharmaceutical composition, comprising at least one pharmaceutically acceptable carrier or excipient and an effective amount of the compound of claim 1.

3. A method of exerting a positive inotropic effect on the heart without affecting the heart rate of a mammalian subject comprising the step of administering to said subject an effective amount of the compound of claim 1.

4. A method of lowering the core body temperature of a mammalian subject comprising the step of administering to said subject an effective amount of the compound of claim 1.

5. The method of claim 4, wherein administering the compound induces torpor or hibernation in said subject.

6. A method for alleviating a disease state in a mammal believed to be responsive to treatment with a thyronamine agonist comprising the step of administering to the mammal a therapeutic amount of a compound of formula:

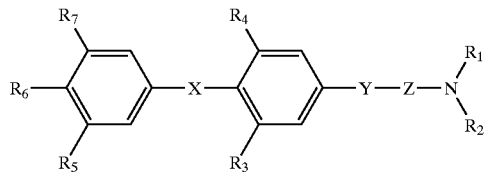

or a stereoisomer, prodrug, pharmaceutically acceptable salt, hydrate, solvate, acid salt hydrate, N-oxide or isomorphic crystalline form thereof;
wherein independently;
$R_1$ and $R_2$ are: H;
Y and Z are: $CH_2$;
$R_3$, is I;
$R_4$, $R_5$, and $R_7$ are: H;
$R_6$ is: OH; and
X is: O.

7. The method of claim 6, wherein said composition is an agonist of a G protein coupled receptor.

8. The method of claim 7, wherein said composition is an agonist of a trace amine receptor.

9. A method for alleviating a disease state in a mammal believed to be responsive to treatment with a thyronamine antagonist comprising administering to the mammal a therapeutic amount of a compound of formula:

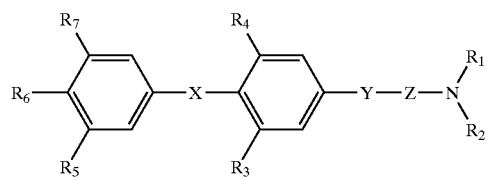

or a stereoisomer, prodrug, pharmaceutically acceptable salt, hydrate, solvate, acid salt hydrate, N-oxide or isomorphic crystalline form thereof;
wherein independently;
$R_1$ and $R_2$ are: H;
Y and Z are: $CH_2$;
$R_3$, is I;
$R_4$, $R_5$, and $R_7$ are: H;
$R_6$ is: OH; and
X is: O.

10. The method of claim 9, wherein said compound is an antagonist of a G protein coupled receptor.

11. The method of claim 10, wherein said compound is an antagonist of a trace amine receptor.

12. The method of claim 6 or claim 9, wherein the disease state is congestive heart failure.

13. The method of claim 6 or claim 9, wherein the disease state is fever or heatstroke.

14. The method of claim 6 or claim 9, wherein the disease state is bipolar disorder, depression, schizophrenia, eating disorders, anxiety, seizure, epilepsy, insomnia and sleeping disorders, gastro esophageal reflux disease, diseases involving gastrointestinal motility or asthma.

15. The method of claim 6 or claim 9, wherein the disease state is diabetes, cardiac arrhythmia, stroke, osteoporosis, obesity, atherosclerosis, hypertension, hyperthyroidism or hypothyroidism.

16. A method of treating a mammalian subject during surgery comprising administering to the subject a therapeutically effective amount of the compound of claim 1, wherein said method reduces the core body temperature and induces anesthesia in the subject.

17. A method of treating a mammalian subject during surgery comprising administering to the subject a therapeutically effective amount of the compound of claim 1 wherein said method reduces blood loss of the subject.

* * * * *